US010286212B2

(12) United States Patent
Simon et al.

(10) Patent No.: US 10,286,212 B2
(45) Date of Patent: *May 14, 2019

(54) NERVE STIMULATION METHODS FOR AVERTING IMMINENT ONSET OR EPISODE OF A DISEASE

(75) Inventors: Bruce J. Simon, Mountain Lakes, NJ (US); Joseph P. Errico, Warren, NJ (US); John T. Raffle, Austin, TX (US)

(73) Assignee: Electrocore, Inc., Basking Ridge, NJ (US)

(*) Notice: Subject to any disclaimer, the term of this patent is extended or adjusted under 35 U.S.C. 154(b) by 376 days.

This patent is subject to a terminal disclaimer.

(21) Appl. No.: 13/357,025

(22) Filed: Jan. 24, 2012

(65) Prior Publication Data

US 2012/0184801 A1  Jul. 19, 2012
US 2016/0367808 A9  Dec. 22, 2016

Related U.S. Application Data

(63) Continuation-in-part of application No. 13/222,087, filed on Aug. 31, 2011, now Pat. No. 9,174,066, which is a continuation-in-part of application No. 13/183,765, filed on Jul. 15, 2011, now Pat. No. 8,874,227, application No. 13/357,025, which is a continuation-in-part of application No. 13/075,746, filed on Mar. 30, 2011, now Pat. No. 8,874,205.

(60) Provisional application No. 61/552,217, filed on Oct. 27, 2011, provisional application No. 61/488,208, (Continued)

(51) Int. Cl.
*A61N 1/36* (2006.01)
*A61N 2/00* (2006.01)

(52) U.S. Cl.
CPC ...... *A61N 1/36064* (2013.01); *A61N 1/36014* (2013.01); *A61N 1/36025* (2013.01); *A61N 2/006* (2013.01)

(58) Field of Classification Search
CPC .............. A61N 1/36064; A61N 1/0404; A61N 1/0456; A61N 1/36014; A61N 1/36025
USPC ................................ 607/45, 46, 48, 149, 150
See application file for complete search history.

(56) References Cited

U.S. PATENT DOCUMENTS

| 3,590,810 A | 7/1971 | Kopecky |
| 4,196,737 A | 4/1980 | Bevilacqua |
| 4,989,605 A | 2/1991 | Rossen |

(Continued)

FOREIGN PATENT DOCUMENTS

| EP | 2777764 | 8/2015 |
| KR | 101242190 | 3/2013 |

(Continued)

OTHER PUBLICATIONS

Greicius et al., Functional connectivity in the resting brain: A network analysis of the default mode hypothesis, PNAS, Jan. 2003, vol. 100, No. 1, pp. 253-258.

(Continued)

*Primary Examiner* — Tammie K Marlen
(74) *Attorney, Agent, or Firm* — Dentons US LLP

(57) ABSTRACT

Transcutaneous electrical and magnetic nerve stimulation devices are disclosed, along with methods of averting imminent medical attacks using energy that is delivered noninvasively by the devices. In particular, the devices and methods involve handheld devices designed to stimulate the vagus nerve of a patient with a signal sufficient to minimize or avert epileptic seizures.

19 Claims, 11 Drawing Sheets

Related U.S. Application Data filed on May 20, 2011, provisional application No. 61/451,259, filed on Mar. 10, 2011.

(56) References Cited

U.S. PATENT DOCUMENTS

| | | | |
|---|---|---|---|
| 5,458,141 A | 10/1995 | Neil | |
| 5,899,922 A | 5/1999 | Loos | |
| 5,983,131 A | 11/1999 | Weaver et al. | |
| 6,341,236 B1 | 1/2002 | Osorio et al. | |
| 6,463,327 B1 | 10/2002 | Lurie et al. | |
| 6,587,719 B1 | 7/2003 | Barrett et al. | |
| 6,610,713 B2 | 8/2003 | Tracey | |
| 7,231,256 B2* | 6/2007 | Wahlstrand | A61N 1/0502 600/548 |
| 7,734,340 B2 | 6/2010 | De Ridder | |
| 7,797,041 B2 | 9/2010 | Libbus et al. | |
| 8,868,172 B2* | 10/2014 | Leyde | A61B 5/0476 600/544 |
| 2001/0003799 A1* | 6/2001 | Boveja | A61N 1/0536 607/45 |
| 2002/0099417 A1 | 7/2002 | Naritoku et al. | |
| 2002/0183237 A1 | 12/2002 | Puskas | |
| 2003/0212311 A1 | 11/2003 | Nova et al. | |
| 2004/0073271 A1 | 4/2004 | Harry et al. | |
| 2004/0243182 A1 | 12/2004 | Cohen et al. | |
| 2004/0249416 A1 | 12/2004 | Yun et al. | |
| 2005/0021092 A1 | 1/2005 | Yun et al. | |
| 2005/0065574 A1 | 3/2005 | Rezai | |
| 2005/0113630 A1 | 5/2005 | Fox et al. | |
| 2005/0137644 A1 | 6/2005 | Boveja et al. | |
| 2005/0216062 A1 | 9/2005 | Herbst | |
| 2005/0267544 A1 | 12/2005 | Lee et al. | |
| 2006/0074284 A1 | 4/2006 | Juola et al. | |
| 2006/0074450 A1 | 4/2006 | Boveja et al. | |
| 2006/0100668 A1 | 5/2006 | Ben-David et al. | |
| 2006/0100671 A1 | 5/2006 | Ridder | |
| 2006/0173510 A1 | 8/2006 | Besio et al. | |
| 2006/0178703 A1 | 8/2006 | Huston et al. | |
| 2007/0027496 A1 | 2/2007 | Parnis et al. | |
| 2007/0106337 A1 | 5/2007 | Errico et al. | |
| 2007/0123952 A1 | 5/2007 | Strother et al. | |
| 2007/0142886 A1 | 6/2007 | Fischell et al. | |
| 2007/0150006 A1 | 6/2007 | Libbus et al. | |
| 2007/0276449 A1 | 11/2007 | Gunter et al. | |
| 2008/0021512 A1 | 1/2008 | Knudson et al. | |
| 2008/0027513 A1 | 1/2008 | Carbunaru | |
| 2008/0045776 A1 | 2/2008 | Fischell et al. | |
| 2008/0051852 A1* | 2/2008 | Dietrich | A61H 39/002 607/45 |
| 2008/0077192 A1 | 3/2008 | Harry et al. | |
| 2008/0114199 A1 | 5/2008 | Riehl et al. | |
| 2008/0132964 A1 | 6/2008 | Cohen et al. | |
| 2008/0177190 A1 | 7/2008 | Libbus et al. | |
| 2008/0208266 A1* | 8/2008 | Lesser et al. | 607/2 |
| 2008/0288017 A1* | 11/2008 | Kieval | A61N 1/36014 607/44 |
| 2008/0306325 A1 | 12/2008 | Burnett et al. | |
| 2009/0112283 A1 | 4/2009 | Kriksunov et al. | |
| 2009/0132018 A1 | 5/2009 | DiUbaldi et al. | |
| 2009/0157149 A1 | 6/2009 | Wahlgren et al. | |
| 2009/0234417 A1 | 9/2009 | Pastena et al. | |
| 2009/0234419 A1 | 9/2009 | Maschino et al. | |
| 2009/0240297 A1 | 9/2009 | Shavit et al. | |
| 2009/0287035 A1 | 11/2009 | Dietrich et al. | |
| 2010/0030299 A1 | 2/2010 | Covalin | |
| 2010/0152794 A1 | 6/2010 | Radivojevic et al. | |
| 2010/0286553 A1 | 11/2010 | Feler et al. | |
| 2011/0046432 A1 | 2/2011 | Simon et al. | |
| 2011/0152967 A1 | 6/2011 | Simon et al. | |
| 2011/0213295 A1 | 9/2011 | Henley et al. | |
| 2011/0224749 A1 | 9/2011 | Ben-David et al. | |
| 2011/0230701 A1 | 9/2011 | Simon et al. | |
| 2012/0029601 A1 | 2/2012 | Simon et al. | |
| 2012/0283697 A1 | 11/2012 | Kim et al. | |
| 2012/0303080 A1 | 11/2012 | Ben-David et al. | |
| 2013/0006322 A1 | 1/2013 | Tai | |
| 2013/0245486 A1 | 9/2013 | Simon et al. | |
| 2014/0005743 A1 | 1/2014 | Giuffrida et al. | |
| 2015/0165226 A1 | 6/2015 | Simon et al. | |
| 2015/0190637 A1 | 7/2015 | Simon et al. | |

FOREIGN PATENT DOCUMENTS

| | | |
|---|---|---|
| WO | WO 1993/01862 | 2/1993 |
| WO | WO2005/007120 | 1/2005 |
| WO | WO2007/092062 | 8/2007 |
| WO | WO2008/042902 | 4/2008 |
| WO | WO2007/058780 | 5/2008 |
| WO | WO 2009/021080 | 2/2009 |
| WO | WO 2009/135693 | 11/2009 |
| WO | WO2013066135 | 5/2013 |

OTHER PUBLICATIONS

Heneka et al., Locus ceruleus controls Alzheimer's disease pathology by modulating microglial functions through norepinephrine, PNAS, Mar. 2010, vol. 107, No. 13, pp. 6058-6063.

Lee et al., Clustering of Resting State Networks, PLoS One, Jul. 2012, vol. 7, Issue 7, pp. 1-12.

International Search Report and Written Opinion dated Mar. 26, 2008 in related PCT Application No. PCT/US2006/042752 filed Nov. 1, 2006 (7 pages).

International Search Report and Written Opinion dated Sep. 17, 2007 in related PCT Application No. PCT/US2006/042828 filed Nov. 2, 2006 (5 pages).

International Search Report and Written Opinion dated May 8, 2007 in related PCT Application No. PCT/US2006/042823 filed Nov. 2, 2006 (5 pages).

International Search Report and Written Opinion dated Dec. 22, 2011 in related PCT Application No. PCT/US2011/049844 filed Aug. 31, 2011 (9 pages).

International Search Report and Written Opinion dated Apr. 30, 2013 in related PCT Application No. PCT/US2013/023014 filed Jan. 24, 2013 (7 pages).

International Search Report and Written Opinion dated Dec. 11, 2013 in related PCT Application No. PCT/US2013/058079 filed Sep. 4, 2013 (8 pages).

International Search Report and Written Opinion dated Jan. 29, 2014 in related PCT Application No. PCT/US2013/068804 filed Nov. 6, 2013 (10 pages).

International Search Report and Written Opinion dated Aug. 15, 2015 in related Application No. PCT/US15/31847 filed May 20, 2015 (10 pages).

Europe Office Action dated Apr. 24, 2018 in related Application No. 15796247.3 filed May 20, 2015 (6 pages).

KR101242190 dated Mar. 25, 2013, Espacenet computer generated English translation (11 pages).

Europe Office Action dated Jul. 26, 2018 in related Application No. 11818591.7 filed Aug. 12, 2011 (8 pages).

* cited by examiner

FIG. 1
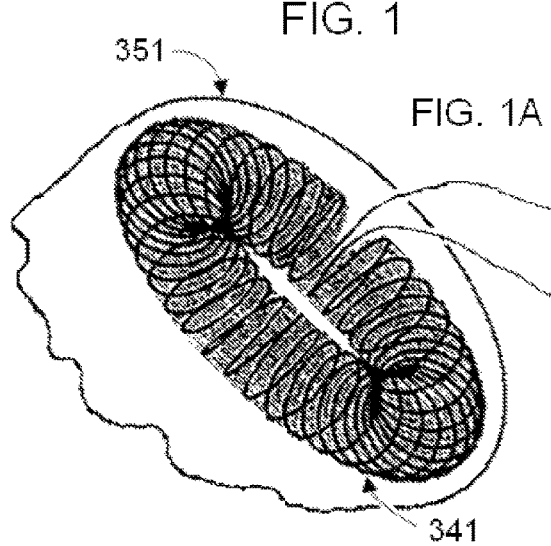
FIG. 1A
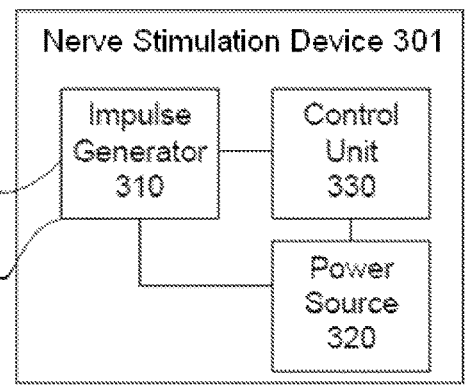
FIG. 1B
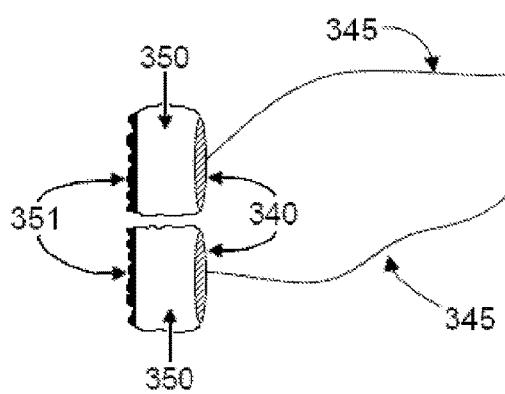
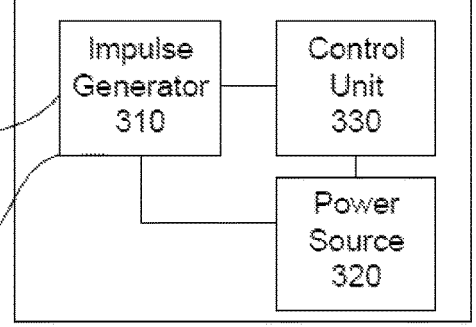

FIG. 2
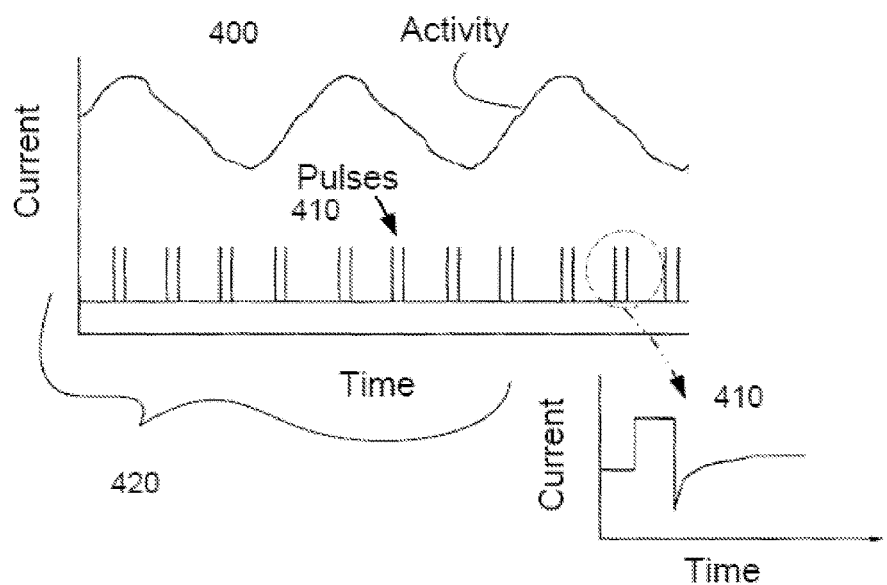
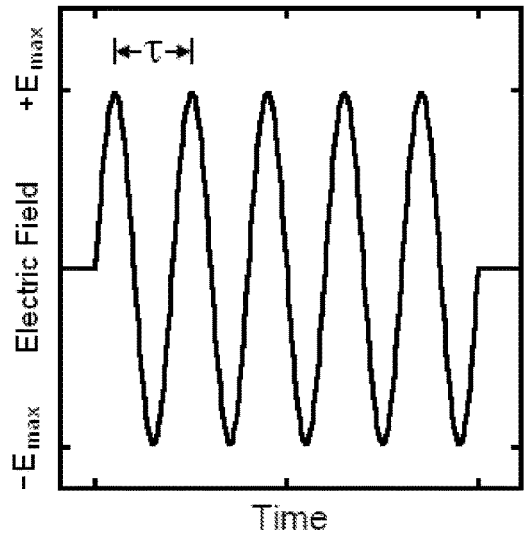
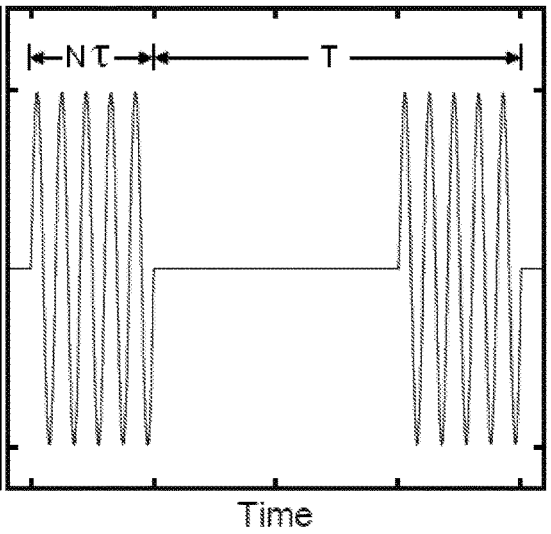

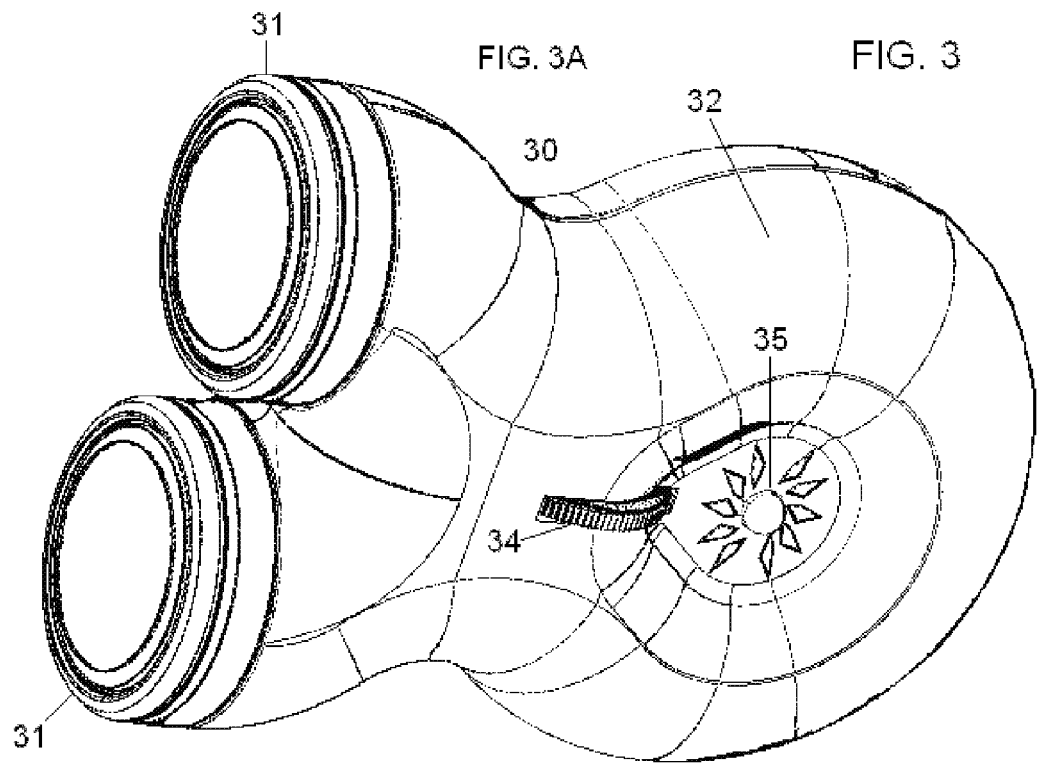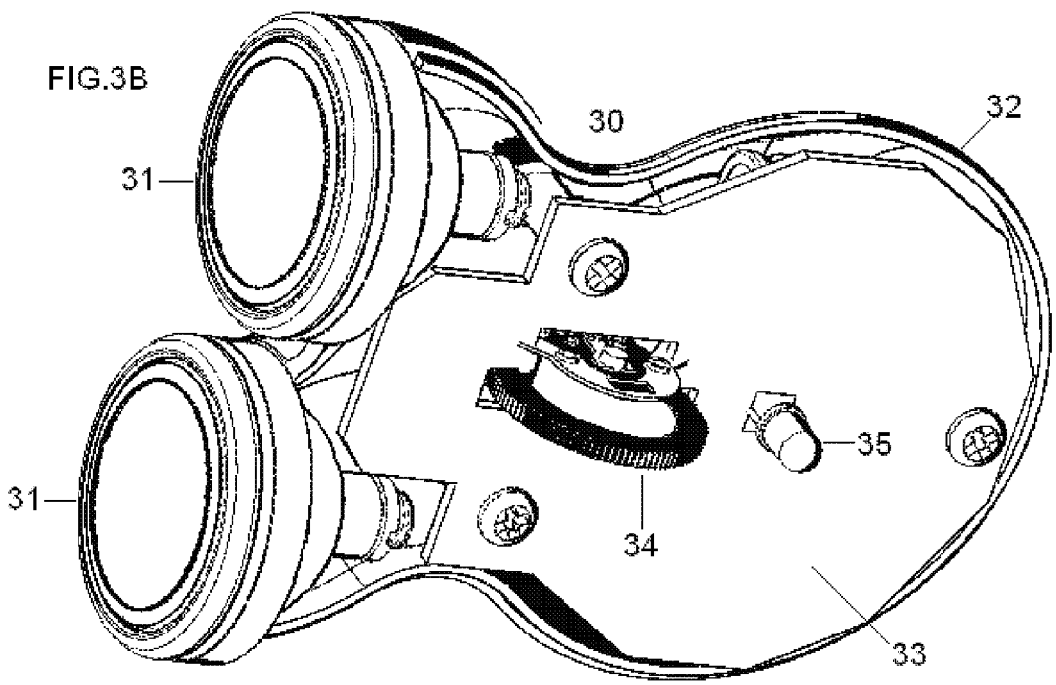

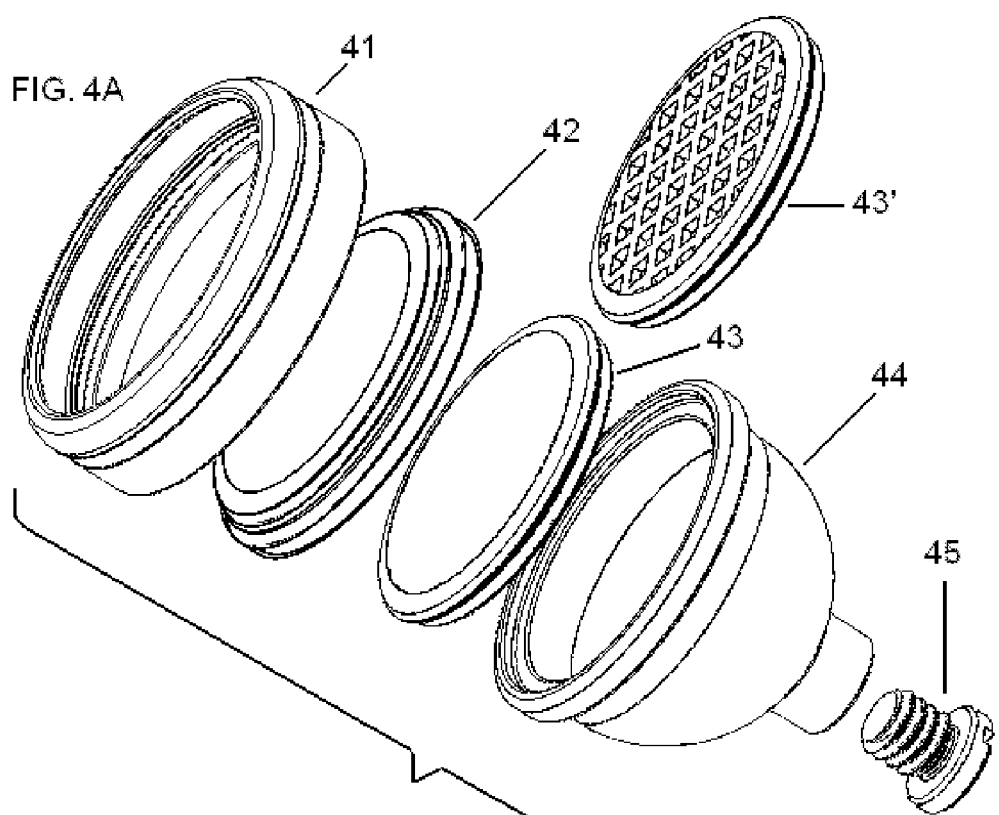
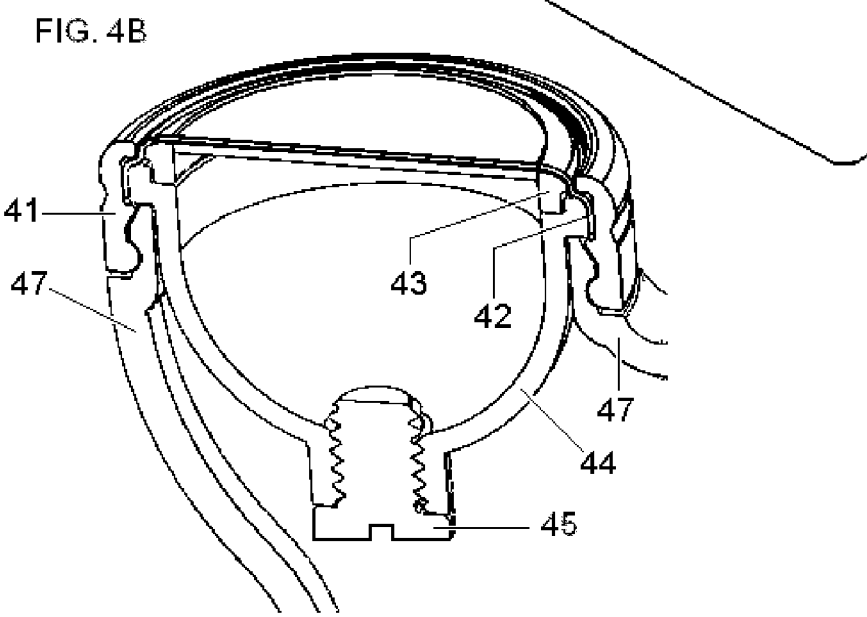

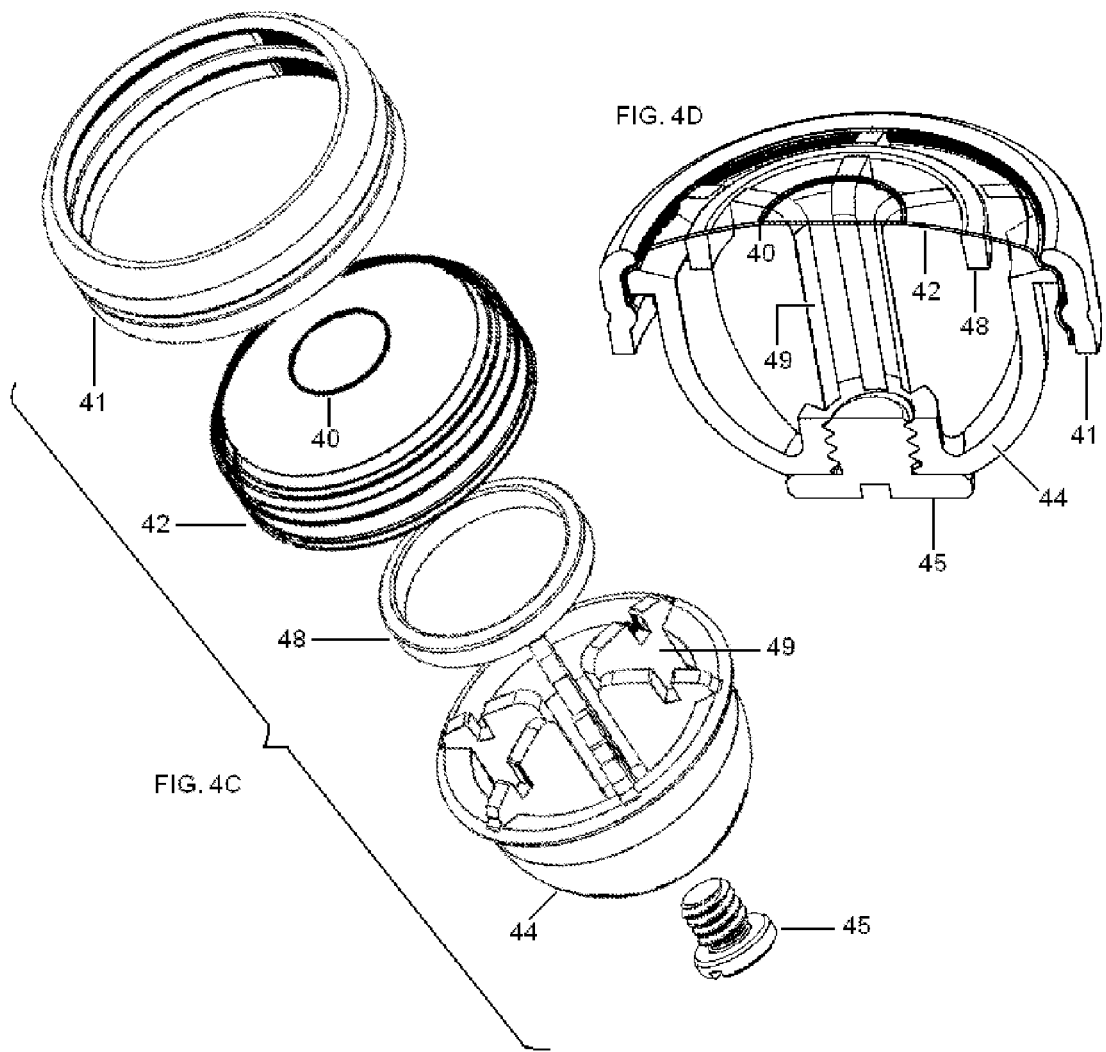

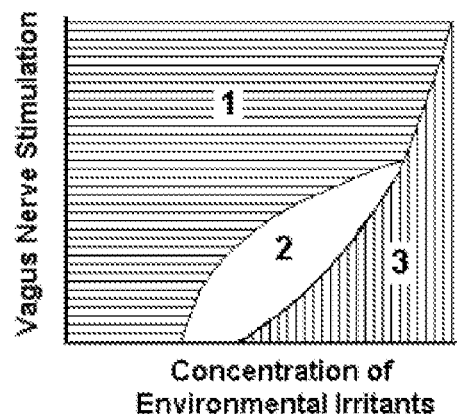
FIG. 9A
1 Phase Drift
2 Irregular Region
3 Phase Locked
FIG. 9B
1 Phase Drift
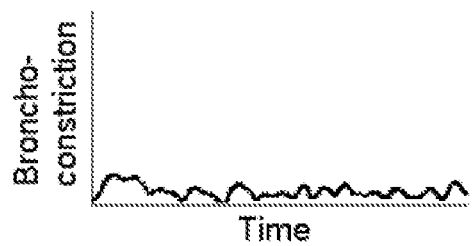
2 Irregular Region
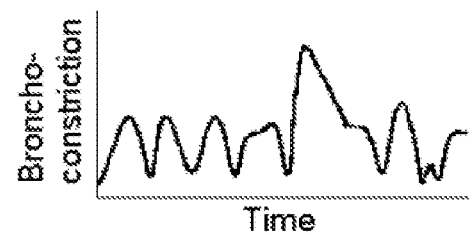
3. Phase Locked (in same potential well)
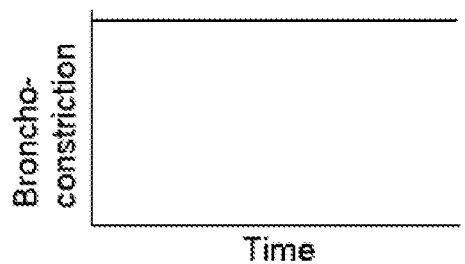

NERVE STIMULATION METHODS FOR AVERTING IMMINENT ONSET OR EPISODE OF A DISEASE

CROSS REFERENCE TO RELATED APPLICATIONS

This application claims the benefit of priority to U.S. Provisional Patent Application No. 61/552,217 filed Oct. 27, 2011; and this application is a continuation-in-part of U.S. patent application Ser. No. 13/222,087 filed Aug. 31, 2011 now U.S. Pat. No. 9,174,066 issued Nov. 3, 2015, which is a continuation-in-part of U.S. patent application Ser. No. 13/183,765 filed Jul. 15, 2011 now U.S. Pat. No. 8,874,227 issued Oct. 28, 2014, which claims the benefit of priority of U.S. Provisional Patent Application No. 61/488,208 filed May 20, 2011; and this application is a continuation-in-part to U.S. patent application Ser. No. 13/075,746 filed Mar. 30, 2011 now U.S. Pat. No. 8,874,205 issued Oct. 28, 2014, which claims the benefit of priority of U.S. provisional patent application 61/451,259 filed Mar. 10, 2011; the entire disclosures of which are hereby incorporated by reference for all purposes.

BACKGROUND OF THE INVENTION

The field of the present invention relates to the delivery of energy impulses (and/or fields) to bodily tissues for prophylactic purposes. It relates more specifically to the use of non-invasive devices and methods for transcutaneous electrical nerve stimulation and magnetic nerve stimulation, along with methods for averting imminent medical disorders using energy that is delivered by such devices. The disorders comprise the following medical problems: asthma attacks and COPD exacerbations, epileptic seizures, migraine or other headaches having sudden onset, ventricular fibrillation/tachycardia, myocardial infarction, transient ischemic attacks or strokes, atrial fibrillation, panic attacks and attacks of depression. According to the invention, a patient at risk for such attacks is monitored, preferably using ambulatory or noninvasive sensors; signals from the sensors are analyzed automatically using a device to forecast that an attack may be imminent; the analyzing device warns the patient or health provider that an attack may be imminent; and transcutaneous electrical nerve stimulation or magnetic nerve stimulation, preferably of the vagus nerve, is performed is order to avert, prevent, delay, abort, shorten, or ameliorate the attack.

The use of electrical stimulation for treatment of medical conditions has been well known in the art for nearly two thousand years. It has been recognized that electrical stimulation of the brain and/or the peripheral nervous system and/or direct stimulation of the malfunctioning tissue holds significant promise for the treatment of many ailments, because such stimulation is generally a wholly reversible and non-destructive treatment.

One of the most successful applications of modern understanding of the electrophysiological relationship between muscle and nerves is the cardiac pacemaker. Although origins of the cardiac pacemaker extend back into the 1800's, it was not until 1950 that the first practical, albeit external and bulky, pacemaker was developed. The first truly functional, wearable pacemaker appeared in 1957, and in 1960, the first fully implantable pacemaker was developed.

Around this time, it was also found that electrical leads could be connected to the heart through veins, which eliminated the need to open the chest cavity and attach the lead to the heart wall. In 1975 the introduction of the lithium-iodide battery prolonged the battery life of a pacemaker from a few months to more than a decade. The modern pacemaker can treat a variety of different signaling pathologies in the cardiac muscle, and can serve as a defibrillator as well (see U.S. Pat. No. 6,738,667 to DENO, et al., the disclosure of which is incorporated herein by reference).

Another application of electrical stimulation of nerves has been the treatment of radiating pain in the lower extremities by stimulating the sacral nerve roots at the bottom of the spinal cord (see U.S. Pat. No. 6,871,099 to WHITEHURST, et al., the disclosure of which is incorporated herein by reference).

Many such therapeutic applications of electrical stimulation involve the surgical implantation of electrodes within a patient. In contrast, devices used for the medical procedures that are disclosed here stimulate nerves by transmitting energy to nerves and tissue non-invasively. They may offer the patient an alternative that does not involve surgery. A medical procedure is defined as being non-invasive when no break in the skin (or other surface of the body, such as a wound bed) is created through use of the method, and when there is no contact with an internal body cavity beyond a body orifice (e.g., beyond the mouth or beyond the external auditory meatus of the ear). Such non-invasive procedures are distinguished from invasive procedures (including minimally invasive procedures) in that invasive procedures do involve inserting a substance or device into or through the skin or into an internal body cavity beyond a body orifice. For example, transcutaneous electrical nerve stimulation (TENS) is non-invasive because it involves attaching electrodes to the surface of the skin (or using a form-fitting conductive garment) without breaking the skin. In contrast, percutaneous electrical stimulation of a nerve is minimally invasive because it involves the introduction of an electrode under the skin, via needle-puncture of the skin (see commonly assigned co-pending US Patent Application 2010/0241188, entitled Percutaneous Electrical Treatment of Tissue to ERRICO et al, which is hereby incorporated by reference in its entirety).

Potential advantages of non-invasive medical methods and devices relative to comparable invasive procedures are as follows. The patient may be more psychologically prepared to experience a procedure that is non-invasive and may therefore be more cooperative, resulting in a better outcome. Non-invasive procedures may avoid damage of biological tissues, such as that due to bleeding, infection, skin or internal organ injury, blood vessel injury, and vein or lung blood clotting. Non-invasive procedures generally present fewer problems with biocompatibility. In cases involving the attachment of electrodes, non-invasive methods have less of a tendency for breakage of leads, and the electrodes can be easily repositioned if necessary. Non-invasive methods are sometimes painless or only minimally painful and may be performed without the need for even local anesthesia. Less training may be required for use of non-invasive procedures by medical professionals. In view of the reduced risk ordinarily associated with non-invasive procedures, some such procedures may be suitable for use by the patient or family members at home or by first-responders at home or at a workplace, and the cost of non-invasive procedures may be reduced relative to comparable invasive procedures.

Non-invasive transcutaneous electrical nerve stimulation (TENS) electrodes were developed originally for treating different types of pain, including pain in a joint or lower back, cancer pain, post-operative pain, post-traumatic pain, and pain associated with labor and delivery. As TENS was being developed to treat pain, non-invasive electrical stimulation using surface electrodes was simultaneously developed for additional therapeutic or diagnostic purposes, which are known collectively as electrotherapy. Neuromuscular electrical stimulation (NMES) stimulates normally innervated muscle in an effort to augment strength and endurance of normal (e.g., athletic) or damaged (e.g., spastic) muscle. Functional electrical stimulation (FES) is used to activate nerves innervating muscle affected by paralysis resulting from spinal cord injury, head injury, stroke and other neurological disorders, or muscle affected by foot drop and gait disorders. FES is also used to stimulate muscle as an orthotic substitute, e.g., replace a brace or support in scoliosis management. Another application of surface electrical stimulation is chest-to-back stimulation of tissue, such as emergency defibrillation and cardiac pacing. Surface electrical stimulation has also been used to repair tissue, by increasing circulation through vasodilation, by controlling edema, by healing wounds, and by inducing bone growth. Surface electrical stimulation is also used for iontophoresis, in which electrical currents drive electrically charged drugs or other ions into the skin, usually to treat inflammation and pain, arthritis, wounds or scars.

Stimulation with surface electrodes is also used to evoke a response for diagnostic purposes, for example in peripheral nerve stimulation (PNS) that evaluates the ability of motor and sensory nerves to conduct and produce reflexes. Surface electrical stimulation is also used in electroconvulsive therapy to treat psychiatric disorders; electroanesthesia, for example, to prevent pain from dental procedures; and electrotactile speech processing to convert sound into tactile sensation for the hearing impaired. All of the above-mentioned applications of surface electrode stimulation are intended not to damage the patient, but if higher currents are used with special electrodes, electrosurgery may be performed as a means to cut, coagulate, desiccate, or fulgurate tissue [Mark R. PRAUSNITZ. The effects of electric current applied to skin: A review for transdermal drug delivery. Advanced Drug Delivery Reviews 18 (1996) 395-425].

Another form of non-invasive electrical stimulation is magnetic stimulation. It involves the induction, by a time-varying magnetic field, of electrical fields and current within tissue, in accordance with Faraday's law of induction. Magnetic stimulation is non-invasive because the magnetic field is produced by passing a time-varying current through a coil positioned outside the body, inducing at a distance an electric field and electric current within electrically-conducting bodily tissue. The electrical circuits for magnetic stimulators are generally complex and expensive and use a high current impulse generator that may produce discharge currents of 5,000 amps or more, which is passed through the stimulator coil to produce a magnetic pulse. The principles of electrical nerve stimulation using a magnetic stimulator, along with descriptions of medical applications of magnetic stimulation, are reviewed in: Chris HOVEY and Reza Jalinous, The Guide to Magnetic Stimulation, The Magstim Company Ltd, Spring Gardens, Whitland, Carmarthenshire, SA34 0HR, United Kingdom, 2006.

Despite its attractiveness, non-invasive electrical stimulation of a nerve is not always possible or practical. This is primarily because the stimulators may not be able to stimulate a deep nerve selectively or without producing excessive pain, because the stimulation may unintentionally stimulate nerves other than the nerve of interest, including nerves that cause pain. For this reason, forms of electrical stimulation other than TENS may be best suited for the treatment of particular types of pain [Paul F. WHITE, shitong Li and Jen W. Chiu. Electroanalgesia: Its Role in Acute and Chronic Pain Management. Anesth Analg 92(2001):505-13]. Accordingly, there remains a long-felt but unsolved need to stimulate nerves totally non-invasively, selectively, and essentially without producing pain.

As compared with what would be experienced by a patient undergoing non-invasive stimulation with conventional TENS or magnetic stimulation methods, the stimulators disclosed herein and in the related applications cited in the section CROSS REFERENCE TO RELATED APPLICATIONS produce relatively little pain for a given depth of stimulus penetration, but nevertheless stimulate the target nerve to achieve therapeutic results. Or conversely, for a given amount of pain or discomfort on the part of the patient (e.g., the threshold at which such discomfort or pain begins), the stimulators disclosed herein and in the related applications achieve a greater depth of penetration or power of the stimulus under the skin. When some nerves are stimulated electrically, they may produce undesirable responses in addition to the therapeutic effect that is intended. For example, the stimulated nerves may produce unwanted muscle twitches. The stimulators disclosed herein and in the related applications selectively produce only the intended therapeutic effect when they are used to stimulate the target nerve.

The stimulators disclosed herein and in those related applications are particularly useful for performing noninvasive stimulation of the vagus nerve in the neck. Invasive vagus nerve stimulation (VNS, also known as vagal nerve stimulation) was developed initially for the treatment of partial onset epilepsy and was subsequently developed for the treatment of depression and other disorders. The left vagus nerve is ordinarily stimulated at a location within the neck by first surgically implanting an electrode there, then connecting the electrode to an electrical stimulator [U.S. Pat. No. 4,702,254 entitled Neurocybernetic prosthesis, to ZABARA; U.S. Pat. No. 6,341,236 entitled Vagal nerve stimulation techniques for treatment of epileptic seizures, to OSORIO et al and U.S. Pat. No. 5,299,569 entitled Treatment of neuropsychiatric disorders by nerve stimulation, to WERNICKE et al; G. C. ALBERT, C. M. Cook, F. S. Prato, A. W. Thomas. Deep brain stimulation, vagal nerve stimulation and transcranial stimulation: An overview of stimulation parameters and neurotransmitter release. Neuroscience and Biobehavioral Reviews 33 (2009) 1042-1060; GROVES D A, Brown V J. Vagal nerve stimulation: a review of its applications and potential mechanisms that mediate its clinical effects. Neurosci Biobehav Rev (2005) 29:493-500; Reese TERRY, Jr. Vagus nerve stimulation: a proven therapy for treatment of epilepsy strives to improve efficacy and expand applications. Conf Proc IEEE Eng Med Biol Soc. 2009; 2009:4631-4634; Timothy B. MAPSTONE. Vagus nerve stimulation: current concepts. Neurosurg Focus 25 (3, 2008):E9, pp. 1-4]. An advantage of devices according to the present invention, which are also disclosed the related applications cited in the section CROSS REFERENCE TO RELATED APPLICATIONS, is that they can be used to perform VNS noninvasively on the neck without causing pain or nonselective nerve stimulation. Furthermore, devices disclosed in the related applications can be used to stimulate the vagus nerve at locations other than the neck.

Vagus nerve stimulation has heretofore been used to treat patients who are only at a statistical risk for experiencing epileptic seizures. For example, the patient will have been diagnosed with epilepsy or is otherwise considered to be at risk for having seizures, using statistical or epidemiological risk assessment methods. Such risk assessment methods predict only the probability of a seizure over a period of typically weeks or months, but do not attempt to forecast that an attack is imminent within a matter of minutes or other short period of time. Thus, currently practiced VNS treatment methods stimulate the patient chronically or at scheduled times, rather than stimulating at times based on predicted epileptic seizures.

It would be preferable to actually forecast an epileptic seizure so as to perform a prophylactic countermeasure, and methods have been proposed to do so [MORMANN F, Andrzejak R G, Elger C E, Lehnertz K. Seizure prediction: the long and winding road. Brain 130(Pt 2, 2007):314-33]. Proposed countermeasures are the on-demand excretion of fast-acting anticonvulsant substances, local cooling, biofeedback operant conditioning, and electrical or other stimulation to reset brain dynamics to a state that will not develop into a seizure. The electrical stimulation countermeasures that have been proposed involved deep-brain stimulation or other uses of implanted electrodes, but not non-invasive vagal nerve stimulation. In one aspect of the present invention, non-invasive vagal nerve stimulation is performed as a countermeasure for forecasted epileptic seizure, instead of using implanted electrodes or brain stimulation.

The literature on "acute risk factors" for acute events other than epileptic seizures does not attempt to forecast and take prophylactic nerve stimulation countermeasures against the actual onset of the disease event. Instead, the goal has been detection of the attack in its early stages (e.g, transient ischemia, thrombosis, and initial signs of ventricular fibrillation, in the case of cardiovascular events [Tofler G H, Muller J E. Triggering of acute cardiovascular disease and potential preventive strategies. Circulation. 114(17, 2006): 1863-72]). The treatment methods that are currently practiced in connection with such acute events are therefore generally intended only to lessen the probability that an acute event will occur over a period of weeks or months, or possibly to abort an attack that is already in progress, but not to predict and avert an attack is that is imminent within a matter of minutes or other short period of time. In one aspect of the present invention, forecasting and non-invasive vagal nerve stimulation is performed as a countermeasure for many types of acute events, comprising: asthma attacks, epileptic seizures, migraine or other headaches having sudden onset, ventricular fibrillation/tachycardia, myocardial infarction, transient ischemic attacks or strokes, atrial fibrillation, panic attacks or attacks of depression. Thus, the present invention differs from the prior art in that it attempts to forecast such an imminent attack (generally within seconds to hours), warn the patient that an attack may be imminent, and use noninvasive nerve stimulation to prevent or avert the attack.

The forecast that an attack may be imminent is based upon the automatic analysis of physiological and/or environmental signals that are provided preferably by non-invasive sensors situated on, about, or near the patient. Such sensors may comprise those used in conventional Holter and bedside monitoring applications, for monitoring heart rate, ECG, respiration, core temperature, hydration, blood pressure, brain function, oxygenation, and skin temperature. The sensors may also be embedded in garments or placed in sports wristwatches, as currently used in programs that monitor the physiological status of soldiers [G. A. Shaw, A. M. Siegel, G. Zogbi, and T. P. Opar. Warfighter physiological and environmental monitoring: a study for the U.S. Army Research Institute in Environmental Medicine and the Soldier Systems Center. MIT Lincoln Laboratory, Lexington Mass. 1 Nov. 2004, pp. 1-141]. More sophisticated versions of conventional ambulatory monitoring devices may also be used, for example, when electrical impedance measurements are used noninvasively to image the lung, heart, or brain [David Holder. Electrical impedance tomography: methods, history, and applications. Institute of Physics Publishing, Bristol and Philadelphia; 2005].

Sensors may be selected according to their relevance to the physiology of the disease that is being forecast. For example, for some applications the sensors may measure bodily chemicals using non-invasive transdermal reverse iontophoresis [Leboulanger B, Guy R H, Delgado-Charro M B. Reverse iontophoresis for non-invasive transdermal monitoring. Physiol Meas. 25(3, 2004):R35-50]. For brain monitoring, they may comprise ambulatory EEG sensors [Casson A, Yates D, Smith S, Duncan J, Rodriguez-Villegas E. Wearable electroencephalography. What is it, why is it needed, and what does it entail? IEEE Eng Med Biol Mag. 29(3, 2010):44-56] or optical topography systems for mapping prefrontal cortex activation [Atsumori H, Kiguchi M, Obata A, Sato H, Katura T, Funane T, Maki A. Development of wearable optical topography system for mapping the prefrontal cortex activation. Rev Sci Instrum. 2009 April; 80(4):043704].

The sensors may also comprise accelerometers for detailed measurement of the patients' movements and metabolically-relevant activity [Mathie M J, Coster A C, Lovell N H, Celler B G. Accelerometry: providing an integrated, practical method for long-term, ambulatory monitoring of human movement. Physiol Meas. 2004 April; 25(2):R1-20] or for evaluation of potential motion artifacts in other signals such as the EEG [Sweeney K T, Leamy D J, Ward T E, McLoone S. Intelligent artifact classification for ambulatory physiological signals. Conf Proc IEEE Eng Med Biol Soc. 2010; 2010:6349-52]. Nearby sensors for environmental variables may also be useful for making forecasts, the values of which may be transmitted, directly in the case of ambulatory monitors or wirelessly in the case of non-portable sensors, to the device that is aggregating the signals used to make the forecast. For example, vest-based sensors would be useful for the evaluation of potential environmental asthma triggers [e.g., Kirk J. Englehardt and John Toon. Asthma attack: Vest-based sensors monitor environmental exposure to help understand causes: web page (www) at the Georgia Tech Research Institute (.gtri) of Georgia Tech (.gatech) educational domain (.edu) in subdomain: /casestudy/asthma-vest-helps-id-asthma-causes; patent application US20110144515 Systems and methods for providing environmental monitoring, to Bayer et al.; and U.S. Pat. No. 7,119,900; entitled Pollen sensor and method, to Okumura et al].

A common feature of asthma attacks, epileptic seizures, migraine or other headaches having sudden onset, ventricular fibrillation/tachycardia, myocardial infarction, transient ischemic attacks or strokes, atrial fibrillation, panic attacks, attacks of depression, and the like, is that they all may occur suddenly. On one level, they all have different particular mechanisms, but on a more general level they all appear to be types of phase transitions, wherein there is an abrupt change from a possibly normal physiological dynamic phase to a pathological dynamical phase. As a type of phase transition, they share features with non-biological, non-equilibrium phase transitions such as the onset of lasing in a laser or the abrupt change from laminar to turbulent flow in fluid dynamics. Such phase transitions are described by non-linear dynamical equations that exhibit generic properties immediately before the change of phase occurs [Scheffer M, Bascompte J, Brock W A, Brovkin V, Carpenter S R, Dakos V, Held H, van Nes E H, Rietkerk M, Sugihara G. Early-warning signals for critical transitions. Nature 461 (7260, 2009):53-9; Christian Kuehn. A mathematical framework for critical transitions: normal forms, variance and applications. arXiv:1101.2908v1 math.DS]. Therefore, it may be generally possible to predict the imminence of pathological phase transitions such as the pathological attacks indicated above, using nonlinear as well as ad hoc analyses of relevant noninvasive ambulatory signals, obtained using ambulatory sensors such as those described in the previous paragraphs.

For many pathological attacks or transitions, it is known that vagal nerve stimulation is protective. Therefore, a patient who is promptly forewarned by the invention that such a pathological dynamical event is imminent may use noninvasive vagus nerve stimulation as a prophylactic countermeasure, with little risk of pain or adverse consequences, and with potentially much to gain by averting the onset or episode of the disease. According to the present invention, the prophylactic stimulation will ordinarily be performed in "open-loop" mode, wherein the sensors do not provide immediate feedback to determine the parameters of the stimulation (frequency, pulse width, number of pulses per burst, etc.). However, also according to the present invention, preliminary stimulations may be performed in "closed-loop" mode, wherein the sensors do provide feedback, in order to select the stimulation parameters that will eventually be used during the open-loop prophylactic stimulation. If preliminary parameter selection has not yet taken place, the prophylactic stimulation may also be performed in "closed-loop" feedback mode. Because the goal of the devices is to forecast an imminent event, feedforward methods are generally used in any case. Although the preferred stimulation methods are noninvasive, it is understood that invasive stimulation and data acquisition methods may also be used for a patient in whom electrodes have already been implanted. It is also understood that the noninvasive vagal nerve stimulation countermeasure may be used in conjunction with other countermeasures (e.g., inhaler or EpiPen for bronchoconstriction).

SUMMARY OF THE INVENTION

In one aspect of the invention, devices and methods are described to produce therapeutic effects in a patient by utilizing an energy source that transmits energy non-invasively to nervous tissue. In particular, the disclosed devices can transmit energy to, or in close proximity to, a vagus nerve in the neck of the patient, in order to temporarily stimulate, block and/or modulate electrophysiological signals in that nerve. The methods that are disclosed herein comprise stimulating a vagus nerve with particular stimulation waveform parameters, preferably using the nerve stimulator devices that are also described herein.

A novel stimulator device is used to modulate electrical activity of a vagus nerve or other nerves or tissue. The stimulator comprises a source of electrical power and two or more remote electrodes that are configured to stimulate a deep nerve relative to the nerve axis. The device also comprises continuous electrically conducting media with which the electrodes are in contact. The conducting medium is also in contact with an interface element that makes physical contact with the patient's skin. The interface element may be electrically insulating (dielectric) material, such as a sheet of Mylar, in which case electrical coupling of the device to the patient is capacitive. In other embodiments, the interface element is electrically conducting material, such as an electrically conducting or permeable membrane, in which case electrical coupling of the device to the patient is ohmic. The interface element may have a shape that conforms to the contour of a target body surface of a patient when the medium is applied to the target body surface. In another aspect of the invention, a non-invasive magnetic stimulator device is used to modulate electrical activity of the vagus nerve or other nerves or tissue, without actually introducing a magnetic field into the patient.

For the present medical applications, the electrode-based device or a magnetic stimulation device is ordinarily applied to the vicinity of the patient's neck. In one embodiment of the electrode-based invention, the stimulator comprises two electrodes that lie side-by-side within separate stimulator heads, wherein the electrodes are separated by electrically insulating material. Each electrode is in continuous contact with an electrically conducting medium that extends from the interface element of the stimulator to the electrode. The interface element also contacts the patient's skin when the device is in operation. The conducting media for different electrodes are also separated by electrically insulating material.

In another embodiment of the invention, a non-invasive magnetic stimulator device is ordinarily applied to the vicinity of the patient's neck. In a preferred embodiment of the magnetic stimulator, the stimulator comprises two toroidal windings that lie side-by-side within separate stimulator heads, wherein the toroidal windings are separated by electrically insulating material. Each toroid is in continuous contact with an electrically conducting medium that extends from the patient's skin to the toroid.

A source of power supplies a pulse of electric charge to the electrodes or magnetic stimulator coil, such that the electrodes or magnetic stimulator produce an electric current and/or an electric field within the patient. The electrical or magnetic stimulator is configured to induce a peak pulse voltage sufficient to produce an electric field in the vicinity of a nerve such as a vagus nerve, to cause the nerve to depolarize and reach a threshold for action potential propagation. By way of example, the threshold electric field for stimulation of the nerve may be about 8 V/m at 1000 Hz. For example, the device may produce an electric field within the patient of about 10 to 600 V/m and an electrical field gradient of greater than 2 V/m/mm.

Current passing through an electrode may be about 0 to 40 mA, with voltage across the electrodes of 0 to 30 volts. The current is passed through the electrodes in bursts of pulses. There may be 1 to 20 pulses per burst, preferably five pulses. Each pulse within a burst has a duration of 20 to 1000 microseconds, preferably 200 microseconds. A burst followed by a silent inter-burst interval repeats at 1 to 5000 bursts per second (bps), preferably at 15-50 bps. The preferred shape of each pulse is a full sinusoidal wave. The preferred stimulator shapes an elongated electric field of effect that can be oriented parallel to a long nerve, such as a vagus nerve in a patient's neck. By selecting a suitable waveform to stimulate the nerve, along with suitable parameters such as current, voltage, pulse width, pulses per burst, inter-burst interval, etc., the stimulator produces a correspondingly selective physiological response in an individual patient. Such a suitable waveform and parameters are simultaneously selected to avoid substantially stimulating nerves and tissue other than the target nerve, particularly avoiding the stimulation of nerves that produce pain.

The currents passing through the coils of the magnetic stimulator will saturate its core (e.g., 0.1 to 2 Tesla magnetic field strength for Supermendur core material). This will require approximately 0.5 to 20 amperes of current being passed through each coil, typically 2 amperes, with voltages across each coil of 10 to 100 volts. The current is passed through the coils in bursts of pulses as described above, shaping an elongated electrical field of effect as with the electrode-based stimulator.

The disclosure teaches methods for the forecasting of an imminent medical attack and using the disclosed stimulators to avert the attack. Teachings of the present invention demonstrate how to treat a patient, by positioning the disclosed noninvasive stimulator devices against body surfaces, particularly at a location in the vicinity of the patient's neck where a vagus nerve is located under the skin.

The stimulation is performed with a sinusoidal burst waveform as described above, followed by silent inter-burst period repeats itself with a period of T. For example, the sinusoidal period τ may be 200 microseconds; the number of pulses per burst may be N=5; and the whole pattern of burst followed by silent inter-burst period may have a period of T=40000 microseconds, which is comparable to 25 Hz stimulation.

More generally, there may be 1 to 20 pulses per burst, preferably five pulses. Each pulse within a burst has a duration of 20 to 1000 microseconds; preferably 200 microseconds. A burst followed by a silent inter-burst interval repeats at 1 to 5000 bursts per second (bps), preferably at 5 to 50 bps, more preferably 10 to 25 bps stimulation (comparable to 10-25 Hz), and even more preferably at 20 bps. Although the preferred shape of each pulse is a full sinusoidal wave, triangular or other shapes known in the art may be used as well. The stimulation is performed typically for 30 minutes. Treatment may be performed on the left or right or both vagus nerves, and it may be performed alternately on the left and right vagus nerves.

Forecasting and averting of an acute event is implemented within the context of control theory. A controller, comprising the disclosed vagus nerve stimulator, a PID, and a feedforward model, provides input to the physiological system that is to be controlled. Output from the system is monitored in a patient using sensors for physiological signals. Those signals may then be used to provide feedback to the controller.

In closed-loop mode, the controller and system are used to select parameters for the vagus nerve stimulation. Closed loop mode may also be used when the physiological system is non-stationary. Otherwise, the controller may be used to forecast the imminence of an acute event, and the vagus nerve stimulator is used in open loop mode to stimulate the patient, but using stimulator parameters that had been selected when the system was used in closed-loop mode.

Forecasting models may be grey-box models that incorporate knowledge of the physiological system's anatomy and mechanisms. Forecasting models may also be black box models, comprising autoregressive models as well as models that make use of principal components, Kalman filters, wavelet transforms, hidden Markov models, artificial neural networks, and/or support vector machines. In the preferred embodiments, support vector machines are used.

Methods are disclosed wherein an imminent asthma attack is averted by forecasting the attack and using noninvasive vagus nerve stimulation. A grey-box forecasting model involving coupled Duffing oscillators is disclosed. The model predicts the abrupt onset of asthma, which is described in terms of phase diagrams. Data used to fit parameters of the model include a those acquired by an environmental sensor as well as images of the lung acquired by electrical impedance tomography and acoustic imaging.

Methods are disclosed wherein an imminent epileptic seizure is averted by forecasting the attack and using noninvasive vagus nerve stimulation. Data used to forecast the seizure include those acquired by EEG measurement.

Methods are disclosed wherein an imminent migraine headache is averted by forecasting the headache and using noninvasive vagus nerve stimulation. Data used to forecast the migraine headache may include those acquired from sensors for stress, cardiovascular and respiratory sensors, transdermal reverse iontophoresis sensors, environmental sensors, and brain function sensors.

Methods are disclosed wherein an imminent transient ischemic attack (TIA) or a stroke is averted by forecasting the TIA or stroke and using noninvasive vagus nerve stimulation. Data used to forecast the TIA or stroke include those acquired using transcranial Doppler ultrasound.

Methods are disclosed wherein imminent atrial fibrillation is averted by forecasting the atrial fibrillation and using noninvasive vagus nerve stimulation. Data used to forecast the atrial fibrillation include those acquired from an electrocardiogram.

Methods are disclosed wherein an imminent myocardial infarction is averted by forecasting the myocardial infarction and using noninvasive vagus nerve stimulation. Data used to forecast the myocardial infarction include those acquired using radio-labeled probes and a vest containing a nuclear detector.

Methods are disclosed wherein imminent ventricular fibrillation or ventricular tachycardia is averted by forecasting the ventricular fibrillation or tachycardia and using noninvasive vagus nerve stimulation. Data used to forecast the ventricular fibrillation include those acquired from an electrocardiogram.

Methods are disclosed wherein an imminent panic attack is averted by forecasting the panic attack and using noninvasive vagus nerve stimulation. Data used to forecast the panic attack include sensors for stress, as well as cardiovascular and respiratory sensors.

Methods are disclosed wherein an imminent attack of depression is averted by forecasting the depression attack and using noninvasive vagus nerve stimulation. Data used to forecast the attack of depression include sensors for stress, as well as cardiovascular and respiratory sensors.

However, it should be understood that application of the methods and devices is not limited to the examples that are given. The novel systems, devices and methods for treating conditions using the disclosed stimulator or other noninvasive stimulation devices are more completely described in the following detailed description of the invention, with reference to the drawings provided herewith, and in claims appended hereto. Other aspects, features, advantages, etc. will become apparent to one skilled in the art when the description of the invention herein is taken in conjunction with the accompanying drawings.

INCORPORATION BY REFERENCE

Hereby, all issued patents, published patent applications, and non-patent publications that are mentioned in this specification are herein incorporated by reference in their entirety for all purposes, to the same extent as if each individual issued patent, published patent application, or non-patent publication were specifically and individually indicated to be incorporated by reference.

BRIEF DESCRIPTION OF THE DRAWINGS

For the purposes of illustrating the various aspects of the invention, there are shown in the drawings forms that are presently preferred, it being understood, however, that the invention is not limited by or to the precise data, methodologies, arrangements and instrumentalities shown, but rather only by the claims.

FIG. 1 is a schematic view of magnetic and electrode-based nerve or tissue modulating devices according to the present invention, which supply controlled pulses of electrical current to magnetic coils or to electrodes, respectively, each of which are continuously in contact with a volume filled with electrically conducting material, and wherein the conducting material is also in contact with an interface element that, in operation, contacts the patient's skin.

FIG. 2 illustrates an exemplary electrical voltage/current profile for a blocking and/or modulating impulses that are applied to a portion or portions of a nerve, in accordance with an embodiment of the present invention.

FIG. 3 illustrates a dual-electrode stimulator according to an embodiment of the present invention, which is shown to house the stimulator's electrodes and electronic components.

FIG. 9 illustrates a phase diagram according to the present invention, which circumscribes regions where coupled nonlinear oscillators within the lung exhibit qualitatively different types of dynamics, as the concentration environmental signals and cumulative magnitude of vagus nerve stimulations are varied.

DETAILED DESCRIPTION OF THE PREFERRED EMBODIMENTS

Figure 4E:
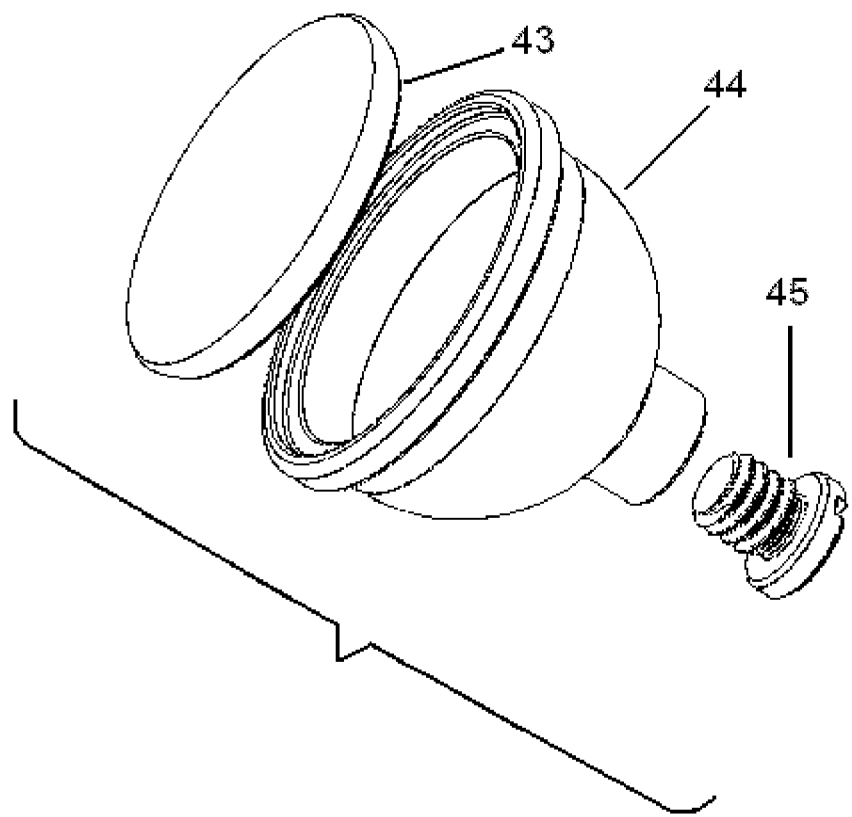
FIG. 4 illustrates preferred and alternate embodiments of the head of the dual-electrode stimulator that is shown in FIG. 3.

In the present invention, energy is transmitted non-invasively to a patient using novel electrode-based and/or magnetic stimulation devices that are designed to meet a long-felt but unsolved need to stimulate nerves electrically, totally non-invasively, selectively, and essentially without producing pain.

The invention is particularly useful for producing applied electrical impulses that interact with the signals of one or more nerves to achieve a therapeutic result. In particular, the present disclosure describes devices and methods to stimulate a vagus nerve non-invasively at a location in the neck, in order to avert an imminent medical attack.

Transcutaneous electrical stimulation with electrodes, as well as with magnetic stimulators, can be unpleasant or painful, in the experience of patients that undergo such procedures. The quality of sensation caused by stimulation depends strongly on current and frequency, such that currents barely greater than the perception threshold generally cause painless sensations described as tingle, itch, vibration, buzz, touch, pressure, or pinch, but higher currents can cause sharp or burning pain. As the depth of penetration of the stimulus under the skin is increased, any pain will generally begin or increase. Strategies to reduce the pain include: use of anesthetics placed on or injected into the skin near the stimulation and placement of foam pads on the skin at the site of stimulation [Jeffrey J. BORCKARDT, Arthur R. Smith, Kelby Hutcheson, Kevin Johnson, Ziad Nahas, Berry Anderson, M. Bret Schneider, Scott T. Reeves, and Mark S. George. Reducing Pain and Unpleasantness During Repetitive Transcranial Magnetic Stimulation. Journal of ECT 2006; 22:259-264], use of nerve blockades [V. HAKKINEN, H. Eskola, A. Yli-Hankala, T. Nurmikko and S. Kolehmainen. Which structures are sensitive to painful transcranial stimulation? Electromyogr. clin. Neurophysiol. 1995, 35:377-383], the use of very short stimulation pulses [V. SUIHKO. Modelling the response of scalp sensory receptors to transcranial electrical stimulation. Med. Biol. Eng. Comput., 2002, 40, 395-401], decreasing current density by increasing electrode size [Kristof VERHOEVEN and J. Gert van Dijk. Decreasing pain in electrical nerve stimulation. Clinical Neurophysiology 117 (2006) 972-978], using a high impedance electrode [N. SHA, L. P. J. Kenney, B. W. Heller, A. T. Barker, D. Howard and W. Wang. The effect of the impedance of a thin hydrogel electrode on sensation during functional electrical stimulation. Medical Engineering & Physics (2008): 739-746] and providing patients with the amount of information that suits their personalities [Anthony DELITTO, Michael J Strube, Arthur D Shulman, Scott D Minor. A Study of Discomfort with Electrical Stimulation. Phys. Ther. 1992; 72:410-424]. U.S. Pat. No. 7,614,996, entitled Reducing discomfort caused by electrical stimulation, to RIEHL discloses the application of a secondary stimulus to counteract what would otherwise be an uncomfortable primary stimulus. Other methods of reducing pain are intended to be used with invasive nerve stimulation [No. U.S. Pat. No. 7,904,176, entitled Techniques for reducing pain associated with nerve stimulation, to BEN-EZRA et al].

Additional considerations related to pain resulting from the stimulation are as follows. When stimulation is repeated over the course of multiple sessions, patients may adapt to the pain and exhibit progressively less discomfort. Patients may be heterogeneous with respect to their threshold for pain caused by stimulation, including heterogeneity related to gender and age. Electrical properties of an individual's skin vary from day to day and may be affected by cleaning, abrasion, and the application of various electrode gels and pastes. Skin properties may also be affected by the stimulation itself, as a function of the duration of stimulation, the recovery time between stimulation sessions, the transdermal voltage, the current density, and the power density. The application of multiple electrical pulses can result in different perception or pain thresholds and levels of sensation, depending on the spacing and rate at which pulses are applied. The separation distance between two electrodes determines whether sensations from the electrodes are separate, overlap, or merge. The limit for tolerable sensation is sometimes said to correspond to a current density of 0.5 mA/cm$^2$, but in reality the functional relationship between pain and current density is very complicated. Maximum local current density may be more important in producing pain than average current density, and local current density generally varies under an electrode, e.g., with greater current densities along edges of the electrode or at "hot spots." Furthermore, pain thresholds can have a thermal and/or electrochemical component, as well as a current density component. Pulse frequency plays a significant role in the perception of pain, with muscle contraction being involved at some frequencies and not others, and with the spatial extent of the pain sensation also being a function of frequency. The sensation is also a function of the waveform (square-wave, sinusoidal, trapezoidal, etc.), especially if pulses are less than a millisecond in duration [Mark R. PRAUSNITZ. The effects of electric current applied to skin: A review for transdermal drug delivery. Advanced Drug Delivery Reviews 18 (1996): 395-425].

Considering that there are so many variables that may influence the likelihood of pain during non-invasive electrical stimulation (detailed stimulus waveform, frequency, current density, electrode type and geometry, skin preparation, etc.), considering that these same variables must be simultaneously selected in order to independently produce a desired therapeutic outcome by nerve stimulation, and considering that one also wishes to selectively stimulate the nerve (e.g., avoid stimulating a nearby nerve), it is understandable that prior to the present disclosure, no one has described devices and methods for stimulating a nerve electrically, totally non-invasively, selectively, and without causing substantial pain.

Applicant discovered the disclosed electrode-based devices and methods in the course of experimentation with a magnetic stimulation device that was disclosed in Applicant's commonly assigned co-pending U.S. patent application Ser. No. 12/964,050, entitled Magnetic Stimulation Devices and Methods of Therapy, to SIMON et al. Thus, combined elements in the electrode-based invention do not merely perform the function that the elements perform separately (viz., perform therapeutic electrical stimulation or neuromodulation, minimize stimulation pain, or stimulate the nerve selectively), and one of ordinary skill in the art would not have combined the claimed elements by known methods because the archetypal magnetic stimulator was known only to Applicant. That stimulator used a magnetic coil, embedded in a safe and practical conducting medium that was in direct contact with arbitrarily-oriented patient's skin, which had not been described in its closest art [Rafael CARBUNARU and Dominique M. Durand. Toroidal coil models for transcutaneous magnetic stimulation of nerves. IEEE Transactions on Biomedical Engineering 48 (4, 2001): 434-441; Rafael Carbunaru FAIERSTEIN, Coil Designs for Localized and Efficient Magnetic Stimulation of the Nervous System. Ph.D. Dissertation, Department of Biomedical Engineering, Case Western Reserve, May, 1999. (UMI Microform Number: 9940153, UMI Company, Ann Arbor Mich.)]. Existing magnetic stimulators are complex and expensive, use high currents that overheat and limit the possible duration of stimulation, and can produce stimulation pain. In contrast to existing magnetic stimulators, the stimulator that was disclosed in Applicant's above-cited co-pending patent application is relatively simple to construct and operates with low currents. Furthermore, the device confines the magnetic field to within the device itself, so that magnetic fields to not'enter the patient's body. As a result, this design makes it possible to stimulate the patient's nerve over an extended period of time selectively and without producing pain.

FIG. 1A is a schematic diagram of Applicant's above-mentioned magnetic nerve stimulating/modulating device 301 for delivering impulses of energy to nerves for the treatment of medical conditions. As shown, device 301 may include an impulse generator 310; a power source 320 coupled to the impulse generator 310; a control unit 330 in communication with the impulse generator 310 and coupled to the power source 320; and a magnetic stimulator coil 341 coupled via wires to impulse generator coil 310. The stimulator coil 341 is toroidal in shape, due to its winding around a toroid of core material.

Although the magnetic stimulator coil 341 is shown in FIG. 1A to be a single coil, in practice the coil may also comprise two or more distinct coils, each of which is connected in series or in parallel to the impulse generator 310. Thus, the coil 341 that is shown in FIG. 1A represents all the magnetic stimulator coils of the device collectively. In a preferred embodiment that is discussed in connection with FIG. 5D below, coil 341 actually contains two coils that may be connected either in series or in parallel to the impulse generator 310.

The item labeled in FIG. 1A as 351 is a volume, surrounding the coil 341, that is filled with electrically conducting medium. As shown, the medium not only encloses the magnetic stimulator coil, but is also deformable such that it is form-fitting when applied to the surface of the body. Thus, the sinuousness or curvature shown at the outer surface of the electrically conducting medium 351 corresponds also to sinuousness or curvature on the surface of the body, against which the conducting medium 351 is applied, so as to make the medium and body surface contiguous. As time-varying electrical current is passed through the coil 341, a magnetic field is produced, but because the coil winding is toroidal, the magnetic field is spatially restricted to the interior of the toroid. An electric field and eddy currents are also produced. The electric field extends beyond the toroidal space and into the patient's body, causing electrical currents and stimulation within the patient. The volume 351 is electrically connected to the patient at a target skin surface in order to significantly reduce the current passed through the coil 341 that is needed to accomplish stimulation of the patient's nerve or tissue. In a preferred embodiment of the magnetic stimulator that is discussed below in connection with FIG. 5D, the conducting medium with which the coil 341 is in contact need not completely surround the toroid.

The design of the magnetic stimulator 301, which is adapted herein for use with surface electrodes, makes it possible to shape the electric field that is used to selectively stimulate a relatively deep nerve such as a vagus nerve in the patient's neck. Furthermore, the design produces significantly less pain or discomfort (if any) to a patient than stimulator devices that are currently known in the art. Conversely, for a given amount of pain or discomfort on the part of the patient (e.g., the threshold at which such discomfort or pain begins), the design achieves a greater depth of penetration of the stimulus under the skin.

FIG. 1B is a schematic diagram of an electrode-based nerve stimulating/modulating device 302 for delivering impulses of energy to nerves for the treatment of medical conditions. As shown, device 302 may include an impulse generator 310; a power source 320 coupled to the impulse generator 310; a control unit 330 in communication with the impulse generator 310 and coupled to the power source 320;

and electrodes 340 coupled via wires 345 to impulse generator 310. In a preferred embodiment, the same impulse generator 310, power source 320, and control unit 330 may be used for either the magnetic stimulator 301 or the electrode-based stimulator 302, allowing the user to change parameter settings depending on whether coils 341 or the electrodes 340 are attached.

Although a pair of electrodes 340 is shown in FIG. 1B, in practice the electrodes may also comprise three or more distinct electrode elements, each of which is connected in series or in parallel to the impulse generator 310. Thus, the electrodes 340 that are shown in FIG. 1B represent all electrodes of the device collectively.

The item labeled in FIG. 1B as 350 is a volume, contiguous with an electrode 340, that is filled with electrically conducting medium. As described below in connection with embodiments of the invention, conducting medium in which the electrode 340 is embedded need not completely surround an electrode. As also described below in connection with a preferred embodiment, the volume 350 is electrically connected to the patient at a target skin surface in order to shape the current density passed through an electrode 340 that is needed to accomplish stimulation of the patient's nerve or tissue. The electrical connection to the patient's skin surface is through an interface 351. In a preferred embodiment, the interface is made of an electrically insulating (dielectric) material, such as a thin sheet of Mylar. In that case, electrical coupling of the stimulator to the patient is capacitive. In other embodiments, the interface comprises electrically conducting material, such as the electrically conducting medium 350 itself, or an electrically conducting or permeable membrane. In that case, electrical coupling of the stimulator to the patient is ohmic. As shown, the interface may be deformable such that it is form-fitting when applied to the surface of the body. Thus, the sinuousness or curvature shown at the outer surface of the interface 351 corresponds also to sinuousness or curvature on the surface of the body, against which the interface 351 is applied, so as to make the interface and body surface contiguous.

The control unit 330 controls the impulse generator 310 to generate a signal for each of the device's coils or electrodes. The signals are selected to be suitable for amelioration of a particular medical condition, when the signals are applied non-invasively to a target nerve or tissue via the coil 341 or electrodes 340. It is noted that nerve stimulating/modulating device 301 or 302 may be referred to by its function as a pulse generator. Patent application publications US2005/0075701 and US2005/0075702, both to SHAFER, both of which are incorporated herein by reference, relating to stimulation of neurons of the sympathetic nervous system to attenuate an immune response, contain descriptions of pulse generators that may be applicable to the present invention. By way of example, a pulse generator is also commercially available, such as Agilent 33522A Function/Arbitrary Waveform Generator, Agilent Technologies, Inc., 5301 Stevens Creek Blvd Santa Clara Calif. 95051.

The control unit 330 may also comprise a general purpose computer, comprising one or more CPU, computer memories for the storage of executable computer programs (including the system's operating system) and the storage and retrieval of data, disk storage devices, communication devices (such as serial and USB ports) for accepting external signals from the system's keyboard and computer mouse as well as any externally supplied physiological signals (see FIG. 8), analog-to-digital converters for digitizing externally supplied analog signals (see FIG. 8), communication devices for the transmission and receipt of data to and from external devices such as printers and modems that comprise part of the system, hardware for generating the display of information on monitors that comprise part of the system, and busses to interconnect the above-mentioned components. Thus, the user may operate the system by typing instructions for the control unit 330 at a device such as a keyboard and view the results on a device such as the system's computer monitor, or direct the results to a printer, modem, and/or storage disk. Control of the system may be based upon feedback measured from externally supplied physiological or environmental signals. Alternatively, the control unit 330 may have a compact and simple structure, for example, wherein the user may operate the system using only an on/off switch and power control wheel or knob.

Parameters for the nerve or tissue stimulation include power level, frequency and train duration (or pulse number). The stimulation characteristics of each pulse, such as depth of penetration, strength and selectivity, depend on the rise time and peak electrical energy transferred to the electrodes or coils, as well as the spatial distribution of the electric field that is produced by the electrodes or coils. The rise time and peak energy are governed by the electrical characteristics of the stimulator and electrodes or coils, as well as by the anatomy of the region of current flow within the patient. In one embodiment of the invention, pulse parameters are set in such as way as to account for the detailed anatomy surrounding the nerve that is being stimulated [Bartosz SAWICKI, Robert Szmurlo, Przemyslaw Plonecki, Jacek Starzyński, Stanislaw Wincenciak, Andrzej Rysz. Mathematical Modelling of Vagus Nerve Stimulation. pp. 92-97 in: Krawczyk, A. Electromagnetic Field, Health and Environment: Proceedings of EHE'07. Amsterdam, IOS Press, 2008]. Pulses may be monophasic, biphasic or polyphasic. Embodiments of the invention include those that are fixed frequency, where each pulse in a train has the same interstimulus interval, and those that have modulated frequency, where the intervals between each pulse in a train can be varied.

FIG. 2A illustrates an exemplary electrical voltage/current profile for a stimulating, blocking and/or modulating impulse applied to a portion or portions of selected nerves in accordance with an embodiment of the present invention. For the preferred embodiment, the voltage and current refer to those that are non-invasively produced within the patient by the stimulator coils or electrodes. As shown, a suitable electrical voltage/current profile 400 for the blocking and/or modulating impulse 410 to the portion or portions of a nerve may be achieved using pulse generator 310. In a preferred embodiment, the pulse generator 310 may be implemented using a power source 320 and a control unit 330 having, for instance, a processor, a clock, a memory, etc., to produce a pulse train 420 to the coil 341 or electrodes 340 that deliver the stimulating, blocking and/or modulating impulse 410 to the nerve. Nerve stimulating/modulating device 301 or 302 may be externally powered and/or recharged may have its own power source 320. The parameters of the modulation signal 400, such as the frequency, amplitude, duty cycle, pulse width, pulse shape, etc., are preferably programmable. An external communication device may modify the pulse generator programming to improve treatment.

In addition, or as an alternative to the devices to implement the modulation unit for producing the electrical voltage/current profile of the stimulating, blocking and/or modulating impulse to the electrodes or coils, the device disclosed in patent publication No. US2005/0216062 (the entire disclosure of which is incorporated herein by reference) may be employed. That patent publication discloses a multifunctional electrical stimulation (ES) system adapted to yield output signals for effecting electromagnetic or other forms of electrical stimulation for a broad spectrum of different biological and biomedical applications, which produce an electric field pulse in order to non-invasively stimulate nerves. The system includes an ES signal stage having a selector coupled to a plurality of different signal generators, each producing a signal having a distinct shape, such as a sine wave, a square or a saw-tooth wave, or simple or complex pulse, the parameters of which are adjustable in regard to amplitude, duration, repetition rate and other variables. Examples of the signals that may be generated by such a system are described in a publication by LIBOFF [A. R. LIBOFF. Signal shapes in electromagnetic therapies: a primer. pp. 17-37 in: Bioelectromagnetic Medicine (Paul J. Rosch and Marko S. Markov, eds.). New York: Marcel Dekker (2004)]. The signal from the selected generator in the ES stage is fed to at least one output stage where it is processed to produce a high or low voltage or current output of a desired polarity whereby the output stage is capable of yielding an electrical stimulation signal appropriate for its intended application. Also included in the system is a measuring stage which measures and displays the electrical stimulation signal operating on the substance being treated as well as the outputs of various sensors which sense conditions prevailing in this substance whereby the user of the system can manually adjust it or have it automatically adjusted by feedback to provide an electrical stimulation signal of whatever type the user wishes, who can then observe the effect of this signal on a substance being treated.

The stimulating, blocking and/or modulating impulse signal 410 preferably has a frequency, an amplitude, a duty cycle, a pulse width, a pulse shape, etc. selected to influence the therapeutic result, namely, stimulating, blocking and/or modulating some or all of the transmission of the selected nerve. For example, the frequency may be about 1 Hz or greater, such as between about 15 Hz to 50 Hz, more preferably around 25 Hz. The modulation signal may have a pulse width selected to influence the therapeutic result, such as about 20 microseconds or greater, such as about 20 microseconds to about 1000 microseconds. For example, the electric field induced by the device within tissue in the vicinity of a nerve is 10 to 600 V/m, preferably around 300 V/m. The gradient of the electric field may be greater than 2 V/m/mm. More generally, the stimulation device produces an electric field in the vicinity of the nerve that is sufficient to cause the nerve to depolarize and reach a threshold for action potential propagation, which is approximately 8 V/m at 1000 Hz.

An objective of the disclosed stimulators is to provide both nerve fiber selectivity and spatial selectivity. Spatial selectivity may be achieved in part through the design of the electrode or coil configuration, and nerve fiber selectivity may be achieved in part through the design of the stimulus waveform, but designs for the two types of selectivity are intertwined. This is because, for example, a waveform may selectively stimulate only one of two nerves whether they lie close to one another or not, obviating the need to focus the stimulating signal onto only one of the nerves [GRILL W and Mortimer J T. Stimulus waveforms for selective neural stimulation. IEEE Eng. Med. Biol. 14 (1995): 375-385]. These methods complement others that are used to achieve selective nerve stimulation, such as the use of local anesthetic, application of pressure, inducement of ischemia, cooling, use of ultrasound, graded increases in stimulus intensity, exploiting the absolute refractory period of axons, and the application of stimulus blocks [John E. SWETT and Charles M. Bourassa. Electrical stimulation of peripheral nerve. In: Electrical Stimulation Research Techniques, Michael M. Patterson and Raymond P. Kesner, eds. Academic Press. (New York, 1981) pp. 243-295].

To date, the selection of stimulation waveform parameters for nerve stimulation has been highly empirical, in which the parameters are varied about some initially successful set of parameters, in an effort to find an improved set of parameters for each patient. A more efficient approach to selecting stimulation parameters might be to select a stimulation waveform that mimics electrical activity in the anatomical regions that one is attempting stimulate indirectly, in an effort to entrain the naturally occurring electrical waveform, as suggested in U.S. Pat. No. 6,234,953, entitled Electrotherapy device using low frequency magnetic pulses, to THOMAS et al. and application number US20090299435, entitled Systems and methods for enhancing or affecting neural stimulation efficiency and/or efficacy, to GLINER et al. One may also vary stimulation parameters iteratively, in search of an optimal setting [U.S. Pat. No. 7,869,885, entitled Threshold optimization for tissue stimulation therapy, to BEGNAUD et al]. However, some stimulation waveforms, such as those described herein, are discovered by trial and error, and then deliberately improved upon.

Invasive nerve stimulation typically uses square wave pulse signals. However, Applicant found that square waveforms are not ideal for non-invasive stimulation as they produce excessive pain. Prepulses and similar waveform modifications have been suggested as methods to improve selectivity of nerve stimulation waveforms, but Applicant did not find them ideal [Aleksandra VUCKOVIC, Marco Tosato and Johannes J Struijk. A comparative study of three techniques for diameter selective fiber activation in the vagal nerve: anodal block, depolarizing prepulses and slowly rising pulses. J. Neural Eng. 5 (2008): 275-286; Aleksandra VUCKOVIC, Nico J. M. Rijkhoff, and Johannes J. Struijk. Different Pulse Shapes to Obtain Small Fiber Selective Activation by Anodal Blocking—A Simulation Study. IEEE Transactions on Biomedical Engineering 51(5, 2004):698-706; Kristian HENNINGS. Selective Electrical Stimulation of Peripheral Nerve Fibers: Accommodation Based Methods. Ph.D. Thesis, Center for Sensory-Motor Interaction, Aalborg University, Aalborg, Denmark, 2004].

Applicant also found that stimulation waveforms consisting of bursts of square pulses are not ideal for non-invasive stimulation [M. I. JOHNSON, C. H. Ashton, D. R. Bousfield and J. W. Thompson. Analgesic effects of different pulse patterns of transcutaneous electrical nerve stimulation on cold-induced pain in normal subjects. Journal of Psychosomatic Research 35 (2/3, 1991):313-321; U.S. Pat. No. 7,734,340, entitled Stimulation design for neuromodulation, to De Ridder]. However, bursts of sinusoidal pulses are a preferred stimulation waveform, as shown in FIGS. 2B and 2C. As seen there, individual sinusoidal pulses have a period of $\tau$, and a burst consists of N such pulses. This is followed by a period with no signal (the inter-burst period). The pattern of a burst followed by silent inter-burst period repeats itself with a period of T. For example, the sinusoidal period $\tau$ may be 200 microseconds; the number of pulses per burst may be N=5; and the whole pattern of burst followed by silent inter-burst period may have a period of T=40000 microseconds (a much smaller value of T is shown in FIG. 2C to make the bursts discernable). When these exemplary values are used for T and $\tau$, the waveform contains significant Fourier components at higher frequencies ($1/200$ microseconds=5000/sec), as compared with those contained in transcutaneous nerve stimulation waveforms, as currently practiced.

Applicant is unaware of such a waveform having been used with therapeutic nerve stimulation, but a similar waveform has been used to stimulate muscle as a means of increasing muscle strength in elite athletes. However, for the muscle strengthening application, the currents used (200 mA) may be very painful and two orders of magnitude larger than what are disclosed herein. Furthermore, the signal used for muscle strengthening may be other than sinusoidal (e.g., triangular), and the parameters $\tau$, N, and T may also be dissimilar from the values exemplified above [A. DELITTO, M. Brown, M. J. Strube, S. J. Rose, and R. C. Lehman. Electrical stimulation of the quadriceps femoris in an elite weight lifter: a single subject experiment. Int J Sports Med 10(1989):187-191; Alex R WARD, Nataliya Shkuratova. Russian Electrical Stimulation: The Early Experiments. Physical Therapy 82 (10, 2002): 1019-1030; Yocheved LAUFER and Michal Elboim. Effect of Burst Frequency and Duration of Kilohertz-Frequency Alternating Currents and of Low-Frequency Pulsed Currents on Strength of Contraction, Muscle Fatigue, and Perceived Discomfort. Physical Therapy 88 (10, 2008):1167-1176; Alex R WARD. Electrical Stimulation Using Kilohertz-Frequency Alternating Current. Physical Therapy 89 (2, 2009):181-190; J. PETROFSKY, M. Laymon, M. Prowse, S. Gunda, and J. Batt. The transfer of current through skin and muscle during electrical stimulation with sine, square, Russian and interferential waveforms. Journal of Medical Engineering and Technology 33 (2, 2009): 170-181; U.S. Pat. No. 4,177,819, entitled Muscle stimulating apparatus, to KOFSKY et al]. Burst stimulation has also been disclosed in connection with implantable pulse generators, but wherein the bursting is characteristic of the neuronal firing pattern itself [U.S. Pat. No. 7,734,340 to DE RIDDER, entitled Stimulation design for neuromodulation; application US20110184486 to DE RIDDER, entitled Combination of tonic and burst stimulations to treat neurological disorders]. By way of example, the electric field shown in FIGS. 2B and 2C may have an $E_{max}$ value of 17 V/m, which is sufficient to stimulate the nerve but is significantly lower than the threshold needed to stimulate surrounding muscle.

A preferred embodiment of the electrode-based stimulator is shown in FIG. 3A. A cross-sectional view of the stimulator along its long axis is shown in FIG. 3B. As shown, the stimulator (30) comprises two heads (31) and a body (32) that joins them. Each head (31) contains a stimulating electrode. The body of the stimulator (32) contains the electronic components and battery (not shown) that are used to generate the signals that drive the electrodes, which are located behind the insulating board (33) that is shown in FIG. 3B. However, in other embodiments of the invention, the electronic components that generate the signals that are applied to the electrodes may be separate, but connected to the electrode head (31) using wires. Furthermore, other embodiments of the invention may contain a single such head or more than two heads.

Heads of the stimulator (31) are applied to a surface of the patient's body, during which time the stimulator may be held in place by straps or frames (not shown), or the stimulator may be held against the patient's body by hand. In either case, the level of stimulation power may be adjusted with a wheel (34) that also serves as an on/off switch. A light (35) is illuminated when power is being supplied to the stimulator. An optional cap may be provided to cover each of the stimulator heads (31), to protect the device when not in use, to avoid accidental stimulation, and to prevent material within the head from leaking or drying. Thus, in this embodiment of the invention, mechanical and electronic components of the stimulator (impulse generator, control unit, and power source) are compact, portable, and simple to operate.

Construction of different embodiments of the stimulator head is shown in more detail in FIG. 4. Referring now to the exploded view shown in FIG. 4A, the electrode head is assembled from a snap-on cap (41) that serves as a tambour for a dielectric or conducting membrane (42), a disc without fenestration (43) or alternatively with fenestration (43'), the head-cup (44), and the electrode which is also a screw (45). Two embodiments of the disc (43) are shown. The preferred embodiment (43) is a solid, ordinarily uniformly conducting disc (e.g., metal such as stainless steel), which is possibly flexible in some embodiments. An alternate embodiment of the disc (43') is also shown, which is a non-conducting (e.g., plastic) aperture screen that permits electrical current to pass through its apertures. The electrode (45, also 340 in FIG. 1) seen in each stimulator head has the shape of a screw that is flattened on its tip. Pointing of the tip would make the electrode more of a point source, such that the above-mentioned equations for the electrical potential may have a solution corresponding more closely to a far-field approximation. Rounding of the electrode surface or making the surface with another shape will likewise affect the boundary conditions. Completed assembly of the stimulator head is shown in FIG. 4B, which also shows how the head is attached to the body of the stimulator (47).

The membrane (42) ordinarily serves as the interface shown as 351 in FIG. 1. For example, the membrane (42) may be made of a dielectric (non-conducting) material, such as a thin sheet of Mylar (biaxially-oriented polyethylene terephthalate, also known as BoPET). In other embodiments, it may be made of conducting material, such as a sheet of Tecophlic material from Lubrizol Corporation, 29400 Lakeland Boulevard, Wickliffe, Ohio 44092. In one embodiment shown in FIG. 4A, apertures of the alternate disc (43') may be open, or they may be plugged with conducting material, for example, KM10T hydrogel from Katecho Inc., 4020 Gannett Ave., Des Moines Iowa 50321. If the apertures are so-plugged, and the membrane (42) is made of conducting material, the membrane becomes optional, and the plug serves as the interface 351 shown in FIG. 1.

The head-cup (44) is filled with conducting material (350 in FIG. 1), for example, SIGNAGEL Electrode Gel from Parker Laboratories, Inc., 286 Eldridge Rd., Fairfield N.J. 07004. The snap-on cap (41), aperture screen disc (43'), head-cup (44) and body of the stimulator are made of a non-conducting material, such as acrylonitrile butadiene styrene. The depth of the head-cup from its top surface to the electrode may be between one and six centimeters. The head-cup may have a different curvature than what is shown in FIG. 4, or it may be tubular or conical or have some other inner surface geometry that will affect the Neumann boundary conditions.

The alternate embodiment of the stimulator head that is shown in FIG. 4C also contains a snap-on cap (41), membrane (42) that is made of a dielectric or a conducting material, the head-cup (44), and the electrode which is also a screw (45). This alternate embodiment differs from the embodiment shown in FIGS. 4A and 4B in regard to the mechanical support that is provided to the membrane (42). Whereas the disc (43) or (43') had provided mechanical support to the membrane in the other embodiment, in the alternate embodiment a reinforcing ring (40) is provided to the membrane. That reinforcement ring rests on non-conducting struts (49) that are placed in the head-cup (44), and a non-conducting strut-ring (48) is placed within notches in the struts (49) to hold the struts in place. An advantage of the alternate embodiment is that without a disc (43) or (43'), current flow may be less restricted through the membrane (42), especially if the membrane is made of a conducting material. Furthermore, although the struts and strut-ring are made of non-conducting material in this alternate embodiment, the design may be adapted to position additional electrode or other conducting elements within the head-cup for other more specialized configurations of the stimulator head, the inclusion of which will influence the electric fields that are generated by the device. Completed assembly of the alternate stimulator head is shown in FIG. 4D, without showing its attachment to the body of the stimulator. In fact, it is possible to insert a lead under the head of the electrode (45), and many other methods of attaching the electrode to the signal-generating electronics of the stimulator are known in the art.

Figure 4F:
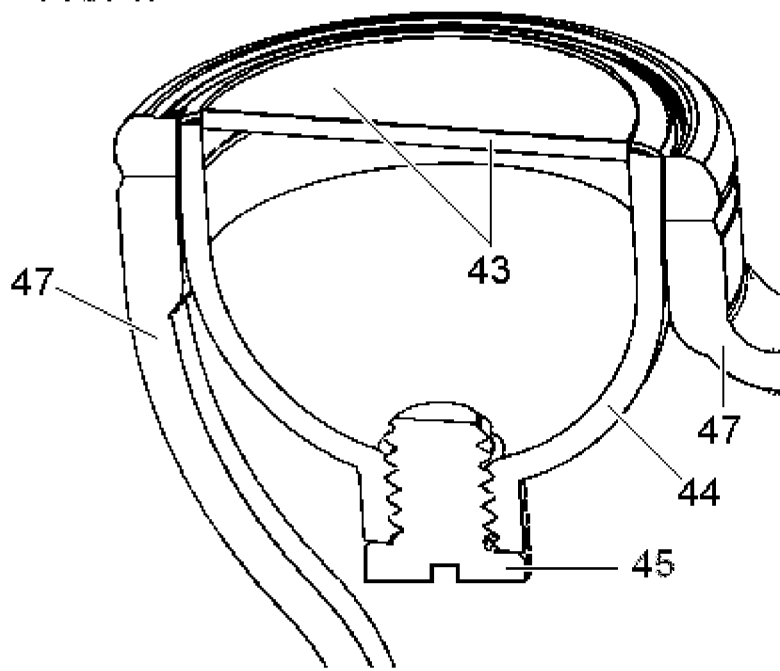

If the membrane (42) is made of conducting materials, and the disc (43) in FIG. 4A is made of solid conducting materials such as stainless steel, the membrane becomes optional, and the disc serves as the interface 351 shown in FIG. 1. Thus, an embodiment without the membrane is shown in FIGS. 4E and 4F. FIG. 4E shows that this version of the device comprises a solid (but possibly flexible in some embodiments) conducting disc that cannot absorb fluid (43), the non-conducting stimulator head (44) into or onto which the disc is placed, and the electrode (45), which is also a screw. It is understood that the disc (43) may have an anisotropic material or electrical structure, for example, wherein a disc of stainless steel has a grain, such that the grain of the disc should be rotated about its location on the stimulator head, in order to achieve optimal electrical stimulation of the patient. As seen in FIG. 4F, these items are assembled to become a sealed stimulator head that is attached to the body of the stimulator (47). The disc (43) may screw into the stimulator head (44), it may be attached to the head with adhesive, or it may be attached by other methods that are known in the art. The chamber of the stimulator head-cup is filled with a conducting gel, fluid, or paste, and because the disc (43) and electrode (45) are tightly sealed against the stimulator head-cup (44), the conducting material within the stimulator head cannot leak out.

In some embodiments, the interface and/or its underlying mechanical support comprise materials that will also provide a substantial or complete seal of the interior of the device. This inhibits any leakage of conducting material, such as gel, from the interior of the device and also inhibits any fluids from entering the device. In addition, this feature allows the user to easily clean the outer surface of the device (e.g., with isopropyl alcohol or similar disinfectant), avoiding potential contamination during subsequent uses of the device.

In some embodiments, the interface comprises a fluid permeable material that allows for passage of current through the permeable portions of the material. In these embodiments, a conductive medium (such as a gel) is preferably situated between the electrode(s) and the permeable interface. The conductive medium provides a conductive pathway for electrons to pass through the permeable interface to the outer surface of the interface and to the patient's skin.

In other embodiments of the present invention, the interface (351 in FIG. 1, or 42 in FIG. 4) is made from a very thin material with a high dielectric constant, such as material used to make capacitors. For example, it may be Mylar having a submicron thickness (preferably in the range 0.5 to 1.5 microns) having a dielectric constant of about 3. Because one side of Mylar is slick, and the other side is microscopically rough, the present invention contemplates two different configurations: one in which the slick side is oriented towards the patient's skin, and the other in which the rough side is so-oriented. Thus, at stimulation Fourier frequencies of several kilohertz or greater, the dielectric interface will capacitively couple the signal through itself, because it will have an impedance comparable to that of the skin. Thus, the dielectric interface will isolate the stimulator's electrode from the tissue, yet allow current to pass. In a preferred embodiment of the present invention, non-invasive electrical stimulation of a nerve is accomplished essentially substantially capacitively, which reduces the amount of ohmic stimulation, thereby reducing the sensation the patient feels on the tissue surface. This would correspond to a situation, for example, in which at least 30%, preferably at least 50%, of the energy stimulating the nerve comes from capacitive coupling through the stimulator interface, rather than from ohmic coupling. In other words, a substantial portion (e.g., 50%) of the voltage drop is across the dielectric interface, while the remaining portion is through the tissue.

The selection of the material for the dielectric constant involves at least two important variables: (1) the thickness of the interface; and (2) the dielectric constant of the material. The thinner the interface and/or the higher the dielectric constant of the material, the lower the voltage drop across the dielectric interface (and thus the lower the driving voltage required). For example, with Mylar, the thickness could be about 0.5 to 5 microns (preferably about 1 micron) with a dielectric constant of about 3. For a piezoelectric material like barium titanate or PZT (lead zirconate titanate), the thickness could be about 100-400 microns (preferably about 200 microns or 0.2 mm) because the dielectric constant is >1000.

One of the novelties of the embodiment that is a non-invasive capacitive stimulator (hereinafter referred to more generally as a capacitive electrode) arises in that it uses a low voltage (generally less than 100 volt) power source, which is made possible by the use of a suitable stimulation waveform, such as the waveform that is disclosed herein (FIGS. 2B and 2C). In addition, the capacitive electrode allows for the use of an interface that provides a more adequate seal of the interior of the device. The capacitive electrode may be used by applying a small amount of conductive material (e.g., conductive gel as described above) to its outer surface. In some embodiments, it may also be used by contacting dry skin, thereby avoiding the inconvenience of applying an electrode gel, paste, or other electrolytic material to the patient's skin and avoiding the problems associated with the drying of electrode pastes and gels. Such a dry electrode would be particularly suitable for use with a patient who exhibits dermatitis after the electrode gel is placed in contact with the skin [Ralph J. COSKEY. Contact dermatitis caused by ECG electrode jelly. Arch Dermatol 113(1977): 839-840]. The capacitive electrode may also be used to contact skin that has been wetted (e.g., with tap water or a more conventional electrolyte material) to make the electrode-skin contact (here the dielectric constant) more uniform [A L ALEXELONESCU, G Barbero, F C M Freire, and R Merletti. Effect of composition on the dielectric properties of hydrogels for biomedical applications. Physiol. Meas. 31 (2010) S169-S182].

As described below, capacitive biomedical electrodes are known in the art, but when used to stimulate a nerve noninvasively, a high voltage power supply is currently used to perform the stimulation. Otherwise, prior use of capacitive biomedical electrodes has been limited to invasive, implanted applications; to non-invasive applications that involve monitoring or recording of a signal, but not stimulation of tissue; to non-invasive applications that involve the stimulation of something other than a nerve (e.g., tumor); or as the dispersive electrode in electrosurgery.

Evidence of a long-felt but unsolved need, and evidence of failure of others to solve the problem that is solved by the this embodiment of the present invention (low-voltage, non-invasive capacitive stimulation of a nerve), is provided by KELLER and Kuhn, who review the previous high-voltage capacitive stimulating electrode of GEODE'S et al and write that "Capacitive stimulation would be a preferred way of activating muscle nerves and fibers, when the inherent danger of high voltage breakdowns of the dielectric material can be eliminated. Goal of future research could be the development of improved and ultra-thin dielectric foils, such that the high stimulation voltage can be lowered." [L. A. GEDDES, M. Hinds, and K. S. Foster. Stimulation with capacitor electrodes. Medical and Biological Engineering and Computing 25(1987): 359-360; Thierry KELLER and Andreas Kuhn. Electrodes for transcutaneous (surface) electrical stimulation. Journal of Automatic Control, University of Belgrade 18(2, 2008):35-45, on page 39]. It is understood that in the United States, according to the 2005 National Electrical Code, high voltage is any voltage over 600 volts. U.S. Pat. No. 3,077,884, entitled Electro-physiotherapy apparatus, to BARTROW et al, U.S. Pat. No. 4,144,893, entitled Neuromuscular therapy device, to HICKEY and U.S. Pat. No. 7,933,648, entitled High voltage transcutaneous electrical stimulation device and method, to TANRISEVER, also describe high voltage capacitive stimulation electrodes. U.S. Pat. No. 7,904,180, entitled Capacitive medical electrode, to JUOLA et al, describes a capacitive electrode that includes transcutaneous nerve stimulation as one intended application, but that patent does not describe stimulation voltages or stimulation waveforms and frequencies that are to be used for the transcutaneous stimulation. U.S. Pat. No. 7,715,921, entitled Electrodes for applying an electric field in-vivo over an extended period of time, to PALTI, and U.S. Pat. No. 7,805,201, entitled Treating a tumor or the like with an electric field, to PALTI, also describe capacitive stimulation electrodes, but they are intended for the treatment of tumors, do not disclose uses involving nerves, and teach stimulation frequencies in the range of 50 kHz to about 500 kHz.

This embodiment of the present invention uses a different method to lower the high stimulation voltage than developing ultra-thin dielectric foils, namely, to use a suitable stimulation waveform, such as the waveform that is disclosed herein (FIGS. 2B and 2C). That waveform has significant Fourier components at higher frequencies than waveforms used for transcutaneous nerve stimulation as currently practiced. Thus, one of ordinary skill in the art would not have combined the claimed elements, because transcutaneous nerve stimulation is performed with waveforms having significant Fourier components only at lower frequencies, and noninvasive capacitive nerve stimulation is performed at higher voltages. In fact, the elements in combination do not merely perform the function that each element performs separately. The dielectric material alone may be placed in contact with the skin in order to perform pasteless or dry stimulation, with a more uniform current density than is associated with ohmic stimulation, albeit with high stimulation voltages [L. A. GEDDES, M. Hinds, and K. S. Foster. Stimulation with capacitor electrodes. Medical and Biological Engineering and Computing 25(1987): 359-360; Yongmin KIM, H. Gunter Zieber, and Frank A. Yang. Uniformity of current density under stimulating electrodes. Critical Reviews in Biomedical Engineering 17(1990, 6): 585-619]. With regard to the waveform element, a waveform that has significant Fourier components at higher frequencies than waveforms currently used for transcutaneous nerve stimulation may be used to selectively stimulate a deep nerve and avoid stimulating other nerves, as disclosed herein for both noncapacitive and capacitive electrodes. But it is the combination of the two elements (dielectric interface and waveform) that makes it possible to stimulate a nerve capacitively without using the high stimulation voltage as is currently practiced.

Another embodiment of the electrode-based stimulator is shown in FIG. 5, showing a device in which electrically conducting material is dispensed from the device to the patient's skin. In this embodiment, the interface (351 in FIG. 1) is the conducting material itself. FIGS. 5A and 5B respectively provide top and bottom views of the outer surface of the electrical stimulator 50. FIG. 5C provides a bottom view of the stimulator 50, after sectioning along its long axis to reveal the inside of the stimulator.

Figure 5A:
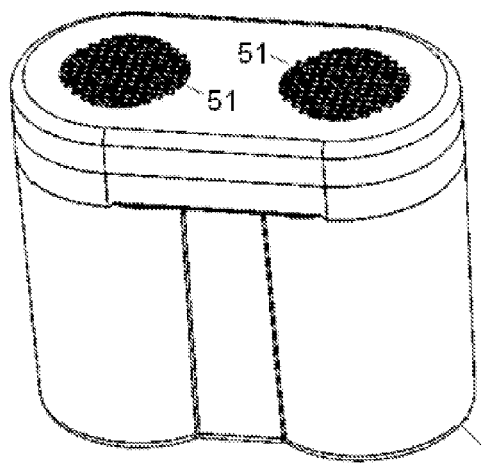
FIG. 5 illustrates an alternate embodiment of the dual-electrode stimulator, also comparing it with an embodiment of the magnetic stimulator according to the present invention.
Figure 5B:
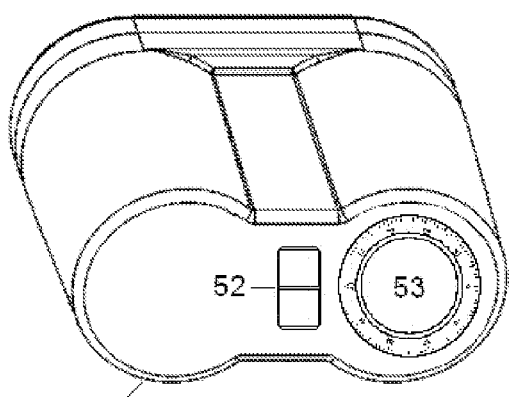
Figure 5C:
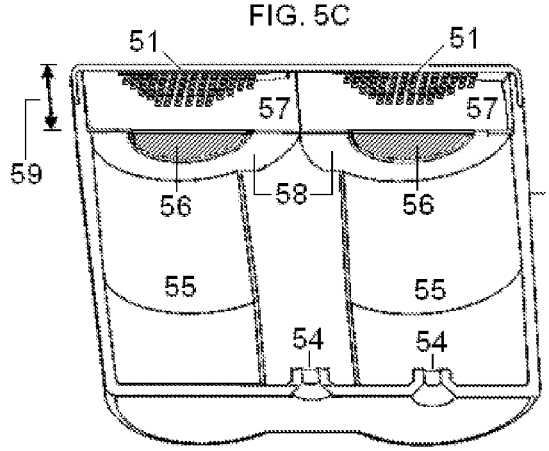

FIGS. 5A and 5C show a mesh 51 with openings that permit a conducting gel to pass from inside of the stimulator to the surface of the patient's skin at the position of nerve or tissue stimulation. Thus, the mesh with openings 51 is the part of the stimulator that is applied to the skin of the patient, through which conducting material may be dispensed. In any given stimulator, the distance between the two mesh openings 51 in FIG. 5A is constant, but it is understood that different stimulators may be built with different inter-mesh distances, in order to accommodate the anatomy and physiology of individual patients. Alternatively, the inter-mesh distance may be made variable as in the eyepieces of a pair of binoculars. A covering cap (not shown) is also provided to fit snugly over the top of the stimulator housing and the mesh openings 51, in order to keep the housing's conducting medium from leaking or drying when the device is not in use.

FIGS. 5B and 5C show the bottom of the self-contained stimulator 50. An on/off switch 52 is attached through a port 54, and a power-level controller 53 is attached through another port 54. The switch is connected to a battery power source (320 in FIG. 1B), and the power-level controller is attached to the control unit (330 in FIG. 1B) of the device. The power source battery and power-level controller, as well as the impulse generator (310 in FIG. 1B) are located (but not shown) in the rear compartment 55 of the housing of the stimulator 50.

Individual wires (not shown) connect the impulse generator (310 in FIG. 1B) to the stimulator's electrodes 56. The two electrodes 56 are shown here to be elliptical metal discs situated between the head compartment 57 and rear compartment 55 of the stimulator 50. A partition 58 separates each of the two head compartments 57 from one another and from the single rear compartment 55. Each partition 58 also holds its corresponding electrode in place. However, each electrode 56 may be removed to add electrically conducting gel (350 in FIG. 1B) to each head compartment 57. An optional non-conducting variable-aperture iris diaphragm may be placed in front of each of the electrodes within the head compartment 57, in order to vary the effective surface area of each of the electrodes. Each partition 58 may also slide towards the head of the device in order to dispense conducting gel through the mesh apertures 51. The position of each partition 58 therefore determines the distance 59 between its electrode 56 and mesh openings 51, which is variable in order to obtain the optimally uniform current density through the mesh openings 51. The outside housing of the stimulator 50, as well as each head compartment 57 housing and its partition 58, are made of electrically insulating material, such as acrylonitrile butadiene styrene, so that the two head compartments are electrically insulated from one another. Although the embodiment in FIG. 5 is shown to be a non-capacitive stimulator, it is understood that it may be converted into a capacitive stimulator by replacing the mesh openings 51 with a dielectric material, such as a sheet of Mylar, or by covering the mesh openings 51 with a sheet of such dielectric material.

In a preferred embodiment, the magnetic stimulator coil 341 in FIG. 1A has a body that is similar to the electrode-based stimulator shown in FIG. 5C. To compare the electrode-based stimulator with the magnetic stimulator, refer to FIG. 5D, which shows the magnetic stimulator 530 sectioned along its long axis to reveal its inner structure. As described below, it reduces the volume of conducting material that must surround a toroidal coil, by using two toroids, side-by-side, and passing electrical current through the two toroidal coils in opposite directions. In this configuration, the induced electrical current will flow from the lumen of one toroid, through the tissue and back through the lumen of the other, completing the circuit within the toroids' conducting medium. Thus, minimal space for the conducting medium is required around the outside of the toroids at positions near from the gap between the pair of coils. An additional advantage of using two toroids in this configuration is that this design will greatly increase the magnitude of the electric field gradient between them, which is crucial for exciting long, straight axons such as the vagus nerve and certain peripheral nerves.

Figure 5D:
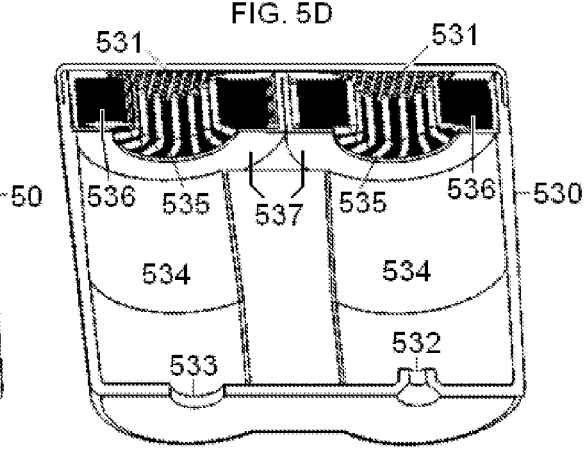

As seen in FIG. 5D, a mesh 531 has openings that permit a conducting gel (within 351 in FIG. 1A) to pass from the inside of the stimulator to the surface of the patient's skin at the location of nerve or tissue stimulation. Thus, the mesh with openings 531 is the part of the magnetic stimulator that is applied to the skin of the patient.

FIG. 5D also shows openings at the opposite end of the magnetic stimulator 530. One of the openings is an electronics port 532 through which wires pass from the stimulator coil(s) to the impulse generator (310 in FIG. 1A). The second opening is a conducting gel port 533 through which conducting gel (351 in FIG. 1A) may be introduced into the magnetic stimulator 530 and through which a screw-driven piston arm may be introduced to dispense conducting gel through the mesh 531. The gel itself is contained within cylindrical-shaped but interconnected conducting medium chambers 534 that are shown in FIG. 5D. The depth of the conducting medium chambers 534, which is approximately the height of the long axis of the stimulator, affects the magnitude of the electric fields and currents that are induced by the magnetic stimulator device [Rafael CARBUNARU and Dominique M. Durand. Toroidal coil models for transcutaneous magnetic stimulation of nerves. IEEE Transactions on Biomedical Engineering. 48 (4, 2001): 434-441].

FIG. 5D also show the coils of wire 535 that are wound around toroidal cores 536, consisting of high-permeability material (e.g., Supermendur). Lead wires (not shown) for the coils 535 pass from the stimulator coil(s) to the impulse generator (310 in FIG. 1A) via the electronics port 532. Different circuit configurations are contemplated. If separate lead wires for each of the coils 535 connect to the impulse generator (i.e., parallel connection), and if the pair of coils are wound with the same handedness around the cores, then the design is for current to pass in opposite directions through the two coils. On the other hand, if the coils are wound with opposite handedness around the cores, then the lead wires for the coils may be connected in series to the impulse generator, or if they are connected to the impulse generator in parallel, then the design is for current to pass in the same direction through both coils.

As also seen in FIG. 5D, the coils 535 and cores 536 around which they are wound are mounted as close as practical to the corresponding mesh 531 with openings through which conducting gel passes to the surface of the patient's skin. As shown, each coil and the core around which it is wound is mounted in its own housing 537, the function of which is to provide mechanical support to the coil and core, as well as to electrically insulate a coil from its neighboring coil. With this design, induced current will flow from the lumen of one toroid, through the tissue and back through the lumen of the other, completing the circuit within the toroids' conducting medium. A difference between the structure of the electrode-based stimulator shown in FIG. 5C and the magnetic stimulator shown in FIG. 5D is that the conducting gel is maintained within the chambers 57 of the electrode-based stimulator, which is generally closed on the back side of the chamber because of the presence of the electrode 56; but in the magnetic stimulator, the hole of each toroidal core and winding is open, permitting the conducting gel to enter the interconnected chambers 534.

Different diameter toroidal coils and windings may be preferred for different applications. For a generic application, the outer diameter of the core may be typically 1 to 5 cm, with an inner diameter typically 0.5 to 0.75 of the outer diameter. The coil's winding around the core may be typically 3 to 250 in number, depending on the core diameter and depending on the desired coil inductance. The currents passing through the coils of the magnetic stimulator will saturate the core (e.g., 0.1 to 2 Tesla magnetic field strength for Supermendur core material). This will require approximately 0.5 to 20 amperes of current being passed through each coil, typically 2 amperes, with voltages across each coil of 10 to 100 volts. The current is passed through the coils in bursts of pulses, as described in connection with FIG. 2. Additional disclosure of the magnetic stimulator shown in FIG. 1A is provided in Applicant's commonly assigned co-pending U.S. patent application Ser. No. 12/964,050 entitled Magnetic Stimulation Devices and Methods of Therapy, to SIMON et al., which is hereby incorporated by reference for all purposes.

In preferred embodiments of the electrode-based stimulator shown in FIG. 1B, electrodes are made of a metal, such as stainless steel, platinum, or a platinum-iridium alloy. However, in other embodiments, the electrodes may have many other sizes and shapes, and they may be made of other materials [Thierry KELLER and Andreas Kuhn. Electrodes for transcutaneous (surface) electrical stimulation. Journal of Automatic Control, University of Belgrade, 18(2, 2008): 35-45; G. M. LYONS, G. E. Leane, M. Clarke-Moloney, J. V. O'Brien, P. A. Grace. An investigation of the effect of electrode size and electrode location on comfort during stimulation of the gastrocnemius muscle. Medical Engineering & Physics 26 (2004) 873-878; Bonnie J. FORRESTER and Jerrold S. Petrofsky. Effect of Electrode Size, Shape, and Placement During Electrical Stimulation. The Journal of Applied Research 4, (2, 2004):346-354; Gad ALON, Gideon Kantor and Henry S. Ho. Effects of Electrode Size on Basic Excitatory Responses and on Selected Stimulus Parameters. Journal of Orthopaedic and Sports Physical Therapy. 20(1, 1994):29-35].

For example, there may be more than two electrodes; the electrodes may comprise multiple concentric rings; and the electrodes may be disc-shaped or have a non-planar geometry. They may be made of other metals or resistive materials such as silicon-rubber impregnated with carbon that have different conductive properties [Stuart F. COGAN. Neural Stimulation and Recording Electrodes. Annu. Rev. Biomed. Eng. 2008. 10:275-309; Michael F. NOLAN. Conductive differences in electrodes used with transcutaneous electrical nerve stimulation devices. Physical Therapy 71(1991):746-751].

Although the electrode may consist of arrays of conducting material, the embodiments shown in FIGS. 3 to 5 avoid the complexity and expense of array or grid electrodes [Ana POPOVIC-BIJELIC, Goran Bijelic, Nikola Jorgovanovic, Dubravka Bojanic, Mirjana B. Popovic, and Dejan B. Popovic. Multi-Field Surface Electrode for Selective Electrical Stimulation. Artificial Organs 29 (6, 2005):448-452; Dejan B. POPOVIC and Mirjana B. Popovic. Automatic determination of the optimal shape of a surface electrode: Selective stimulation. Journal of Neuroscience Methods 178 (2009) 174-181; Thierry KELLER, Marc Lawrence, Andreas Kuhn, and Manfred Morari. New Multi-Channel Transcutaneous Electrical Stimulation Technology for Rehabilitation. Proceedings of the 28th IEEE EMBS Annual International Conference New York City, USA, Aug. 30-Sep. 3, 2006 (WeC14.5): 194-197]. This is because the designs shown in FIGS. 3 to 5 provide a uniform surface current density, which would otherwise be a potential advantage of electrode arrays, and which is a trait that is not shared by most electrode designs [Kenneth R. BRENNEN. The Characterization of Transcutaneous Stimulating Electrodes. IEEE Transactions on Biomedical Engineering BME-23 (4, 1976): 337-340; Andrei PATRICIU, Ken Yoshida, Johannes J. Struijk, Tim P. DeMonte, Michael L. G. Joy, and Hans Stdkilde-Jrgensen. Current Density Imaging and Electrically Induced Skin Burns Under Surface Electrodes. IEEE Transactions on Biomedical Engineering 52 (12, 2005): 2024-2031; R. H. GEUZE. Two methods for homogeneous field defibrillation and stimulation. Med. and Biol. Eng. and Comput. 21(1983), 518-520; J. PETROFSKY, E. Schwab, M. Cuneo, J. George, J. Kim, A. Almalty, D. Lawson, E. Johnson and W. Remigo. Current distribution under electrodes in relation to stimulation current and skin blood flow: are modern electrodes really providing the current distribution during stimulation we believe they are? Journal of Medical Engineering and Technology 30 (6, 2006): 368-381; Russell G. MAUS, Erin M. McDonald, and R. Mark Wightman. Imaging of Nonuniform Current Density at Microelectrodes by Electrogenerated Chemiluminescence. Anal. Chem. 71(1999): 4944-4950]. In fact, patients found the design shown in FIGS. 3 to 5 to be less painful in a direct comparison with a commercially available grid-pattern electrode [UltraStim grid-pattern electrode, Axelggard Manufacturing Company, 520 Industrial Way, Fallbrook Calif., 2011]. The embodiment of the electrode that uses capacitive coupling is particularly suited to the generation of uniform stimulation currents [Yongmin KIM, H. Gunter Zieber, and Frank A. Yang. Uniformity of current density under stimulating electrodes. Critical Reviews in Biomedical Engineering 17(1990, 6): 585-619].

The electrode-based stimulator designs shown in FIGS. 3 to 5 situate the electrode remotely from the surface of the skin within a chamber, with conducting material placed in the chamber between the skin and electrode. Such a chamber design had been used prior to the availability of flexible, flat, disposable electrodes [U.S. Pat. No. 3,659,614, entitled Adjustable headband carrying electrodes for electrically stimulating the facial and mandibular nerves, to Jankelson; U.S. Pat. No. 3,590,810, entitled Biomedical body electrode, to Kopecky; U.S. Pat. No. 3,279,468, entitled Electrotherapeutic facial mask apparatus, to Le Vine; U.S. Pat. No. 6,757,556, entitled Electrode sensor, to Gopinathan et al; U.S. Pat. No. 4,383,529, entitled Iontophoretic electrode device method and gel insert, to Webster; U.S. Pat. No. 4,220,159, entitled Electrode, to Francis et al. U.S. Pat. No. 3,862,633, U.S. Pat. No. 4,182,346, and U.S. Pat. No. 3,973,557, entitled Electrode, to Allison et al; U.S. Pat. No. 4,215,696, entitled Biomedical electrode with pressurized skin contact, to Bremer et al; and U.S. Pat. No. 4,166,457, entitled Fluid self-sealing. bioelectrode, to Jacobsen et al.] The stimulator designs shown in FIGS. 3 to 5 are also self-contained units, housing the electrodes, signal electronics, and power supply. Portable stimulators are also known in the art, for example, U.S. Pat. No. 7,171,266, entitled Electro-acupuncture device with stimulation electrode assembly, to Gruzdowich. One of the novelties of the designs shown in FIGS. 3 to 5 is that the stimulator, along with a correspondingly suitable stimulation waveform, shapes the electric field, producing a selective physiological response by stimulating that nerve, but avoiding substantial stimulation of nerves and tissue other than the target nerve, particularly avoiding the stimulation of nerves that produce pain.

Examples in the remaining disclosure will be directed to methods for using the disclosed electrode-based and magnetic stimulation devices for treating a patient, particularly methods for detecting an imminent adverse event and using the stimulation devices to avert the onset of that event. The examples involve stimulating the patient on the surface of the patient's neck in order to stimulate one or both of the patient's vagus nerves. However, it will be appreciated that the systems and methods of the present invention might be applied equally well to other nerves of the body, including but not limited to parasympathetic nerves, sympathetic nerves, and spinal or cranial nerves. For example, the disclosed devices may used to treat particular medical conditions or avert medical conditions, comprising not only those described below and those described in the related applications cited in the section CROSS REFERENCE TO RELATED APPLICATIONS, but also other disorders in which a patient's symptoms may appear abruptly.

Selected nerve fibers are stimulated in different embodiments of methods that make use of the disclosed electrical stimulation devices, including stimulation of the vagus nerve at a location in the patient's neck. At that location, the vagus nerve is situated within the carotid sheath, near the carotid artery and the interior jugular vein. The carotid sheath is located at the lateral boundary of the retopharyngeal space on each side of the neck and deep to the sternocleidomastoid muscle. The left vagus nerve is sometimes selected for stimulation because stimulation of the right vagus nerve may produce undesired effects on the heart, but depending on the application, the right vagus nerve or both right and left vagus nerves may be stimulated instead.

The three major structures within the carotid sheath are the common carotid artery, the internal jugular vein and the vagus nerve. The carotid artery lies medial to the internal jugular vein, and the vagus nerve is situated posteriorly between the two vessels. Typically, the location of the carotid sheath or interior jugular vein in a patient (and therefore the location of the vagus nerve) will be ascertained in any manner known in the art, e.g., by feel or ultrasound imaging. Proceeding from the skin of the neck above the sternocleidomastoid muscle to the vagus nerve, a line may pass successively through the sternocleidomastoid muscle, the carotid sheath and the internal jugular vein, unless the position on the skin is immediately to either side of the external jugular vein. In the latter case, the line may pass successively through only the sternocleidomastoid muscle and the carotid sheath before encountering the vagus nerve, missing the interior jugular vein. Accordingly, a point on the neck adjacent to the external jugular vein might be preferred for non-invasive stimulation of the vagus nerve. The magnetic stimulator coil may be centered on such a point, at the level of about the fifth to sixth cervical vertebra.

Figure 6:
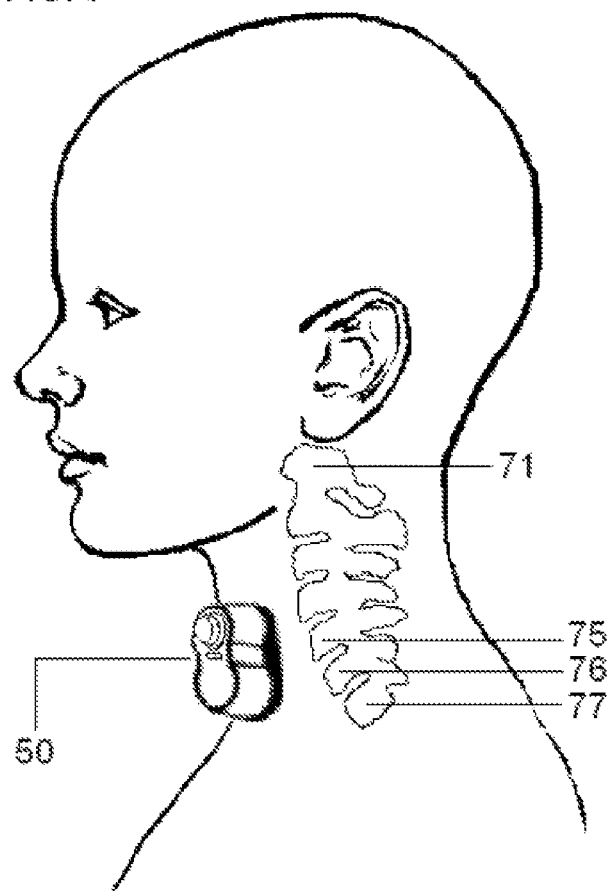
FIG. 6 illustrates the approximate position of the housing of the dual-electrode stimulator according one embodiment of the present invention, when the electrodes used to stimulate the vagus nerve in the neck of a patient.

FIG. 6 illustrates use of the devices shown in FIGS. 3 to 5 to stimulate the vagus nerve at that location in the neck, in which the stimulator device 50 in FIG. 5 is shown to be applied to the target location on the patient's neck as described above. For reference, locations of the following vertebrae are also shown: first cervical vertebra 71, the fifth cervical vertebra 75, the sixth cervical vertebra 76, and the seventh cervical vertebra 77.

Figure 7:
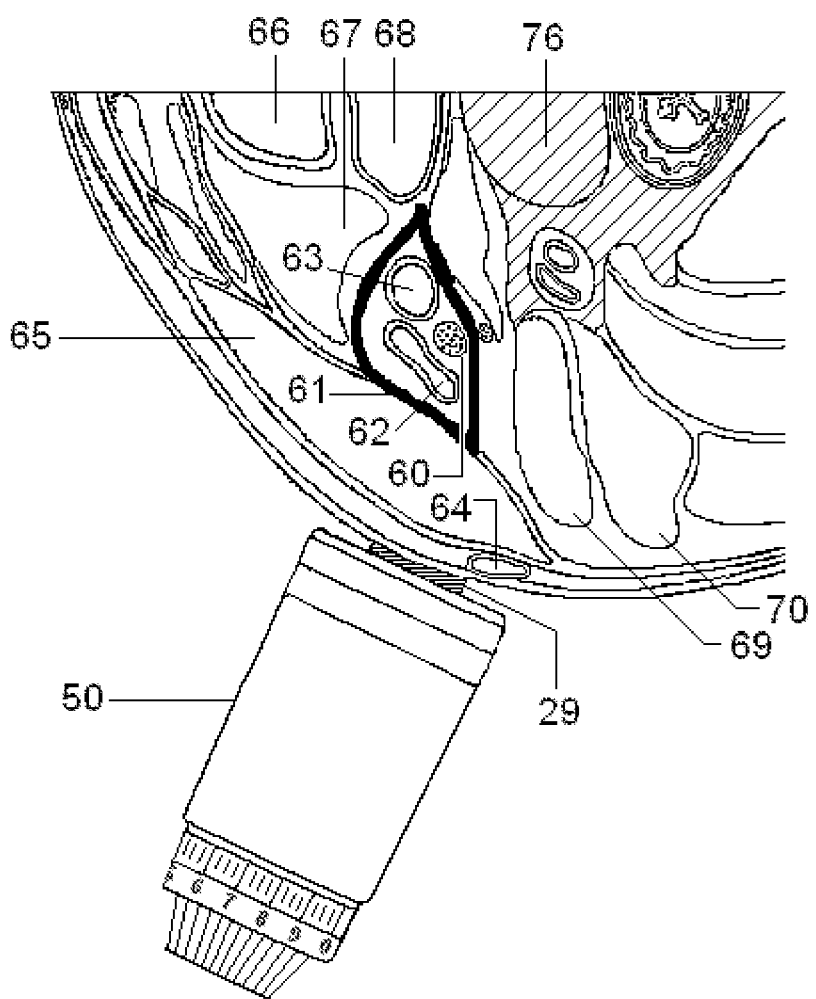
FIG. 7 illustrates the housing of the dual-electrode stimulator according one embodiment of the present invention, as the electrodes are positioned to stimulate the vagus nerve in a patient's neck, such that the stimulator is applied to the surface of the neck in the vicinity of the identified anatomical structures.

FIG. 7 provides a more detailed view of use of the electrical stimulator, when positioned to stimulate the vagus nerve at the neck location that is indicated in FIG. 6. As shown, the stimulator 50 in FIG. 5 touches the neck indirectly, by making electrical contact through conducting gel 29 (or other conducting material) which may be is dispensed through mesh openings (identified as 51 in FIG. 5) of the stimulator or applied as an electrode gel or paste. The layer of conducting gel 29 in FIG. 7 is shown to connect the device to the patient's skin, but it is understood that the actual location of the gel layer(s) may be generally determined by the location of mesh 51 shown in FIG. 5. Furthermore, it is understood that for other embodiments of the invention, the conductive head of the device may not necessitate the use of additional conductive material being applied to the skin.

The vagus nerve 60 is identified in FIG. 7, along with the carotid sheath 61 that is identified there in bold peripheral outline. The carotid sheath encloses not only the vagus nerve, but also the internal jugular vein 62 and the common carotid artery 63. Features that may be identified near the surface of the neck include the external jugular vein 64 and the sternocleidomastoid muscle 65. Additional organs in the vicinity of the vagus nerve include the trachea 66, thyroid gland 67, esophagus 68, scalenus anterior muscle 69, and scalenus medius muscle 70. The sixth cervical vertebra 76 is also shown in FIG. 7, with bony structure indicated by hatching marks.

Methods of treating a patient comprise stimulating the vagus nerve as indicated in FIGS. 6 and 7, using the electrical stimulation devices that are disclosed herein. The position and angular orientation of the device are adjusted about that location until the patient perceives stimulation when current is passed through the stimulator electrodes. The applied current is increased gradually, first to a level wherein the patient feels sensation from the stimulation. The power is then increased, but is set to a level that is less than one at which the patient first indicates any discomfort. Straps, harnesses, or frames are used to maintain the stimulator in position (not shown in FIG. 6 or 7). The stimulator signal may have a frequency and other parameters that are selected to produce a therapeutic result in the patient. Stimulation parameters for each patient are adjusted on an individualized basis. Ordinarily, the amplitude of the stimulation signal is set to the maximum that is comfortable for the patient, and then the other stimulation parameters are adjusted.

The stimulation is then performed with a sinusoidal burst waveform like that shown in FIG. 2. The pattern of a burst followed by silent inter-burst period repeats itself with a period of T. For example, the sinusoidal period $\tau$ may be 200 microseconds; the number of pulses per burst may be N=5; and the whole pattern of burst followed by silent inter-burst period may have a period of T=40000 microseconds, which is comparable to 25 Hz stimulation. More generally, there may be 1 to 20 pulses per burst, preferably five pulses. Each pulse within a burst has a duration of 20 to 1000 microseconds, preferably 200 microseconds. A burst followed by a silent inter-burst interval repeats at 1 to 5000 bursts per second (bps), preferably at 5-50 bps, and even more preferably 10-25 bps stimulation (10-25 Hz). The preferred shape of each pulse is a full sinusoidal wave, although triangular or other shapes may be used as well. The stimulation is then performed typically for 30 minutes and the treatment is performed once a week for 12 weeks or longer. However, it is understood that parameters of the stimulation protocol may be varied in response to heterogeneity in the pathophysiology of patients.

In other embodiments of the invention, pairing of vagus nerve stimulation may be with a time-varying sensory stimulation. The paired sensory stimulation may be bright light, sound, tactile stimulation, or electrical stimulation of the tongue to simulate odor/taste, e.g., pulsating with the same frequency as the vagus nerve electrical stimulation. The rationale for paired sensory stimulation is the same as simultaneous, paired stimulation of both left and right vagus nerves, namely, that the pair of signals interacting with one another in the brain may result in the formation of larger and more coherent neural ensembles than the neural ensembles associated with the individual signals, thereby enhancing the therapeutic effect. For example, the hypothalamus is well known to be responsive to the presence of bright light, so exposing the patient to bright light that is fluctuating with the same stimulation frequency as the vagus nerve (or a multiple of that frequency) may be performed in an attempt to enhance the role of the hypothalamus in producing the desired therapeutic effect. Such paired stimulation does not necessarily rely upon neuronal plasticity and is in that sense different from other reports of paired stimulation [Navzer D. ENGINEER, Jonathan R. Riley, Jonathan D. Seale, Will A. Vrana, Jai A. Shetake, Sindhu P. Sudanagunta, Michael S. Borland and Michael P. Kilgard. Reversing pathological neural activity using targeted plasticity. Nature 470(7332, 2011):101-4].

The individualized selection of parameters for the nerve stimulation protocol may based on trial and error in order to obtain a beneficial response without the sensation of pain or muscle twitches. Ordinarily, the amplitude of the stimulation signal is set to the maximum that is comfortable for the patient, and then the other stimulation parameters are adjusted. Alternatively, the selection of parameter values may involve tuning as understood in control theory, and as described below. It is understood that parameters may also be varied randomly in order to simulate normal physiological variability, thereby possibly inducing a beneficial response in the patient [Buchman T G. Nonlinear dynamics, complex systems, and the pathobiology of critical illness. Curr Opin Crit Care 10(5, 2004):378-82].

Individualized treatment may be based on the methods that will now be described in connection with the use of control theory to select stimulation parameters. In brief, the patient's physiological and medical state are modeled a set of differential equations, for example, as coupled nonlinear oscillators; measurements concerning the patient's function are made preferably using ambulatory measurement sensors; parameters of the equations are estimated using the measurements, including measurement of the patient's function following stimulation with different parameters that may be used for the stimulation protocol; and a treatment protocol (set of stimulation parameters) is selected that will avoid or ameliorate the effects of undesired events.

If it is desired to maintain a constant stimulation in the vicinity of the vagus nerve (or any other nerve or tissue that is being stimulated), methods may also be employed to modulate the power of the stimulator in order to compensate for patient motion or other mechanisms that would otherwise give rise to variability in the power of stimulation. In the case of stimulation of the vagus nerve, such variability may be attributable to the patient's breathing, which may involve contraction and associated change in geometry of the sternocleidomastoid muscle that is situated close to the vagus nerve (identified as 65 in FIG. 7). Methods for compensating for motion and other confounding factors were disclosed by the present Applicant in commonly assigned co-pending application entitled Non-Invasive Treatment of Bronchial Constriction, to SIMON et al, which was cited in the section CROSS REFERENCE TO RELATED APPLICATIONS and which is hereby incorporated by reference. Such modulation may be accomplished using controllers (e.g. PID controllers) that are known in the art of control theory, as now described.

Figure 8:
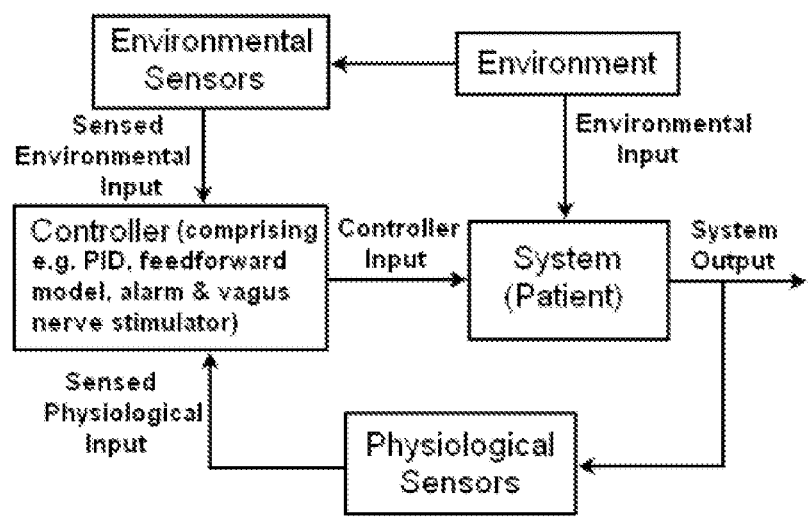
FIG. 8 illustrates connections between the controller and controlled system according to the present invention, their input and output signals, and external signals from the environment.

FIG. 8 is a control theory representation of the disclosed vagus nerve stimulation methods, used not only to maintain a constant stimulation, but also used in connection with the selection of stimulation parameters and stimulation protocols as described below. As shown in FIG. 8, the patient, or the relevant physiological component of the patient, is considered to be the "System" that is to be controlled. The "System" (patient) receives input from the "Environment." For example, in the case of an asthmatic, the environment would include breathed irritants; or in the case of a migraineur, the environment may include flickering or bright light that could trigger an aura. If the "System" is defined to be only a particular physiological component of the patient, the "Environment" may also be considered to include physiological systems of the patient that are not included in the "System". Thus, if some physiological component can influence the behavior of another physiological component of the patient, but not vice versa, the former component could be part of the environment and the latter could be part of the system. On the other hand, if it is intended to control the former component to influence the latter component, then both components should be considered part of the "System."

The System also receives input from the "Controller", which in this case comprises the vagus nerve stimulation device, as well as electronic components that may be used to select or set parameters for the stimulation protocol (amplitude, frequency, pulse width, burst number, etc.) or alert the patient as to the need to use the stimulator (i.e., an alarm). For example, the controller may include the control unit 330 in FIG. 1. Feedback in the schema shown in FIG. 8 is possible because physiological measurements of the System are made using sensors. Thus, the values of variables of the system that could be measured define the system's state ("the System Output"). As a practical matter, only some of those measurements are actually made, and they represent the "Sensed Physiological Input" to the Controller. As described in the Background section to this disclosure, the preferred sensors will be ordinarily used for ambulatory monitoring, selected to characterize the components of the patient's physiology that are to be controlled. For example, they may comprise respiratory sensors for asthma patients, EEG electrodes for epilepsy patients, ECG electrodes or blood pressure sensors for cardiac patients, etc.

Let the measured output variables of the system be denoted by $y_i$ (i=1 to Q); let the desired (reference or setpoint) values of $y_i$ be denoted by $r_i$ and let the controller's input to the system consist of variables $u_j$ (j=1 to P). The objective is for a controller to select the input $u_j$ in such a way that the output variables (or a subset of them) closely follows the reference signals $r_i$, i.e., the control error $e_i=r_i-y_i$ is small, even if there is environmental input or noise to the system. Consider the error function $e_j=r_i-y_i$ to be the sensed physiological input to the controller in FIG. 8 (i.e., the reference signals are integral to the controller, which subtracts the measured system values from them to construct the control error signal). The controller will also receive a set of measured environmental signals $v_k$ (k=1 to R), which also act upon the system as shown in FIG. 8.

For present purposes, no distinction is made between a system output variable and a variable representing the state of the system. Then, a state-space representation, or model, of the system consists of a set of first order differential equations of the form $dy_i/dt=F_i(t,\{y_i\},\{u_j\},\{v_k\};\{r_i\})$, where t is time and where in general, the rate of change of each variable $y_i$ is a function ($F_i$) of many other output variables as well as the input and environmental signals.

Classical control theory is concerned with situations in which the functional form of $F_i$ is as a linear combination of the state and input variables, but in which coefficients of the linear terms are not necessarily known in advance. In this linear case, the differential equations may be solved with linear transform (e.g., Laplace transform) methods, which convert the differential equations into algebraic equations for straightforward solution. Thus, for example, a single-input single-output system (dropping the subscripts on variables) may have input from a controller of the form:

$$u(t) = K_p e(t) + K_i \int_0^t e(\tau)d\tau + K_d \frac{de}{dt}$$

where the parameters for the controller are the proportional gain ($K_p$), the integral gain ($K_i$) and the derivative gain ($K_d$). This type of controller, which forms a controlling input signal with feedback using the error e=r−y, is known as a PID controller (proportional-integral-derivative).

Optimal selection of the parameters of the controller could be through calculation, if the coefficients of the corresponding state differential equation were known in advance. However, they are ordinarily not known, so selection of the controller parameters (tuning) is accomplished by experiments in which the error e either is or is not used to form the system input (respectively, closed loop or open loop experiments). In an open loop experiment, the input is increased in a step (or random binary sequence of steps), and the system response is measured. In a closed loop experiment, the integral and derivative gains are set to zero, the proportional gain is increased until the system starts to oscillate, and the period of oscillation is measured. Depending on whether the experiment is open or closed loop, the selection of PID parameter values may then be selected according to rules that were described initially by Ziegler and Nichols. There are also many improved versions of tuning rules, including some that can be implemented automatically by the controller [LI, Y., Ang, K. H. and Chong, G. C. Y. Patents, software and hardware for PID control: an overview and analysis of the current art. IEEE Control Systems Magazine, 26 (1, 2006): 42-54; Karl Johan Åström & Richard M. Murray. Feedback Systems: An Introduction for Scientists and Engineers. Princeton N.J.: Princeton University Press, 2008; Finn HAUGEN. Tuning of PID controllers (Chapter 10) In: Basic Dynamics and Control. 2009. ISBN 978-82-91748-13-9. TechTeach, Enggravhgda 45, N-3711 Skien, Norway. http://techteach.no., pp. 129-155; Dingyu XUE, YangQuan Chen, Derek P. Atherton. PID controller design (Chapter 6), In: Linear Feedback Control: Analysis and Design with MATLAB. Society for Industrial and Applied Mathematics (SIAM). 3600 Market Street, 6th Floor, Philadelphia, Pa. (2007), pp. 183-235; Jan JANTZEN, Tuning Of Fuzzy PID Controllers, Technical University of Denmark, report 98-H 871, Sep. 30, 1998].

Commercial versions of PID controllers are available, and they are used in 90% of all control applications. However, performance of system control can be improved by combining the feedback closed-loop control of a PID controller with feed-forward control, wherein knowledge about the system's future behavior can be fed forward and combined with the PID output to improve the overall system performance. For example, if the sensed environmental input in FIG. 8 is such the environmental input to the system will have a deleterious effect on the system after a delay, the controller may use this information to provide anticipatory control input to the system, so as to avert or mitigate the deleterious effects that would have been sensed only after-the-fact with a feedback-only controller. Because the present invention is concerned with anticipating and averting acute medical events, the controller shown in FIG. 8 will generally make use of feed-forward methods [Coleman BROSILOW, Babu Joseph. Feedforward Control (Chapter 9) In: Techniques of Model-Based Control. Upper Saddle River, N.J.: Prentice Hall PTR, 2002. pp, 221-240]. Thus, the controller in FIG. 8 is a type of predictive controller, methods for which have been developed in other contexts as well, such as when a model of the system is used to calculate future outputs of the system, with the objective of choosing among possible inputs so as to optimize a criterion that is based on future values of the system's output variables.

A mathematical model of the system is needed in order to perform the predictions of system behavior. Models that are completely based upon physical first principles (white-box) are rare, especially in the case of physiological systems. Instead, most models that make use of prior structural and mechanistic understanding of the system are so-called grey-box models, one of which is described below in connection with the forecasting of asthma attacks. Another example of a grey-box model was disclosed in the co-pending, commonly assigned application NON-INVASIVE ELECTRICAL AND MAGNETIC NERVE STIMULATORS USED TO TREAT OVERACTIVE BLADDER AND URINARY INCONTINENCE. If the mechanisms of the systems are not sufficiently understood in order to construct a white or grey box model, a black-box model may be used instead. Such models comprise autoregressive models [Tim BOLLERSLEV. Generalized autoregressive condiditional heteroskedasticity. Journal of Econometrics 31(1986):307-327], or those that make use of principal components [James H. STOCK, Mark W. Watson. Forecasting with Many Predictors, In: Handbook of Economic Forecasting. Volume 1, G. Elliott, C. W. J. Granger and A. Timmermann, eds (2006) Amsterdam: Elsevier B. V, pp 515-554], Kalman filters [Eric A. WAN and Rudolph van der Merwe. The unscented Kalman filter for nonlinear estimation, In: Proceedings of Symposium 2000 on Adaptive Systems for Signal Processing, Communication and Control (AS-SPCC), IEEE, Lake Louise, Alberta, Canada, October, 2000, pp 153-158], wavelet transforms [O. RENAUD, J.-L. Stark, F. Murtagh. Wavelet-based forecasting of short and long memory time series. Signal Processing 48(1996):51-65], hidden Markov models [Sam ROWEIS and Zoubin Ghahramani. A Unifying Review of Linear Gaussian Models. Neural Computation 11(2, 1999): 305-345], or artificial neural networks [Guoquiang ZHANG, B. Eddy Patuwo, Michael Y. Hu. Forecasting with artificial neural networks: the state of the art. International Journal of Forecasting 14(1998): 35-62].

For the present invention, a grey-box model is preferred, but if a black-box model must be used instead, the preferred model will be one that makes use of support vector machines. A support vector machine (SVM) is an algorithmic approach to the problem of classification within the larger context of supervised learning. A number of classification problems whose solutions in the past have been solved by multi-layer back-propagation neural networks, or more complicated methods, have been found to be more easily solvable by SVMs. In the present context, a training set of physiological data will have been acquired that includes whether or not the patient is experiencing some type of acute attack. Thus, the classification of the patient's state is whether or not an attack is in progress, and the data used to make the classification consist of the remaining acquired physiological data, evaluated at Δ time units prior to the time at which the attack data are acquired. Thus, the SVM is trained to forecast the imminence of an attack Δ time units into the future. After training the SVM, it is implemented as part of the controller to sound an alarm and advise the use of vagal nerve stimulation, whenever there is a forecast of an imminent attack [Christopher J. C. BURGES. A tutorial on support vector machines for pattern recognition. Data Mining and Knowledge Discovery 2(1998), 121-167; J. A. K. Suykens, J. Vandewalle, B. De Moor. Optimal Control by Least Squares Support Vector Machines. Neural Networks 14 (2001):23-35; Sapankevych, N. and Sankar, R. Time Series Prediction Using Support Vector Machines: A Survey. IEEE Computational Intelligence Magazine 4(2, 2009): 24-38; Press, W H; Teukolsky, S A; Vetterling, W T; Flannery, B P (2007). Section 16.5. Support Vector Machines. In: Numerical Recipes: The Art of Scientific Computing (3rd ed.). New York: Cambridge University Press].

Although classical control theory works well for linear systems having one or only a few system variables, special methods have been developed for systems in which the system is nonlinear (i.e., the state-space representation contains nonlinear differential equations), or multiple input/output variables. Such methods are important for the present invention because the physiological system to be controlled will be generally nonlinear, and there will generally be multiple output physiological signals. It is understood that those methods may also be implemented in the controller shown in FIG. 8 [Torkel GLAD and Lennart Ljung. Control Theory. Multivariable and Nonlinear Methods. New York: Taylor and Francis, 2000; Zdzislaw BUBNICKI. Modern Control Theory. Berlin: Springer, 2005].

Turning now to the use of feedback to control the system, consider the problem of adjusting the input u(t) from the vagus nerve stimulator (i.e., output from the controller) in order to maintain a desired output from the system. The desired output will ordinarily be determined by the particular physiological system that is being controlled. Consider first a problem that was addressed in the co-pending, commonly assigned application NON-INVASIVE TREATMENT OF BRONCHIAL CONSTRICTION. As described there, the objective was to maintain the forced expiratory volume in one second ($FEV_1$) or an alternate lung function index $FEV_1$% VC at a predetermined value, using vagus nerve stimulation. Instead of using actual measurement of $FEV_1$, it was disclosed that surrogate measurements of $FEV_1$ could also be made, namely, pulsus paradoxus, accessory muscle use or airway resistance (Rint). Methods for obtaining signals proportional to those surrogates were described. For those measurements that give intermittent readings, interpolation may be used to construct a continuous surrogate signal, which may be designated as the system output y(t). It is preferred to maintain the surrogate reading at some value $r=y_0$, but it may be difficult to maintain constancy, for example, because the patient is breathing and the corresponding muscles under the stimulator are changing shape, or the method of positioning the stimulator to the patient's neck is such that the position may drift, etc. Nerve activation is generally a function of the second spatial derivative of the extracellular potential along the nerve's axon, which would be changing as the position of the stimulator varies relative to the axon. Thus, one expects that there will usually be some error $e=r-y$ that needs continuous adjustment.

The functional form of the system's input u(t) is constrained to be as shown in FIG. 2. Ordinarily, the parameter that needs adjusting is the one associated with the amplitude of the signal shown in FIG. 2, which should be increased or decreased to accommodate motion-related changes and drift. Rather than adjust the amplitude manually, one may use the PID that was described above, wherein the gains of the PID are tuned according to the Ziegler-Nichols or other rules. Thereafter, the PID adjusts the amplitude automatically so as to best maintain the patient's $FEV_1$ or surrogate value at a preferred value. The default amplitude parameter is then reset according to its average value over time, as the PID continuously adjusts the value of the input u(t) thorough adjustment of the stimulator signal's amplitude (and any other parameters that may have been tuned).

A different strategy for selecting the parameters in FIG. 2 may also be used, in which several alternate sets of stimulator values are available for use. This strategy would be used when the physiological system itself is not stationary. For example, brain waves detected with an EEG may at one time have certain semi-stationary characteristics, but at a later time, they may have different semi-stationary characteristics, which in either case may be modulated to desired setpoints by stimulating the patient with the vagus nerve stimulator. The effects of vagus nerve stimulation on surface EEG waveforms may be difficult to detect [Michael BEWERNITZ, Georges Ghacibeh, Onur Seref, Panos M. Pardalos, Chang-Chia Liu, and Basim Uthman. Quantification of the impact of vagus nerve stimulation parameters on electroencephalographic measures. AIP Conf. Proc. DATA MINING, SYSTEMS ANALYSIS AND OPTIMIZATION IN BIOMEDICINE; Nov. 5, 2007, Volume 953, pp. 206-219], but they may exist nevertheless [KOO B. EEG changes with vagus nerve stimulation. J Clin Neurophysiol. 18(5, 2001):434-41; KUBA R, Guzaninová M, Brázdil M, Novák Z, Chrastina J, Rektor I. Effect of vagal nerve stimulation on interictal epileptiform discharges: a scalp EEG study. Epilepsia. 43(10, 2002):1181-8; RIZZO P, Beelke M, De Carli F, Canovaro P, Nobili L, Robert A, Fornaro P, Tanganelli P, Regesta G, Ferrillo F. Modifications of sleep EEG induced by chronic vagus nerve stimulation in patients affected by refractory epilepsy. Clin Neurophysiol. 115(3, 2004):658-64]. If the effects on EEG prove too difficult to measure, the effect of vagus nerve stimulation on some related variable such as fMRI activation or blood flow in the brain may be measured instead [CHAE J H, Nahas Z, Lomarev M, Denslow S, Lorberbaum J P, Bohning D E, George M S. A review of functional neuroimaging studies of vagus nerve stimulation (VNS). J Psychiatr Res. 37(6, 2003):443-55; CONWAY C R, Sheline Y I, Chibnall J T, George M S, Fletcher J W, Mintun M A. Cerebral blood flow changes during vagus nerve stimulation for depression. Psychiatry Res. 146(2, 2006):179-84]. The semi-stationary brain wave epochs may correspond to circadian influences, or to different states of alertness, or they may have an unknown origin. In each epoch, stimulator parameters may be selected as described above in connection with the $FEV_1$ control. However, the default parameter values may be different, depending on which semi-stationary EEG epoch obtained at the time of PID tuning. Accordingly, when the stimulator is eventually used for prophylactic treatment of a patient, the stimulator should be set to parameter values that are selected to correspond to the semi-stationary EEG epoch that obtains immediately before stimulation is used for the prophylactic therapy. This is a type of closed-loop application because measurements of the EEG immediately before therapy are used as "feedback" to select one of possibly many sets of tuned stimulator parameter values for use in the prophylactic therapy.

Methods for Averting Imminent Asthma Attacks

Once air is inhaled through the mouth or nose, it travels through the trachea and a progressively subdividing system of bronchi (containing cartilage) and bronchioles (which contain no cartilage) until it finally reaches the alveoli, where the gas exchange of carbon dioxide and oxygen takes place. Through constriction or relaxation of smooth muscle within their walls, the bronchioles change diameter to either increase or reduce air flow. The bronchioles between the fourth and eighth bifurcation are thought to be most important in that regard. An increase in diameter (bronchodilation) is stimulated by epinephrine or sympathetic nerves to increase air flow, and a decrease in diameter (bronchoconstriction) is stimulated by histamine, parasympathetic nerves, cold air, and chemical irritants.

Patients with asthma experience attacks in which excessive constriction of the bronchioles make it difficult for them to breathe. The pathophysiology of asthma, and of the related disorders of chronic obstructive pulmonary disease (COPD) and anaphylaxis, is not fully understood. However, enough is known about asthma to forecast the onset of an asthma attack, as disclosed below. The objective of this aspect of the invention is to avert the forecasted bronchoconstriction by taking prophylactic countermeasures that involve electrical stimulation of the vagus nerve. Other potential countermeasures, such as the administration of epinephrine, might also be considered [ANDERSON G P. Endotyping asthma: new insights into key pathogenic mechanisms in a complex, heterogeneous disease. Lancet 372(9643, 2008): 1107-19; CAIRNS C B. Acute asthma exacerbations: phenotypes and management. Clin Chest Med. 27(1, 2006):99-108; RODRIGO G J. Predicting response to therapy in acute asthma. Curr Opin Pulm Med. 15(1, 2009):35-8].

Individual normal bronchioles undergo constant constriction and dilation, such that the diameters of their lumens may vary considerably over the course of even a few minutes. Normally, some bronchioles are constricting while others are dilating, but the time-varying heterogeneity of airway caliber throughout the lung is normally sufficient to bring air to all the alveoli, because any constricted bronchiole would reopen in a relatively short period of time. This oscillation of constriction and dilation of individual bronchioles throughout the lung leads to physiological fluctuations in airway resistance at the level of the whole lung [QUE C L, Kenyon C M, Olivenstein R, Macklem P T, Maksym G N. Homeokinesis and short-term variability of human airway caliber. J Appl Physiol 91(3, 2001):1131-41; MUSKULUS M, Slats A M, Sterk P J, Verduyn-Lunel S. Fluctuations and determinism of respiratory impedance in asthma and chronic obstructive pulmonary disease. J Appl Physiol 109(6, 2010):1582-91; FREY U, Maksym G, Suki B. Temporal complexity in clinical manifestations of lung disease. J Appl Physiol 110(6, 2011)1723-31]. Accordingly, the present invention describes bronchiole segments mathematically as oscillators, in which a variable corresponding to each bronchiole segment represents the varying radius of a bronchiole lumen, minus a value representing a time-averaged radius in a normal bronchiole. Because segments of the bronchial tree are fluctuating according to the invention, the oscillating branches collectively give rise to fluctuations in overall respiratory impedance.

It is thought that an asthma attack may correspond to an avalanche of airway constrictions, in which the constriction in one bronchiole segment increases the likelihood that another bronchiole branch in the same tree structure of the lung will constrict. The result is that some initial heterogeneity of airway constriction within different regions of the lung, which might seem to be of little physiological consequence, may actually become amplified by avalanches of airway constrictions, such that eventually large heterogeneous regions of the lung become unavailable for normal respiration. Models have been constructed to explain such heterogeneity and avalanches, but none of them are suitable for forecasting an imminent asthma attack [ALENCAR A M, Arold S P, Buldyrev S V, Majumdar A, Stamenovic D, Stanley H E, Suki B. Physiology: Dynamic instabilities in the inflating lung. Nature 417(6891, 2002):809-11; SUKI B, Frey U. Temporal dynamics of recurrent airway symptoms and cellular random walk. J Appl Physiol 95(5, 2003):2122-7; VENEGAS J G, Winkler T, Musch G, Vidal Melo M F, Layfield D, Tgavalekos N, Fischman A J, Callahan R J, Bellani G, Harris R S. Self-organized patchiness in asthma as a prelude to catastrophic shifts. Nature 434(7034, 2005): 777-82; FREY U, Brodbeck T, Majumdar A, Taylor D R, Town G I, Silverman M, Suki B. Risk of severe asthma episodes predicted from fluctuation analysis of airway function. Nature 438(7068, 2005):667-70; FREY U. Predicting asthma control and exacerbations: chronic asthma as a complex dynamic model. Curr Opin Allergy Clin Immunol 7(3, 2007):223-30; MULLALLY W, Betke M, Albert M, Lutchen K. Explaining clustered ventilation defects via a minimal number of airway closure locations. Ann Biomed Eng 37(2, 2009):286-300; POLITI A Z, Donovan G M, Tawhai M H, Sanderson M J, Lauzon A M, Bates J H, Sneyd J. A multiscale, spatially distributed model of asthmatic airway hyper-responsiveness. J Theor Biol 266(4, 2010): 614-24; TAWHAI M H, Bates J H. Multi-scale lung modeling. J Appl Physiol 110(5, 2011):1466-72; SUKI B, Bates J H. Emergent behavior in lung structure and function. J Appl Physiol 110(4, 2011):1109-10; KACZKA D W, Lutchen K R, Hantos Z. Emergent behavior of regional heterogeneity in the lung and its effects on respiratory impedance. J Appl Physiol 110(5, 2011):1473-81]. The model of lung dynamics that is disclosed below is able to make such a forecast. It does so by making oscillation of any one bronchiole oscillator a function of the state of other bronchiole oscillators, as well as a function of external conditions such as the presence of gas irritants and electrical stimulation of the vagus nerve.

The properties of oscillators are currently understood through the analysis of differential equation prototypes, such as Duffing's oscillator:

$$\frac{d^2y}{dt^2} + m\frac{dy}{dt} + \frac{dP}{dy} = f(t),$$

where y is the displacement of the oscillator (subtracted from a value representing a time-averaged radius under normal conditions, $y_0$), m is a damping parameter, P is a potential function of y, and $f(t)$ is a driving function. In the case of respiration, the driving function would correspond to the flow of air as the respiratory muscles generate inspiration or relax for expiration. The potential function P(y) is often assumed to satisfy $$\frac{dP}{dy} = by + ay^3,$$

where a and b are constants (i.e., $$P = \frac{b}{2}y^2 + \frac{a}{4}y^4\bigg),$$

which for a>0 and b<0 corresponds to a symmetric double-well potential. The potential may also be made asymmetric so that it is easier for the oscillator to reach one well than another, as in:

$$P = \frac{b}{2}y^2 + \frac{a}{4}y^4 + y[c + df(t)],$$

where c and d are parameters for asymmetry that is respectively independent of, or dependent on, the driving function $f(t)$. In any case, two types of motion may be seen with such a double-well model: the motion can be confined to one of the wells when a weak driving function $f(t)$ is applied; or the oscillator can escape a well and visit the other well, and vice versa, when a stronger driving function $f(t)$ is applied [O. I. OLUSOLA, U. E. Vincent, A. N. Njah, and J. A. Olowofela. Bistability in coupled oscillators exhibiting synchronized dynamics. Commun. Theor. Phys. 53(2010), pp. 815-824]. If noise is added to the system it is possible to convert the former type of motion into the latter, through a mechanism known as stochastic resonance [Luca Gammaitoni, Peter Hänggi, Peter Jung, and Fabio Marchesoni. Stochastic resonance. Rev. Mod. Phys. 70(1998), 223-287].

Duffing's equation describes oscillations in the displacement y that are qualitatively different than those exhibited by a linear, harmonic driven oscillator. Because it embodies a double-well potential, it is appropriate when a system is preferentially in one of two states, such as a constricted state versus a dilated state, as in the case of a bronchiole oscillator. If there were more than two preferential states, a potential having three or more wells may be assumed, as would be the case if the bronchiole oscillator had relaxed, dilated, and intermediate states. A network of coupled oscillators is constructed by making the displacement of one oscillator be a function of one or more of the other oscillators' displacements, i.e., by coupling each oscillator to other oscillators. Each oscillator in the network can in general have different parameter values, and the network can have different forms of local or non-local coupling.

Other well-studied non-linear oscillators include Van der Pol, FitzHugh-Nagumo, Morris-Lecar, Ellias-Grossberg, and Stuart-Landau. Although the detailed oscillations described by such prototypical equations are dependent on the detailed form of the equations and their initial conditions, the qualitative behaviors of such non-linear coupled oscillator equations may often be understood independently of the particular form of the non-linear equation. For example, it is well understood in general that non-linear oscillators, including a set of coupled non-linear oscillators, may exhibit qualitatively different behaviors when the parameters of their equations lie within certain bounds. When graphs are drawn showing the value of one parameter on one axis, and the value of another parameter on another axis, regions of this parameter space may be circumscribed to show what sets of parameter values correspond to each type of qualitatively different dynamics, i.e, a phase diagram. Examples of such phase diagrams are given by MATTHEWS and STROGATZ, which circumscribe different regions of phase space having qualitatively different dynamics, and which are also described below in connection with FIG. 9 [Paul C. MATTHEWS and Steven H. Strogatz. Phase diagram for the collective behavior of limit-cycle oscillators. Phys. Rev. Lett. 65(1990): 1701-1704].

When dealing with coupled nonlinear oscillators, such as coupled Duffing oscillators, the two or more oscillators may eventually all oscillate with the same phase or they may prefer to oscillate with unrelated phases, again depending on the range in which the parameter values lie. In the case of a two-well oscillator, the relation between the phase of different oscillators refers not only to simultaneously occurring peaks and valleys of displacement, but also whether oscillators are simultaneously trapped in the same potential well. Chimera states, in which part of the system is phase locked and simultaneously another part of the system exhibits oscillators with unrelated phases, are also possible. Chimera states may be particularly significant in regards to the regional inhomogeneity of the lung, when one portion of the lung exhibits unrelated phases, and another region exhibits phase locking. These qualitatively different types of dynamic behavior are influenced by the presence of noise, and they are exhibited by nonlinear oscillators generally, of which the Duffing oscillator is only one example [GUEVARA M. R. Bifurcations involving fixed points and limit cycles in biological systems. In: "Nonlinear Dynamics in Physiology and Medicine", edited by Beuter A., Glass L., Mackey M. C., Titcombe M. S. Springer-Verlag, New York, pp. 41-85 (2003); LEE, Wai Shing; Restrepo, Juan G.; Ott, Edward; Antonsen, Thomas M. Dynamics and pattern formation in large systems of spatially-coupled oscillators with finite response times. Chaos 21 (2, 2011), pp. 023122-023122-14; Hiroshi KORI and Alexander S. Mikhailov. Entrainment of Randomly Coupled Oscillator Networks by a Pacemaker. Phys. Rev. Lett. 93(2004), 254101, pp 1-4; M. CISZAK, A. Montina, and F. T. Arecchi. Sharp versus smooth synchronization transition of locally coupled oscillators. Phys. Rev. E 78(2008), 016202, pp 1-4; Daniel M. ABRAMS and Steven H. Strogatz. Chimera States for Coupled Oscillators. Phys. Rev. Lett. 93(2004), 174102, pp 1-4; KONISHI K. Experimental evidence for amplitude death induced by dynamic coupling: van der Pol oscillators. Proc. ISCAS (4, 2004) 792-795; Shinji DOI, Yohei Isotani, Ken-ichiro Sugimoto and Sadatoshi Kumagai. Noise-induced critical breakdown of phase lockings in a forced van der Pol oscillator. Physics Letters A 310 (5-6, 2003): 407-414].

When one or more of the parameters of the set of coupled nonlinear oscillators may be varied under external influences to produce qualitative changes of phase in the system, the parameter is said to be an order parameter. According to the present invention, bronchioles of the lung may be represented mathematically as nonlinear oscillators that are coupled to one another, and an order parameter for the system is the concentration of an environmental lung irritant, as shown in FIG. 9A. Another order parameter is related to the magnitude and duration of vagus nerve stimulation, which will be described below. Consider first only the changes in phase that occur as the concentration of the irritant increases. Moving along the lower axis in FIG. 9A at increasing irritant concentration, the successive phases that are encountered as the concentration is increased are called successively: phase drift, irregular region, and phase locked. The dynamics of the system in each of those phases is represented in FIG. 9B, in which the average, over multiple bronchioles, of bronchiole constriction is shown as a function of time. For present purposes, bronchial constriction is defined as the average of $y_0/y$, over many bronchioles, where $y_0$ is a time-averaged radius in a normal bronchiole and y is a bronchiole displacement from that radius, such that as y becomes smaller, the constriction becomes larger.

Within the phase drift phase, there are only small fluctuations of constriction amplitude averaged over many bronchioles. This corresponds to a situation in which the bronchioles are oscillating more or less independently of one another. Within the irregular phase, there are small fluctuations along with occasional irregularly-timed large amplitude constrictions. The dynamics are not periodic, but may instead exhibit aperiodic dynamics such as deterministic chaos, Hopf oscillation, quasiperiodicity, and large oscillation [Paul C. MATTHEWS and Steven H. Strogatz. Phase diagram for the collective behavior of limit-cycle oscillators. Phys. Rev. Lett. 65(1990): 1701-1704; Paul C. MATTHEWS, Renato E. Mirollo, and Steven H. Strogatz. Dynamics of a large system of coupled nonlinear oscillators. Physica D: Nonlinear Phenomena 52 (2-3, 1991): 293-331]. During the phase-locked phase, there are large amplitude constrictions, as evidenced by the average of the displacement y over many bronchioles. In that phase, the constrictions correspond to almost all bronchioles in some region(s) of the lung being trapped in one well of the double-well potential, namely, the well corresponding to a constricted bronchiole, as would occur in an asthma attack. However, the lung as a whole may also be in a chimera state, wherein some regions of the lung are in one phase such as the phase-locked phase, while other regions of the lung may be in some other phase such as the phase-drift phase, so that not all bronchioles of the lung need be constricted during an asthma attack.

Irritant concentrations may be measured non-invasively in real time for an ambulatory patient [Kirk J. Englehardt and John Toon. Asthma attack: Vest-based sensors monitor environmental exposure to help understand causes: web page (www) at the Georgia Tech Research Institute (.gtri) of Georgia Tech (.gatech) educational domain (.edu) in subdomain: /casestudy/asthma-vest-helps-id-asthma-causes; patent application US20110144515, entitled Systems and methods for providing environmental monitoring, to Bayer et al.; and U.S. Pat. No. 7,119,900, entitled Pollen sensor and method, to Okumura et al]. For physical external irritants, the unit of irritation should be selected accordingly, such as temperature for cold air as an irritant.

It is understood, however, that in some patients, external irritant triggers are hard to identify, and some irritant triggers may well be endogenous substances. In that case, according to the invention, a surrogate for an unknown or endogenous trigger concentration may be the concentration of exhaled nitric oxide, which can be measured noninvasively using miniature gas sensors placed in the vicinity of the patient's mouth [Gill M, Walker S, Khan A, Green S M, Kim L, Gray S, Krauss B. Exhaled nitric oxide levels during acute asthma exacerbation. Acad Emerg Med 12(7, 2005):579-86; Oleksandr KUZMYCH, Brett L Allen and Alexander Star. Carbon nanotube sensors for exhaled breath components. Nanotechnology 18 (2007) 375502, pp 1-7]. Accordingly, what is labeled as "Concentration of Environmental Irritants" in FIG. 9 may be replaced by the concentration of any other exogenous or endogenous trigger, or by a surrogate for an asthma trigger.

Referring again to the phase diagram in FIG. 9A, note that the vertical axis is labeled as "Vagus Nerve Stimulation." According to the present invention, the effectiveness of vagus nerve stimulation in inhibiting bronchiole constriction is a function of the stimulation voltage, the duration of the stimulation, and if stimulation has ceased, the time since cessation of the last stimulation. Let the numerical value of the accumulated "Vagus Nerve stimulation" with a particular stimulation waveform be denoted as S(t). It may for present purposes be represented as a function that increases at a rate proportional to the stimulation voltage V and decays with a time constant $\tau_p$, such that after prolonged stimulation, the accumulated stimulation effectiveness will saturate at a value equal to the product of V and $\tau_p$. Thus, if $T_p$ is the duration of a vagal nerve stimulation, then for time $t<T_p$, $S(t)=V\tau_p[1-\exp(-t/\tau_p)]+S_0\exp(-t/\tau_p)$, and for $t>T_p$, $S(t)=S(T_p)\exp(-[t-T_p]/\tau_p)$, where the time t is measured from the start of a stimulus, and $S_0$ is the value of S when t=0. Then, according to FIG. 9, as electrical stimuli to the vagus nerve are applied, it is possible for the lung system as a whole to switch from one phase of bronchial constriction to another, even if the lung is exposed to a constant irritant environment.

For example, if the system begins in the phase locked phase shown in FIG. 9A (asthma attack), it can be simulated up and out of that phase into the phase drift phase, and after stimulus ceases, the system will eventually decay back into the phase locked phase. The situation with any given individual would depend upon that individual's particular phase diagram, but if the individual has a diagram like the one shown in FIG. 9A, then the best strategy for preventing or terminating unwanted bronchoconstriction would be to stimulate the vagus nerve for as long as possible with as high a voltage as possible, so as to drive the system out of its current phase and into the phase drift phase (or maintain it in the drift phase) for as long as possible. However, that strategy may not be practical, because at some voltage, the stimulus would be too painful, and the stimulation is not intended to be continuous, as could have been the case with an implanted stimulator. Furthermore, because of decay of the accumulated stimulus effect, additional stimulation may be increasingly ineffective as the effect saturates at a level determined by the stimulation voltage V and decay time constant $\tau_p$.

Implementation of the method for forecasting an asthma attack requires a mathematical embodiment of the invention. For example, in one embodiment, the bronchiole oscillators are represented as coupled Duffing oscillators, as in the following equations with two oscillators. Such a representation can be expanded to any number of oscillators by making all oscillators coupled to all other oscillators so as to emphasize neural or humoral feedback loops, or only to oscillators in proximity to one another so as to emphasize local nearest-neighbor effects, or some intermediate coupling configuration.

$$\frac{d^2y_1}{dt^2} + m_1\frac{dy_1}{dt} + \frac{dp_1}{dy_1} = f_1(t) \text{ and}$$

$$\frac{d^2y_2}{dt^2} + m_2\frac{dy_2}{dt} + \frac{dp_2}{dy_2} = f_2(t)$$

where $y_1$ and $y_2$ are the radii of sister branches of bronchioles relative to an offset $y_0$. For example, the bronchioles may be between the fourth and eighth bronchial bifurcations. One form of coupling is through the fact that a flow $f(t)$ through the parent bronchiole of bronchioles 1 and 2 is $f(t)=f_1(t)+f_2(t)$, so that if one sister bronchiole constricts and the other sister bronchiole does not, the flow $f(t)$ will be preferentially distributed to the latter bronchiole. For purposes of estimating the flows, it is assumed that nasal and/or oral airflow is measured (e.g., with thermistors) in conjunction with respiratory inductive plethysmography, mercury in silastic strain gauges or impedance pneumography so as to measure total respiratory air flow, which can be calibration with a spirometer. Assuming that the lengths of the bronchi and bronchioles are the same at any corresponding level of branching, assuming the validity of Ohm's law and Poiseuille's law, and given the measured total air flow, the values of the driving flows $f_1(t)$ and $f_2(t)$ can be estimated for the current values of $y_1$ and $y_2$. Similar equations are written for the multiple levels of bronchiole bifurcations. Because flow at one level of bronchiole branching can influence flow that is connected to it at another level, the equations for the bronchiole oscillators are therefore coupled to one another by virtue of the anatomy of the lung and flow within the branching bronchioles.

According to the invention, the presence of irritant in the airstream of any bronchiole (or other trigger surrogate) is accounted for by making parameters describing the potential P be a function of the flow and concentration of environmental irritant. For example, with the asymmetric potential $$P = \frac{b}{2}y^2 + \frac{a}{4}y^4 + y[c + df(t)],$$

where d is a parameter that is a function of irritant concentration, the system would preferentially constrict the bronchiole on inspiration (positive $f$, preventing the irritant from reaching the alveoli) and preferentially dilate the bronchiole on expiration (negative $f$, allowing the irritant to be expelled from the alveoli). If K is the irritant concentration, then for example, the dependence of parameter d on K may be expressed as $d=d_0+d_1K+d_2K^2+\ldots$ An increase in the parameter c would increase the stability of the potential well corresponding to bronchoconstriction, independently of any changes in the flow. Accordingly, stimulation of the bronchioles by histamine, the parasympathetic nervous system, or any other factor that promotes bronchoconstriction should be accompanied by an increase in the parameter c. Conversely, a decrease in the parameter c would increase the stability of the potential well corresponding to bronchodilation. Accordingly, stimulation of the bronchioles by epinephrine, the sympathetic nervous system, or any other factor that promotes bronchodilation should be accompanied by a decrease in the parameter c. For example, one may write c as $c=c_c-c_d$, where an increase in $c_c$ caused bronchoconstriction and an increase in $c_d$ causes bronchodilation. Then, the vagal nerve stimulation S(t), which was defined above, may be introduced through the parameter $c_d$. For example, $c_d=c_{d0}+c_{d1}S+c_{d2}S^2+\ldots$ Breathing is to some extent under voluntary control, so that an individual can deliberately vary the driving function $f(t)$. On the other hand, breathing is also to some extent involuntary and controlled by the nervous system. Accordingly, one may expand the above model to account for respiratory reflexes [H. T. MILHORN Jr., R. Benton, R. Ross, and A. C. Guyton. A mathematical model of the human respiratory control system. Biophys J. 5(1965):27-46]. To do so, the coupling parameter(s) may also be made to be a function of multiple oscillator values, possibly at a previous time t−Δ, so as to account for the time delay Δ in neural reflexes between afferent signals and efferent effects that couple oscillators to one another. Such an expanded neural control model may be used to forecast $f(t)$, or alternatively, non-physiological models may be used to forecast future values of $f(t)$ based on previous values of $f(t)$ [CAMINAL P, Domingo L, Giraldo B F, Vallverdú M, Benito S, Vázquez G, Kaplan D. Variability analysis of the respiratory volume based on non-linear prediction methods. Med Biol Eng Comput 42(1, 2004):86-91]. It is understood that additional extensions of the above dynamical model may make the anatomy and physiology more complete, accurate or detailed; for example, one may wish to create a more realistic model of the patient's lung anatomy than what was described above [LEE, S. L. A.; Kouzani, A. Z.; Hu, E. J.; From lung images to lung models: A review. IEEE International Joint Conference on Neural Networks 2008: 2377-2383].

Usefulness of this method is dependent on the extent to which the patient is willing to undergo measurement to allow estimation of an embodiment of the equations' parameters. It is understood that the measurement will consist of a period of baseline monitoring, followed by a period during which the vagus nerve is stimulated using a default stimulation protocol or during which vagal nerve stimulation parameters are varied. The most useful measurements would be ones in which nearby groups of bronchioles are measured separately, so as to be able to estimate parameters separately for those localized groups of oscillators. This will require imaging of the lung in order to evaluate the spatial heterogeneity of bronchiolar constriction.

Many methods exist for the noninvasive imaging of the lung. However, the noninvasive imaging methods that are preferred here are those that may be performed by continuous noninvasive ambulatory monitoring. At the present time, the preferred imaging methods comprise electrical impedance tomography and acoustic imaging. Electrical impedance tomography (EIT) is an imaging technique in which an image of the conductivity of the chest is inferred from surface electrical measurements. To perform EIT, conducting electrodes are attached to the skin of the patient and small alternating currents are applied to some or all of the electrodes. The resulting electrical potentials are measured, and the process may be repeated for numerous different configurations of applied current. A calculation is then performed to infer the lung structure that could have given rise to the measured electrical potentials [David HOLDER. Electrical impedance tomography: methods, history, and applications. Institute of Physics Publishing, Bristol and Philadelphia, 2005; WENG T R, Spence J A, Polgar G, Nyboer J. Measurement of regional lung function by tetrapolar electrical impedance plethysmography. Chest 76(1, 1979):64-9; FRERICHS I. Electrical impedance tomography (EIT) in applications related to lung and ventilation: a review of experimental and clinical activities. Physiol Meas. 21(2, 2002):R1-21; FRERICHS I, Hinz J, Herrmann P, Weisser G, Hahn G, Dudykevych T, Quintel M, Hellige G. Detection of local lung air content by electrical impedance tomography compared with electron beam C T. J Appl Physiol 93(2, 2002):660-6; J. KARSTEN, T. Meier, H. Heinze. Bedside-measurements of electrical impedance tomography and functional residual capacity during positioning therapy in a case of acute respiratory failure Applied Cardiopulmonary Pathophysiology, 15(2011): 81-86; FAGERBERG A, Söndergaard S, Karason S, Aneman A. Electrical impedance tomography and heterogeneity of pulmonary perfusion and ventilation in porcine acute lung injury. Acta Anaesthesiol Scand. 2009 November; 53(10): 1300-9].

The other noninvasive ambulatory imaging method, acoustic imaging, involves the placement of multiple microphones on the patient's chest and back. It is particularly useful to detect and localize groups of bronchioles that have abruptly opened and made a corresponding sound [KOMPIS M, Pasterkamp H, Wodicka G R. Acoustic imaging of the human chest. Chest 120(4, 2001):1309-21; PASTERKAMP H, Kraman S S, Wodicka G R. Respiratory sounds. Advances beyond the stethoscope. Am Respir Crit Care Med 156(3 Pt 1, 1997):974-87; Adriano M. ALCENAR, Arnab Majumdar, Zoltan Hantos, Sergey V. Buldyrev, H. Eugene Stanley, Béla Suki. Crackles and instabilities during lung inflation. Physica A: Statistical Mechanics and its Applications 357(1, 2005): 18-26].

In addition to these noninvasive measurements, as well as conventional ambulatory measurements for breathing, heart rate, and the like, one would preferably add an accelerometer and/or inclinometer so as to account for changes in lung anatomy and physiology as the patient changes posture or moves about [GALVIN I, Drummond G B, Nirmalan M. Distribution of blood flow and ventilation in the lung: gravity is not the only factor. Br J Anaesth 98(4, 2007):420-8]. The sensors may be embedded in garments or placed in sports wristwatches, as currently used in programs that monitor the physiological status of soldiers [G. A. Shaw, A. M. Siegel, G. Zogbi, and T. P. Opar. Warfighter physiological and environmental monitoring: a study for the U.S. Army Research Institute in Environmental Medicine and the Soldier Systems Center. MIT Lincoln Laboratory, Lexington Mass. 1 Nov. 2004, pp. 1-141].

Estimation of parameters of the equations from continuously acquired data may be made using existing methods such as the multiple shooting and recursive (e.g., Kalman filter) approaches [Henning U. VOSS and Jens Timmer. Nonlinear dynamical system identification from uncertain and indirect measurements. International Journal of Bifurcation and Chaos 14(6, 2004):1905-1933], or synchronization methods [HDI ABARBANEL, D R Creveling, and J M Jeanne. Estimation of parameters in nonlinear systems using balanced synchronization. Physical Review E 77(2008): 016208, pp 1-14]. As the patient's ambulatory data evolve in time, the estimated parameters may also evolve in time and must be updated.

After parameter estimation, numerical simulation with the coupled-oscillator equations into the future may forecast the imminent onset of an asthma attack, i.e., an abrupt transition wherein groups of bronchioles constrict (see FIG. 9). It is understood that the simulation must occur at a rate that is significantly faster than actual time, otherwise there would be little warning for the patient. When such a warning is given, the patient or a caregiver would perform vagus nerve stimulation as described above in order to avert the asthma attack. The rationale for performing the vagus nerve stimulation is described in the co-pending, commonly assigned application entitled NON-INVASIVE TREATMENT OF BRONCHIAL CONSTRICTION, which is listed in the section CROSS REFERENCE TO RELATED APPLICATIONS.

For situations in which it is impractical to use the above gray-box model of asthma, for example, if the patient is unwilling to wear the electrical impedance tomography and acoustic imaging sensors for measuring respiratory heterogeneity, then one may instead use the black-box approach that was described above (and also below in connection with migraine, strokes, and panic attacks) using the remaining sensors (respiration, environmental sensors, etc.) [G. A. Shaw, A. M. Siegel, G. Zogbi, and T. P. Opar. Warfighter physiological and environmental monitoring: a study for the U.S. Army Research Institute in Environmental Medicine and the Soldier Systems Center. MIT Lincoln Laboratory, Lexington Mass. 1 Nov. 2004, pp. 1-141]. In that case, the patient would mark the onset of an asthma attack with an event button, and the set of ambulatory measurements would be used to train a support vector machine classifier model. After training, that model will be used to forecast the asthma attack and advise the patient to perform vagus nerve stimulation.

Methods for Averting Imminent Epilepsy Seizures

There is a large literature on methods for forecasting epilepsy seizures. Current methods have been the subject of several reviews [Brian LITT and Javier Echauz. Prediction of epileptic seizures. Lancet Neurology 1(2002): 22-30; MORMANN F, Andrzejak R G, Elger C E, Lehnertz K. Seizure prediction: the long and winding road. Brain 130(Pt 2, 2007):314-33; MORMANN F, Kreuz T, Rieke C, Andrzejak R G, Kraskov A, David P, Elger C E, Lehnertz K. On the predictability of epileptic seizures. Clin Neurophysiol 116(3, 2005):569-87; MORMANN F, Elger C E, Lehnertz K. Seizure anticipation: from algorithms to clinical practice. Curr Opin Neurol 19(2, 2006):187-93]. Tools are also available for the development of new methods for forecasting epilepsy seizures [TEIXEIRA C A, Direito B, Feldwisch-Drentrup H, Valderrama M, Costa R P, Alvarado-Rojas C, Nikolopoulos S, Le Van Quyen M, Timmer J, Schelter B, Dourado A. EPILAB: a software package for studies on the prediction of epileptic seizures. J Neurosci Methods. 200(2, 2011): 257-71].

The brain-wave data used to make the forecast are either from electrodes that are implanted in the patient's brain, or from electroencephalographic electrodes that are worn or attached to the patient's scalp [CASSON A, Yates D, Smith S, Duncan J, Rodriguez-Villegas E. Wearable electroencephalography. What is it, why is it needed, and what does it entail? IEEE Eng Med Biol Mag. 29(3, 2010):44-56]. Additional data may also be useful in making the forecast, such as data concerning heart rate [DELAMONT R S, Julu P O, Jamal G A. Changes in a measure of cardiac vagal activity before and after epileptic seizures. Epilepsy Res 35(2, 1999):87-94]. Thus, VALDERRAMA et al. are able to improve the forecast of a seizure by including the analysis of ECG data with EEG data [M. VALDERRAMA, S. Nikolopoulos, C. Adam, Vincent Navarro and M. Le Van Quyen. Patient-specific seizure prediction using a multi-feature and multi-modal EEG-ECG classification. XII Mediterranean Conference on Medical and Biological Engineering and Computing 2010, IFMBE Proceedings, 2010, Volume 29, Part 1, 77-80]. Lack of sleep and the patient's self-prediction of whether a seizure is imminent may also useful in making a forecast [HAUT S R, Hall C B, Masur J, Lipton R B. Seizure occurrence: precipitants and prediction. Neurology. 69(20, 2007):1905-10]. Motion data collected using an accelerometer may be useful for detecting artifacts [Sweeney K T, Leamy D J, Ward T E, McLoone S. Intelligent artifact classification for ambulatory physiological signals. Conf Proc IEEE Eng Med Biol Soc. 2010; 2010:6349-52].

Proposed countermeasures against the forecasted epileptic seizures comprise: on-demand excretion of fast-acting anticonvulsant substances, local cooling, biofeedback operant conditioning, and electrical or other stimulation to reset brain dynamics to a state that will not develop into a seizure [STACEY W C, Litt B. Technology insight: neuroengineering and epilepsy-designing devices for seizure control. Nat Clin Pract Neurol 4(4, 2008):190-201]. The electrical stimulation countermeasures that have been proposed involved deep-brain stimulation or other uses of implanted electrodes, including implanted vagus nerve stimulators, but not non-invasive vagal nerve stimulation. Non-invasive magnetic stimulation has also been proposed, but not of the vagus nerve. [THEODORE W H, Fisher R. Brain stimulation for epilepsy. Acta Neurochir Suppl. 97(2, 2007):261-72]. Most electrical stimulation countermeasures involve open-loop devices, meaning that there is no direct feedback to the electrical stimulator from sensors that can be used to forecast or monitor the epileptic seizure. More recently, closed-loop stimulators have also been described wherein there may be feedback to the electrical stimulator from the sensors. Closed-loop therapy has the potential advantage that it may be precisely timed or dosed to be administered only when and where needed, for example, administered immediately upon or before seizure detection, directly to the site of seizure origin and with variable dose depending upon detected seizure characteristics [U.S. Pat. No. 6,480,743, entitled System and method for adaptive brain stimulation, to Kirkpatrick et al; U.S. Pat. No. 7,231,254, entitled Closed-loop feedback-driven neuromodulation, to DiLorenzo; U.S. Pat. No. 7,209,787, entitled Apparatus and method for closed-loop intracranial stimulation for optimal control of neurological disease, to DiLorenzo].

It should be noted that some patients are able to predict their own epileptic seizures well in advance, and some are able to do so reliably [HAUT S R, Hall C B, LeValley A J, Lipton R B. Can patients with epilepsy predict their seizures? Neurology. 68(4, 2007):262-6; STACEY W C, Litt B. Technology insight: neuroengineering and epilepsy-designing devices for seizure control. Nat Clin Pract Neurol 4(4, 2008):190-201]. Accordingly, one aspect of the present invention comprises the steps of (1) a patient predicts his/her own epileptic seizure, or a device predicts the seizure using data obtained from EEG devices plus accessory noninvasive data (e.g., heart rate, and motion), as described in publications such as the ones cited above; and (2) the patient or a caregiver performs noninvasive vagal nerve stimulation using devices that are disclosed herein. The rationale for performing the vagal nerve stimulation is that it is already an adjunctive therapy for pharmaco-resistant partial epilepsy, having been approved since 1997 by the FDA. This includes the use of vagal nerve stimulation performed on-demand by the epileptic patient [BOON, P., Vonck, K., Van Walleghem, P., D'Have, M., Goossens, L., Vandekerckhove, T., Caemaert, J., De Reuck, J., Programmed and magnet-induced vagus nerve stimulation for refractory epilepsy. J. Clin. Neurophysiol. 18(2001):402-407; MORRIS III, G. L., 2003. A retrospective analysis of the effects of magnet-activated stimulation in conjunction with vagus nerve stimulation therapy. Epilepsy Behav. 4(2003): 740-745]. A novelty of the present disclosure is that the vagus nerve stimulation is performed noninvasively and in anticipation of an imminent attack. Furthermore, a novel "closed-loop" strategy for selecting the parameters in FIG. 2 was disclosed above in connection with tuning of a controller, in which several alternate sets of stimulator values are available for use.

In another application of the invention, the non-invasive vagus nerve stimulators disclosed herein can be used chronically and prophylactically by a caregiver or the patient to limit or prevent seizures. Implantable vagus nerve stimulators, such as those described above, have been used for years to minimize or eliminate epileptic seizures. However, these devices must be implanted into the patient's neck, which is a costly, invasive and permanent procedure. With the present invention, the patient can stimulate his/her vagus nerve non-invasively on a regular basis every day to obtain the same results as those obtained by the implantable VNS devices. In this aspect of the invention, the patient would work with her/her physician to determine the appropriate number and intervals for non-invasive stimulation to effectively limit or prevent seizures. In addition, if the patient experiences prodromal symptoms that a seizure is about to occur, he/she can use the non-invasive device immediately to acutely limit or prevent the seizure from occurring.

Methods for Averting Imminent Migraine Headaches

The pathophysiology of migraine and other sudden-onset headaches was described in the co-pending, commonly assigned application ELECTRICAL AND MAGNETIC STIMULATORS USED TO TREAT MIGRAINE/SINUS HEADACHE AND COMORBID DISORDERS. As described there, migraine attacks are often thought to be triggered by environmental, physiological, and/or cognitive sets of events. The patient may also need to be in a permissive physical and mental state for the trigger to be effective. Thus, the migraine may be triggered by a situation or thought, but a physiologically measurable permissive state that is detectable shortly before the attack may also be required, and detection of that permissive state may be used to forecast that an attack is imminent. Triggers for migraine attacks (also called precipitating factors) were described in the above-cited commonly-assigned patent application and comprise: stress and negative emotions; hormonal factors for females (menstruation, menopause, pregnancy, use of oral contraceptives, and hormone replacement therapy); flicker, glare and eyestrain; noise; odors (exhaust fumes, cleaning solutions, perfume); hunger and thirst (skipped meals, delayed meals, fasting, dehydration, withdrawal of reactive foods and drinks, particularly caffeinated); consumption of certain foods (e.g., chocolate, monosodium glutamate, pungent foods) and alcohol; weather (cold, heat, high humidity, sudden changes in weather, allergens such as pollen); fatigue; and lack of sleep or too much sleep [Burstein R, Jakubowski M. A unitary hypothesis for multiple triggers of the pain and strain of migraine. J Comp Neurol 493(2005):9-14; Vincent T. Martin, Michael M. Behbehani. Towards a rational understanding of migraine trigger factors. Medical Clinics of North America 85(4, 2001): 911-41].

An objective of the present invention is to forecast the onset of a migraine attack, wherein ambulatory sensors placed on or about the patient are used to make the forecast. If a patient is particularly sensitive to one of the triggers listed above, then a sensor directed to that trigger should be used. Otherwise, the most frequently cited trigger for migraine attacks is said to be stress and negative emotions, so sensors that may detect stress are important. These include sensors intended specifically to detect stress [VAVRINSKY, E.; Stopjakova, V.; Majer, L. Electrical biomonitoring towards mobile diagnostics of human stress influence. 2nd International Symposium on Applied Sciences in Biomedical and Communication Technologies, 2009. ISABEL 2009: 1-6; U.S. Pat. No. 7,918,780 Apparatus for measuring acute stress, to El-Nokaly]. More generally, traditional physiological sensors may be used to detect stress symptoms associated with changes in the autonomic nervous system. These include noninvasive ambulatory recordings of respiration (abdominal and thoracic plethysmography), carbon dioxide (capnometry with nasual cannula), heart rate (electrocardiogram leads), skin impedance (electrodermal leads), vocalization and ambient sound (microphones), light (light sensor), motion (accelerometer), external and finger temperature (thermometers), and patient-reported events (event marker button). The sensors may be embedded in garments or placed in sports wristwatches, as currently used in programs that monitor the physiological status of soldiers [G. A. Shaw, A. M. Siegel, G. Zogbi, and T. P. Opar. Warfighter physiological and environmental monitoring: a study for the U.S. Army Research Institute in Environmental Medicine and the Soldier Systems Center. MIT Lincoln Laboratory, Lexington Mass. 1 Nov. 2004, pp. 1-141].

Because the mental state of the patient may also be an important predictor of an imminent migraine, sensors directed to brain monitoring may also be useful for making a forecast. For brain monitoring, ambulatory recording may comprise ambulatory EEG sensors [Casson A, Yates D, Smith S, Duncan J, Rodriguez-Villegas E. Wearable electroencephalography. What is it, why is it needed, and what does it entail? IEEE Eng Med Biol Mag. 29(3, 2010):44-56] or optical topography systems for mapping prefrontal cortex activation [Atsumori H, Kiguchi M, Obata A, Sato H, Katura T, Funane T, Maki A. Development of wearable optical topography system for mapping the prefrontal cortex activation. Rev Sci Instrum. 2009 April; 80(4):043704].

Internal chemistry may also be a useful predictor of an imminent migraine attack, particularly migraineurs who experience an aura. Sensors that measure bodily chemicals noninvasively may make use of transdermal reverse iontophoresis [Leboulanger B, Guy R H, Delgado-Charro M B. Reverse iontophoresis for non-invasive transdermal monitoring. Physiol Meas. 25(3, 2004):R35-50]. Particular chemicals that may be relevant to the pathophysiology of a migraine attack and that may be measured by transdermal reverse iontophoresis comprise potassium, glutamate, stress hormones (e.g., ACTH and/or cortisol), and glucose.

Airborne irritants that may trigger a migraine attack may also be measured non-invasively in real time around an ambulatory patient [Kirk J. Englehardt and John Toon. Asthma attack: Vest-based sensors monitor environmental exposure to help understand causes: web page (www) at the Georgia Tech Research Institute (.gtri) of Georgia Tech (.gatech) educational domain (.edu) in subdomain: /casestudy/asthma-vest-helps-id-asthma-causes; patent application US20110144515 Systems and methods for providing environmental monitoring, to Bayer et al.; and U.S. Pat. No. 7,119,900; entitled Pollen sensor and method, to Okumura et al]. For physical external irritants, the unit of irritation should be selected accordingly, such as temperature for cold air as an irritant.

The disclosed invention comprises forecasting an imminent migraine attack. A training set of ambulatory recordings is acquired using sensors such as those described above. The training set will also include the measurement of the migraine attack onset itself (e.g., from patient activated event markers). All those recordings are used to parameterize a model that predicts the imminent onset of the migraine attack. In use, the model also measures the ambulatory signals, but then calculates the likelihood of an imminent attack, and warns the patient when a migraine attack is imminent.

Many such forecasting models may used. They comprise autoregressive models [Tim BOLLERSLEV. Generalized autoregressive condiditional heteroskedasticity. Journal of Econometrics 31(1986):307-327], or those that make use of principal components [James H. STOCK, Mark W. Watson. Forecasting with Many Predictors, In: Handbook of Economic Forecasting. Volume 1, G. Elliott, C. W. J. Granger and A. Timmermann, eds (2006) Amsterdam: Elsevier B. V, pp 515-554], Kalman filters [Eric A. WAN and Rudolph van der Merwe. The unscented Kalman filter for nonlinear estimation, In: Proceedings of Symposium 2000 on Adaptive Systems for Signal Processing, Communication and Control (AS-SPCC), IEEE, Lake Louise, Alberta, Canada, October, 2000, pp 153-158], wavelet transforms [O. RENAUD, J.-L. Stark, F. Murtagh. Wavelet-based forecasting of short and long memory time series. Signal Processing 48(1996):51-65], hidden Markov models [Sam ROWEIS and Zoubin Ghahramani. A Unifying Review of Linear Gaussian Models. Neural Computation 11(2, 1999): 305-345], or artificial neural networks [Guoquiang ZHANG, B. Eddy Patuwo, Michael Y. Hu. Forecasting with artificial neural networks: the state of the art. International Journal of Forecasting 14(1998): 35-62].

The preferred forecasting model will be one that makes use of support vector machines. In the present context, a training set of physiological data will have been acquired that includes whether or not the patient is experiencing a migraine attack. Thus, the classification of the patient's state is whether or not an attack is in progress, and the data used to make the classification consist of the remaining acquired physiological data, evaluated at Δ time units prior to the time at which the attack data are acquired. Thus, the SVM is trained to forecast the imminence of an attack Δ time units into the future. After training the SVM, it is implemented as part of the controller to sound an alarm and advise the use of vagus nerve stimulation, whenever there is a forecast of an imminent attack [Christopher J. C. BURGES. A tutorial on support vector machines for pattern recognition. Data Mining and Knowledge Discovery 2(1998), 121-167; J. A. K. Suykens, J. Vandewalle, B. De Moor. Optimal Control by Least Squares Support Vector Machines. Neural Networks 14 (2001):23-35; Sapankevych, N. and Sankar, R. Time Series Prediction Using Support Vector Machines: A Survey. IEEE Computational Intelligence Magazine 4(2, 2009): 24-38; Press, W H; Teukolsky, S A; Vetterling, W T; Flannery, B P (2007). Section 16.5. Support Vector Machines. In: Numerical Recipes: The Art of Scientific Computing (3rd ed.). New York: Cambridge University Press].

The patient or a caregiver then performs noninvasive vagus nerve stimulation as a prophylactic countermeasure as disclosed herein, the rationale for which is described more fully in the co-pending, commonly assigned applications ELECTRICAL AND MAGNETIC STIMULATORS USED TO TREAT MIGRAINE/SINUS HEADACHE AND COMORBID DISORDERS and ELECTRICAL AND MAGNETIC STIMULATORS USED TO TREAT MIGRAINE/SINUS HEADACHE, RHINITIS, SINUSITIS, RHINOSINUSITIS, AND COMORBID DISORDERS.

Methods for Averting Imminent Transient Ischemic Attacks and Strokes

Migraineurs are at a significantly increased risk for experiencing strokes, so the prevention of migraine headaches may also decrease the likelihood of stroke [MacCLELLAN L R, Giles W, Cole J, Wozniak M, Stern B, Mitchell B D, Kittner S J. Probable migraine with visual aura and risk of ischemic stroke: the stroke prevention in young women study. Stroke 38(9, 2007):2438-45]. A stroke is the acute loss of brain function due to loss of normal blood supply to the brain. This can be due to the lack of blood flow (ischemia) caused by blockage due to thrombosis or arterial embolism, or to a hemorrhage. Ischemic stroke occurs in 87% of stroke patients may be treated with thrombolytic agents ("clot busters"). Hemorrhagic strokes occur in 13% of stroke patients and may benefit from neurosurgery.

A transient ischemic attack (TIA) is also caused by ischemia in the brain, spinal cord or retina. TIAs share the same underlying etiology as strokes and produce the same symptoms, such as contralateral paralysis, sudden weakness or numbness, dimming or loss of vision, aphasia, slurred speech and mental confusion. Unlike a stroke, the symptoms of a TIA can resolve typically within a day, whereas the symptoms from a stroke can persist due to death of neural tissue (acute infarction) [PRABHAKARAN S. Reversible brain ischemia: lessons from transient ischemic attack. Curr Opin Neurol 20(1, 2007):65-70].

Prediction that a stroke or TIA is imminent may be based upon the likely formation of a thrombosis or arterial embolism. In that regard, there exists an ambulatory monitoring device that will monitor for cerebral emboli [MacKINNON A D, Aaslid R, Markus H S. Long-term ambulatory monitoring for cerebral emboli using transcranial Doppler ultrasound. Stroke 35(1, 2004):73-8]. It measures the passage of emboli, typically at the middle cerebral artery, using a transcranial Doppler signal. Whereas some cerebral emboli produce symptoms such as those listed above in connection with the symptoms of a stroke, other emboli do not produce symptoms and may not be recognized by the patient. Therefore, in one embodiment, of the invention, the detection of an embolus with the device mentioned above is used as input for the forecasting of a TIA or stroke, but the appearance of the embolus in and of itself does not necessarily trigger the forecast of an imminent TIA or stroke.

Risk factors for the formation of emboli include carotid stenosis and atrial fibrillation, the latter of which may start and stop in paroxysmal atrial fibrillation. In fact, the onset of atrial fibrillation itself may be forecast as described in a following section. In addition to these risk factors, there are many others that are thought to predispose a patient to having a stroke or TIA. These include infection and inflammation, recreational drugs and medications, mental stress, perturbations in systemic metabolism, acute increases in blood pressure, and changes in coagulation [ELKIND M S.

Why now? Moving from stroke risk factors to stroke triggers. Curr Opin Neurol 20(1, 2007):51-7]. One may monitor these risk factors noninvasively using the same ambulatory sensors described above in connection with the forecasting of migraine, including an ECG for monitoring for the presence of atrial fibrillation, ambulatory blood pressure monitors for the presence of acute increases in blood pressure, and body temperature thermometers for the presence of infection and inflammation. For the monitoring of drug and medications, systemic metabolism, and changes in coagulation, body chemistry may also be measure noninvasively using transdermal reverse iontophoresis [Leboulanger B, Guy R H, Delgado-Charro M B. Reverse iontophoresis for non-invasive transdermal monitoring. Physiol Meas 25(3, 2004):R35-50].

The disclosed invention comprises forecasting an imminent TIA or stroke. A training set of ambulatory recordings is acquired using sensors such as those described above, and the training set will also include the measurement of TIA or stroke onset (e.g., from patient activated event markers upon the appearance of symptoms such as sudden weakness or numbness, dimming or loss of vision). Measurements may include those for the passage of emboli, for example at the middle cerebral artery, using the transcranial Doppler ultrasound device that was described above. The detection of an embolus with this device is used as input for the forecasting of a TIA or stroke, but the appearance of the embolus does not in and of itself necessarily trigger the forecast of an imminent TIA or stroke. The set of all training measurements is then used to parameterize a model that predicts the imminent onset of the TIA or stroke. When the parameterized model is in use after training of the model, the signals are also acquired, then the model calculates the likelihood of an imminent stroke using the acquired data and warns the patient when a stroke or TIA may be imminent.

Many such forecasting models may used. They comprise autoregressive models [Tim BOLLERSLEV. Generalized autoregressive condiditional heteroskedasticity. Journal of Econometrics 31(1986):307-327], or those that make use of principal components [James H. STOCK, Mark W. Watson. Forecasting with Many Predictors, In: Handbook of Economic Forecasting. Volume 1, G. Elliott, C. W. J. Granger and A. Timmermann, eds (2006) Amsterdam: Elsevier B. V, pp 515-554], Kalman filters [Eric A. WAN and Rudolph van der Merwe. The unscented Kalman filter for nonlinear estimation, In: Proceedings of Symposium 2000 on Adaptive Systems for Signal Processing, Communication and Control (AS-SPCC), IEEE, Lake Louise, Alberta, Canada, October, 2000, pp 153-158], wavelet transforms [O. RENAUD, J.-L. Stark, F. Murtagh. Wavelet-based forecasting of short and long memory time series. Signal Processing 48(1996):51-65], hidden Markov models [Sam ROWEIS and Zoubin Ghahramani. A Unifying Review of Linear Gaussian Models. Neural Computation 11(2, 1999): 305-345], or artificial neural networks [Guoquiang ZHANG, B. Eddy Patuwo, Michael Y. Hu. Forecasting with artificial neural networks: the state of the art. International Journal of Forecasting 14(1998): 35-62].

The preferred forecasting model will be one that makes use of support vector machines (SVM). In the present context, a training set of physiological data will have been acquired that includes whether or not the patient is experiencing a stroke or TIA. Thus, the classification of the patient's state is whether or not a stroke is in progress, and the data used to make the classification consist of the remaining acquired physiological data, evaluated at $\Delta$ time units prior to the time at which the stroke data are acquired. Consequently, the SVM is trained to forecast the imminence of a stroke $\Delta$ time units into the future. After training the SVM, it is implemented as part of the controller to sound an alarm and advise the use of vagal nerve stimulation, whenever there is a forecast of an imminent stroke [Christopher J. C. BURGES. A tutorial on support vector machines for pattern recognition. Data Mining and Knowledge Discovery 2(1998), 121-167; J. A. K. Suykens, J. Vandewalle, B. De Moor. Optimal Control by Least Squares Support Vector Machines. Neural Networks 14 (2001):23-35; Sapankevych, N. and Sankar, R. Time Series Prediction Using Support Vector Machines: A Survey. IEEE Computational Intelligence Magazine 4(2, 2009): 24-38; Press, W H; Teukolsky, S A; Vetterling, W T; Flannery, B P (2007). Section 16.5. Support Vector Machines. In: Numerical Recipes: The Art of Scientific Computing (3rd ed.). New York: Cambridge University Press].

The patient or a caregiver then performs noninvasive vagal nerve stimulation as a prophylactic countermeasure using devices and methods disclosed herein, the rationale for which is described more fully in the publication: MRAVEC B. The role of the vagus nerve in stroke. Auton Neurosci 158(1-2, 2010):8-12.

Methods for Averting Imminent Atrial Fibrillation

Atrial fibrillation (AF) is a common cardiac arrhythmia, in which the normal electrical impulses that are generated by the sinoatrial node of the heart are inundated by disorganized electrical impulses that originate in the atria and pulmonary veins, leading to the conduction of irregular impulses to the ventricles that generate the heartbeat. Individuals with AF usually have a significantly increased risk of stroke, which increases during AF because blood may pool and form clots in the poorly contracting atria. The risk of a stroke increases when patients have a previous ischemic stroke, hypertension, diabetes, congestive heart failure, and an age greater than 75 years. The risk also increases as a function of the length of time that the atrium is fibrillating.

When atrial fibrillation self-terminates, generally within a week, it is known as paroxsysmal atrial fibrillation. However, atrial fibrillation may also become a persistent or permanent arrhythmia, in which case medications, electrical cardioversion, or surgical ablation is often attempted in order to convert the atrial fibrillation back into a normal heart rhythm. Patients with atrial fibrillation are also often treated with warfarin or other anticoagulants, at which time they must follow a restricted diet. Some, but not all, patients with artial fibrillation experience discomfort as the atrium fibrillates, especially if the heart rate is high.

Atrial fibrillation is a type of bistable state. Once the atrial fibrillation starts, it may be difficult to cardiovert it back into normal sinus rhythm. On the other hand, if a patient is currently in normal sinus rhythm, it may take a triggering event or circumstance to make the transition into atrial fibrillation. Thus, the pathophysiology of atrial fibrillation consists of both a triggering focal activator and changes in the atrial electrophysiologic properties capable of maintaining AF.

Accordingly, one strategy for managing patients who are at risk of transitioning to atrial fibrillation from normal sinus rhythm is to predict that the onset of AF is imminent, and then used a countermeasure to avert the AF. The countermeasure might be one used to treat atrial fibrillation that is in progress, such as the administration of a beta blocker or calcium channel blocker drug. According to the present invention, a preferred countermeasure comprises the administration of low level vagus nerve stimulation. One rationale for performing vagus nerve stimulation is that transient changes in vagal outflow are temporally related to the onset of AF [Vikman S, Lindgren K, Mäkikallio T H, Yli-Mäyry S, Airaksinen K E, Huikuri H V. Heart rate turbulence after atrial premature beats before spontaneous onset of atrial fibrillation. J Am Coll Cardiol. 45(2, 2005):278-84].

Several methods have been proposed to predict the imminent onset of atrial fibrillation. The prediction is made from an analysis of an electrocardiogram of the patient over an extended period of time, which requires the patient to wear a monitoring device similar to a Holter monitor. Measurement of respiration using noninvasive inductive plethysmography, mercury in silastic strain gauges or impedance pneumography may also be advised, in order to account for the effects of respiration on the heart rate. A noninvasive accelerometer may also be included among the ambulatory sensors in order to account for motion artifacts, and although AF can be detected from the ECG alone, an event marker may also be included in order for the patient to mark relevant circumstances and sensations.

Most AF prediction methods involve an analysis of heart rate variability [VIKMAN S, Mäkikallio TH, Yli-Mäyry S, Pikkujämsä S, Koivisto A M, Reinikainen P, Airaksinen K E, Huikuri H V. Altered complexity and correlation properties of R—R interval dynamics before the spontaneous onset of paroxysmal atrial fibrillation. Circulation 100(20, 1999): 2079-84]. Some AF prediction methods evaluate rates of atrial and ventricular depolarization [Patent application US20040148109, entitled Method and apparatus for prediction of cardiac dysfunction, to Fischer], and others take into account the effects of circadian rhythm on the onset of AF [Patent application US20100145208, entitled Device For Predicting Tachyarrhythmias And/Or Atrial Arrhythmias, to Schirdewan]. A related problem that has been studied is prediction of the termination of atrial fibrillation once it has started, so that unnecessary treatment of self-terminating AF may be avoided [Nilsson F, Stridh M, Bollmann A, Sörnmo L. Predicting spontaneous termination of atrial fibrillation using the surface ECG. Med Eng Phys. 28(8, 2006):802-808].

At one time, stimulation of the vagus nerve was considered to exacerbate rather than ameliorate the dangers of AF, but this is no longer the case, provided that parameters of the vagal nerve stimulation are properly selected [ZHANG Y, Mazgalev T N. Arrhythmias and vagus nerve stimulation. Heart Fail Rev 16(2, 2011):147-61; ZHANG Y, Ilsar I, Sabbah H N, Ben David T, Mazgalev T N. Relationship between right cervical vagus nerve stimulation and atrial fibrillation inducibility: therapeutic intensities do not increase arrhythmogenesis. Heart Rhythm. 6(2, 2009):244-50].

Accordingly, one embodiment of the present invention comprises the following steps: (1) a device predicts the imminent onset of atrial fibrillation using data obtained from the electrocardiogram plus accessory noninvasive data (e.g., respiration and motion), for example, as described in publications such as the ones cited above; and (2) the patient or a caregiver performs noninvasive vagal nerve stimulation using devices that are disclosed herein. Novelty of the present disclosure comprises the fact that the vagal nerve stimulation is performed noninvasively and in anticipation of imminent AF. The stimulation protocol comprises low-level right-side or both-side vagal stimulation, as a prophylactic countermeasure, a rationale for which is described more fully in the publications: LI S, Scherlag B J, Yu L, Sheng X, Zhang Y, Ali R, Dong Y, Ghias M, Po S S. Low-level vagosympathetic stimulation: a paradox and potential new modality for the treatment of focal atrial fibrillation. Circ Arrhythm Electrophysiol 2(6, 2009):645-51; SHA Y, Scherlag B J, Yu L, Sheng X, Jackman W M, Lazzara R, Po S S. Low-Level Right Vagal Stimulation: Anticholinergic and Antiadrenergic Effects. J Cardiovasc Electrophysiol 22(10, 2011):1147-53; SHENG X, Scherlag B J, Yu L, Li S, Ali R, Zhang Y, Fu G, Nakagawa H, Jackman W M, Lazzara R, Po S S. Prevention and reversal of atrial fibrillation inducibility and autonomic remodeling by low-level vagosympathetic nerve stimulation. J Am Coll Cardiol 57(5, 2011):563-71; YU L, Scherlag B J, Li S, Sheng X, Lu Z, Nakagawa H, Zhang Y, Jackman W M, Lazzara R, Jiang H, Po S S. Low-level vagosympathetic nerve stimulation inhibits atrial fibrillation inducibility: direct evidence by neural recordings from intrinsic cardiac Ganglia. J Cardiovasc Electrophysiol 22(4, 2011):455-63; BRACK K E, Coote J H, Ng G A. Vagus nerve stimulation protects against ventricular fibrillation independent of muscarinic receptor activation. Cardiovasc Res 91(3, 2011):437-46.

Methods for Averting Imminent Myocardial Infarction

Myocardial infarction (a heart attack), is the interruption of blood supply and oxygen to a part of the heart, resulting in heart muscle death (infarction). It is most commonly due to blockage of a coronary artery, by a thrombus following the rupture of a vulnerable atherosclerotic plaque, which is an unstable collection of lipids and white blood cells (particularly macrophages) in the wall of an artery. In order to predict that a myocardial infarction is imminent, it is therefore necessary to determine that vulnerable atherosclerotic plaques exist, and that their rupture is imminent [Culic V. Acute risk factors for myocardial infarction. Int J Cardiol 117(2, 2007):260-9; TOFLER G H, Muller J E. Triggering of acute cardiovascular disease and potential preventive strategies. Circulation 114(17, 2006):1863-72]. In addition, vulnerability to' thrombosis and vulnerability of the myocardium to arrhythmia needs to be assessed [NAGHAVI M et al. From vulnerable plaque to vulnerable patient: a call for new definitions and risk assessment strategies: Part II. Circulation 108(15, 2003):1772-8]. In that regard, WONG describes a device that attributes the risk of myocardial infarction to a heart rate at which angina has previously been experienced [Patent application US20100081951, entitled Device for identifying the likelihood of a patient suffering a myocardial infarction, to WONG].

The detection of various biomarkers may be used to determine the progression of atherosclerotic plaque vulnerability and rupture, comprising: endothelial dependent vasodilation (FMD) for endothelial dysfunction; adhesion molecules for endothelial activation; macrophages for inflammation; MMPs and cathepsin for proteolysis and apoptosis; lipid core fibrous cap; alphaV-beta3 integrin for angiogenesis; and fibrin, platelets, and tissue factor for thrombosis [SHAH P K. Mechanisms of plaque vulnerability and rupture. J Am Coll Cardiol 41(4 Suppl S, 2003): 15S-22S; VIRMANI R, Kolodgie F D, Burke A P, Finn A V, Gold H K, Tulenko T N, Wrenn S P, Narula J. Atherosclerotic plaque progression and vulnerability to rupture: angiogenesis as a source of intraplaque hemorrhage. Arterioscler Thromb Vasc Biol 25(10, 2005):2054-61; CHAN D, Ng L L. Biomarkers in acute myocardial infarction. BMC Med 8(2010):34. pp 1-11].

Several noninvasive imaging methods exist for detecting and evaluating vulnerable coronary plaques, but currently, most of those methods are not well suited to ambulatory monitoring [Jan G. KIPS, Patrick Segers, Luc M. Van Bortel. Identification of the vulnerable plaque: a review of invasive and non-invasive imaging modalities. Artery Research 2(2008):21-34; BRAUNWALD E. Noninvasive detection of vulnerable coronary plaques: Locking the barn door before the horse is stolen. J Am Coll Cardiol 54(1, 2009):58-9].

However, noninvasive ambulatory detection of molecules involved in atherogenesis, plaque progression and vulnerability, and thrombosis can be accomplished by using radioactive tracers that accumulate in plaques within the heart [VALLABHAJOSULA S, Fuster V. Atherosclerosis: imaging techniques and the evolving role of nuclear medicine. J Nucl Med 1997; 38: 1788-96; Manca G, Parenti G, Bellina R, Boni G, Grosso M, Bernini W, Palombo C, Paterni M, Pelosi G, Lanza M, Mazzuca N, Bianchi R, De Caterina R. 111In platelet scintigraphy for the noninvasive detection of carotid plaque thrombosis. Stroke. 2001 March; 32(3):719-27; Annovazzi A, Bonanno E, Arca M, D'Alessandria C, Marcoccia A, Spagnoli L G, Violi F, Scopinaro F, De Toma G, Signore A. 99mTc-interleukin-2 scintigraphy for the in vivo imaging of vulnerable atherosclerotic plaques. Eur J Nucl Med Mol Imaging. 2006 February; 33(2):117-26; HUBALEWSKA-DYDEJCZYK A, Stompór T, Kalembkiewicz M, Krzanowski M, Mikolajczak R, Sowa-Staszczak A, Tabor-Ciepiela B, Karczmarczyk U, Kusnierz-Cabala B, Sulowicz W. Identification of inflamed atherosclerotic plaque using 123 I-labeled interleukin-2 scintigraphy in high-risk peritoneal dialysis patients: a pilot study. Perit Dial Int 29(5, 2009):568-74].

The accumulation of those radio-labeled probes may be measured in the heart in real time, within an ambulatory patient who wears a vest having a small nuclear detector located above the patient's heart [BROARDHURST P, Cashin P, Crawley J, Raftery E, Lahiri A. Clinical validation of a miniature nuclear probe system for continuous on-line monitoring of cardiac function and ST-segment. J Nucl Med 32(1991):37-43]. Such a device may therefore be used to predict imminent plaque rupture and a subsequent heart attack, whenever the detected radio-labeled probe exceeds a predetermined, critical measurement value. For example, the critical value could be set based upon the experience with patients who actually suffer a myocardial infarction when being monitored, at which time there will ordinarily be an abrupt change in the probe's signal. The critical value may also be based on the measurement of additional noninvasive signals such as heart rate, blood pressure, respiration, and the like, as in the case of the forecasting of a stroke or TIA, wherein a preferred forecasting model would be one that makes use of support vector machines and training sets of ambulatory data.

It is understood that at the selected critical value, the plaque may progress to rupture, stabilize, or even eventually regress, depending on the presence or absence of other factors that would promote or inhibit progression to rupture. Therefore, when the device warns the patient that a heart attack may be imminent, the patient should (1) stop or avoid activities that may contribute to the progression to plaque rupture, such as stopping any physical activity, seek a warmer environment if the current environment is cold, avoid emotionally stressful situations such as driving or arguing, and have thrombolytic agents on hand as a precaution; and (2) as a prophylactic countermeasure, perform noninvasive vagus nerve stimulation with a device such as those disclosed herein.

The rationale for performing vagus nerve stimulation is that it can inhibit cytokine release by inflammatory cells, promote the dilation of a vasoconstricted blood vessel, and promote beneficial hemodynamic effects that counteract a surge in blood pressure or heart rate, as described elsewhere in this disclosure, in the co-pending, commonly assigned applications cited in the section CROSS REFERENCE TO RELATED APPLICATIONS and in TOFLER G H, Muller J E. Triggering of acute cardiovascular disease and potential preventive strategies. Circulation. 114(17, 2006):1863-72.

Methods for Averting Imminent Ventricular Fibrillation or Ventricular Tachycardia Detecting the onset of cardiac arrhythmia, such as ventricular fibrillation and ventricular tachycardia, is a well-known physiological monitoring problem for which there are many proposed solutions. Devices that implement a ventricular fibrillation-detection algorithm include the wearable cardiac defibrillator vest, the implanted cardioverter defibrillator (ICD), and devices that can act as both pacemaker and defibrillator, including cardiac resynchronization therapy (CRT-D) devices. They may also detect the absence of ventricular fibrillation, so as to terminate the defibrillation shock once it has had its intended effect.

Such devices are activated to shock the patient's heart only after fibrillation is actually detected. Devices that would shock the patient prior to ventricular fibrillation or tachycardia, in anticipation of a forecasted fibrillation event, are not used. This is presumably because the considerable pain that accompanies a defibrillation shock would contraindicate a shock based only on a forecasted fibrillation event, which may have a significant likelihood of being a false positive.

In fact, few defibrillation algorithms even include a method for forecasting the likely onset of ventricular fibrillation, as distinguished from only detection of ventricular fibrillation in progress. An exception is the algorithm described by SMALL, which is not intended to be placed only in a defibrillator [Michael SMALL. Application: detecting ventricular arrhythmia. pp 69-74 In: Applied Nonlinear Time Series Analysis: Applications in Physics, Physiology and Finance. Singapore: World Scientific Series on Nonlinear Science, Series A, Vol. 52, 2005]. SMALL's application is instead concerned with the bedside monitoring of cardiac patients, in which it is desired to begin the recording and intense analysis of voluminous ECG data from a patient, but only when a fibrillation event appears to be imminent. The algorithm predicts imminent fibrillation when there is significant 3-6 Hz content in the ECG signal as well as a signal from a nonlinear complexity measurement indicating that the ECG signal cannot be compressed without losing the ability to predict the timing of future heart beats. Recording is typically triggered approximately one minute before the ventricular fibrillation, but the lead time may be as short as only a few seconds.

Other such forecasting algorithms have also been described, some of which are suitable for use with ambulatory measurement [MAKIKALLIO T H, Koistinen J, Jordaens L, Tulppo M P, Wood N, Golosarsky B, Peng C K, Goldberger A L, Huikuri H V. Heart rate dynamics before spontaneous onset of ventricular fibrillation in patients with healed myocardial infarcts. Am J Cardiol 83(6, 1999):880-4; WESSEL, N. Meyerfeldt, U. Schirdewan, A. Kurths, J. Voss, A. Short-term forecasting of life-threatening arrhythmias with finite time Lyapunov exponents. Proceedings of the 20th Annual International Conference of the IEEE Engineering in Medicine and Biology Society, 20(1, 1998):326-329; U.S. Pat. No. 5,437,285, entitled Method and apparatus for prediction of sudden cardiac death by simultaneous assessment of autonomic function and cardiac electrical stability, to Verrier et al.; U.S. Pat. No. 7,822,474, entitled Methods for the prediction of arrhythmias and prevention of sudden cardiac death, to Chen; and U.S. Pat. No. 6,516,219, entitled Arrhythmia forecasting based on morphology changes in intracardiac electrograms, to Street; U.S. Pat. No. 5,749,900, U.S. Pat. No. 6,035,233, U.S. Pat. No. 6,144,878 and U.S. Pat. No. 6,571,121, entitled Implantable medical device responsive to heart rate variability analysis, to Schroeppel et al.; U.S. Pat. No. 7,822,474, entitled Methods for the prediction of arrhythmias and prevention of sudden cardiac death, to Chen; U.S. Pat. No. 7,266,410 and U.S. Pat. No. 7,725,178, entitled Method and system for the prediction of cardiac arrhythmias, myocardial ischemia, and other diseased condition of the heart associated with elevated sympathetic neural discharges, to Chen et al.; Patent application US20090076339, entitled Method and device for predicting abnormal medical events and/or assisting in diagnosis and/or monitoring, particularly in order to determine depth of anesthesia, to Quintin et al.; US20100268289, entitled Method and system for the prediction of cardiac arrhythmias, myocardial ischemia, and other diseased conditions of the heart associated with elevated sympathetic neural discharges, to Chen et al].

For patients who do not have an implanted defibrillator, such a forecast of imminent fibrillation may be used to advise defibrillation as a prophylactic measure, because the patient may be unable to shock him/herself once fibrillation is in progress. However, the patient may prefer not to do so because the forecast may be a false positive, and a prophylactic defibrillation shock would be painful and possibly unsafe.

As an alternative, the present invention discloses noninvasive vagal nerve stimulation as a prophylactic method for patients in whom monitoring algorithms, such as the one described by SMALL, predict that ventricular fibrillation or ventricular tachycardia may be imminent. The rationale is that vagal nerve stimulation protects against ventricular fibrillation, as described in the publications: [ZHANG Y, Mazgalev T N. Arrhythmias and vagus nerve stimulation. Heart Fail Rev 16(2, 2011):147-61; BRACK K E, Coote J H, Ng G A. Vagus nerve stimulation protects against ventricular fibrillation independent of muscarinic receptor activation. Cardiovasc Res 91(3, 2011):437-46]. Thus, a patient will wear a monitor of heartrate or ECG; an algorithm such as the one by SMALL will use signals from the monitor to forecast imminent fibrillation; an audio or other signal will be emitted by the monitoring equipment advising the patient or healthcare provider to perform vagus nerve stimulation; and the patient will be stimulated with a noninvasive stimulator so as to avoid the forecasted arrhythmia, using a simulator such as ones disclosed here.

Unlike the present invention, the above-mentioned BRACK and ZHANG publications do not suggest the use of vagus nerve stimulation in patients for whom imminent fibrillation is forecast. Instead, they are concerned only with implanted stimulators and with regularly scheduled stimulation. Furthermore, the presently disclosed use of noninvasive vagal nerve stimulation could not have occurred to the authors of those publications, because relatively painless noninvasive vagal nerve stimulators have only been disclosed in the patent applications that are cited in the section CROSS REFERENCE TO RELATED APPLICATIONS.

Methods for Averting Imminent Panic Attacks

MEURET reported that panic attacks may be predicted as little as 47 minutes before they occur, by analyzing noninvasive ambulatory recordings of respiration (abdominal and thoracic plethysmography), carbon dioxide (capnometry with nasual cannula), heart rate (electrocardiogram leads), skin impedance (electrodermal leads), vocalization (microphones), light (light sensor), motion (accelerometer), external and finger temperature (thermometers), and patient-reported events (event marker button) [MEURET A E, Rosenfield D, Wilhelm F H, Zhou E, Conrad A, Ritz T, Roth W T. Do Unexpected Panic Attacks Occur Spontaneously? Biol Psychiatry. 2011 Jul. 21, Epub ahead of print]. Some attacks were cued (driving in traffic, engaged in argument) but most were not. Hyperventilation and increased heart rate were generally noted at times closer to the attack itself.

The disclosed invention comprises forecasting an imminent panic attack as was done by MUERET et al using ambulatory physiological recording. Thus, a training set of ambulatory recordings that include the measurement of panic onset is used to parameterize a model that predicts the imminent onset of the attack. As described above, the preferred model that is used to predict the attack is one that makes use of support vector machines. In use, the model also measures the ambulatory signals, calculates the likelihood of an imminent attack, and warns the patient when a panic attack is imminent. The patient or a caregiver then performs noninvasive vagal nerve stimulation as a prophylactic countermeasure as disclosed herein, the rationale for which is described more fully in the co-pending, commonly assigned application ELECTRICAL AND MAGNETIC STIMULATORS USED TO TREAT MIGRAINE/SINUS HEADACHE, RHINITIS, SINUSITIS, RHINOSINUSITIS, AND COMORBID DISORDERS.

Methods for Averting Imminent Depression Attacks

Patent application US20090292180, entitled Method and Apparatus for Analysis of Psychiatric and Physical Conditions, to MIROW, describes the use of noninvasive physiological monitoring such as the electrocardiogram and accelerometers (for activity measurement), with the aim of diagnosing psychiatric and physical conditions. Although MIROW does not describe a method for performing forecasts, she does state that "[0019] . . . Moods and emotions, themselves the result of nonlinear brain activity, cannot be accurately forecast over long time periods, (due to their "sensitive dependence upon initial conditions"), yet short-term predictions of mood and emotional state can be made by tracking their spatial-temporal patterns over time. Fully nuanced mood and emotional expressions develop slowly in humans as they grow from infancy to adulthood. A baby exhibits abrupt discontinuous changes in mood and emotional state, whereas a healthy mature adult has modulated, appropriate moods and emotional responses to change." Thus, whereas in a child, laughter or crying may be elicited upon experiencing a funny or sad situation or thought, in an adult, it may well be the case that experiencing the funny or sad situation or thought may not be enough to trigger laughing or crying. Instead, the adult may also need to be in a permissive physical and mental state for the trigger to be effective. The report by MEURET that was described above in connection with panic attacks is consistent with this view, in which the panic may be triggered by a fearful thought or situation, but a physiologically measurable permissive state that is detectable shortly before the attack may also be required, and detection of that permissive state may be used to forecast that an attack is imminent.

In the case of depression, the depressive attack would in many cases begin with the onset of crying. In the case of panic attacks, MUERET relied on the patient's pressing of an event marker button to correlate the attack with the values of ambulatory physiological or environmental measurements—respiration (abdominal and thoracic plethysmography), carbon dioxide (capnometry with nasual cannula), heart rate (electrocardiogram leads), skin impedance (electrodermal leads), vocalization (microphones), light (light sensor), motion (accelerometer), external and finger temperature (thermometers). The same could be done to forecast the onset of a crying attack of a depressed individual, but it may not be necessary to mark the attack with the pressing of an event button. This is because the crying, which results in a typical pattern of respiration, may be detected from a recorded cardio-respiratory signal and used to identify its onset and termination [Patent application US20090048500, entitled Method for using a non-invasive cardiac and respiratory monitoring system, to Corn]. Lacrimation could also be measured noninvasively using a wetness sensor applied to the corner of one or both eyes.

The trigeminal (fifth cranial) nerve bears the sensory pathway of the tear reflexes, and activates the facial (seventh cranial) nerve. Because crying is produced by lachrymal glands that are innervated by parasympathetic nerves of the seventh cranial nerve, it is thought that crying results from high levels of autonomic activation that might be detected before the onset of a crying attack [GROSS J J, Frederickson B L, Levenson R W. The psychophysiology of crying. Psychophysiology 31(5, 1994):460-8; Ad J. J. M. VINGERHOETS, Randolph R. Cornelius, Guus L. Van Heck, Marleen C. Becht. Adult Crying: A model and review of the literature. Review of General Psychology 4(4, 2000): 354-377]. The above-cited article by GROSS et al measured noninvasive signals beyond those measured by MUERET et al, and their measurement may also be useful for forecasting a state that promotes an imminent crying attack.

The disclosed invention comprises forecasting an imminent attack as was done by MUERET et al using ambulatory physiological recording, except that additional signals are recorded as described above, and the attack is a crying attack instead of a panic attack [MEURET A E, Rosenfield D, Wilhelm F H, Zhou E, Conrad A, Ritz T, Roth W T. Do Unexpected Panic Attacks Occur Spontaneously? Biol Psychiatry. 2011 Jul. 21, Epub ahead of print]. Thus, a training set of recordings that include the measurement of crying is used to parameterize a model that predicts the imminent onset of the attack. As described above, the preferred model for making the forecast makes use of support vector machines. In use, the model also measures the ambulatory signals, calculates the likelihood of an imminent attack, and warns the patient when a crying attack is imminent. The patient or a caregiver then performs noninvasive vagal nerve stimulation as a prophylactic countermeasure as disclosed herein, the rationale for which is described more fully in the co-pending, commonly assigned application NON-INVASIVE METHODS AND DEVICES FOR INDUCING EUPHORIA IN A PATIENT AND THEIR THERAPEUTIC APPLICATION.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method of treating a patient with epilepsy, the method comprising:
    positioning an electrically permeable contact surface of a housing in contact with an outer skin surface of a neck of the patient, wherein the housing contains an energy source coupled to the electrically permeable contact surface;
    generating an electric current with the energy source; and
    transmitting, as the electrically permeable contact surface is in contact with the outer skin surface, from the energy source, via the electrically permeable contact surface and the outer skin surface, the electric current transcutaneously and non-invasively to a vagus nerve in the patient, wherein the electric current is configured to modulate the vagus nerve such that the vagus nerve transmits an action potential to at least one of minimize or avert a seizure in the patient.

2. The method of claim 1, further comprising:
    generating an electric field at or near the housing; and
    shaping the electric field such that the electric field is sufficient to modulate the vagus nerve at a target region; and
    wherein the electric field is not sufficient to substantially modulate at least one of a nerve or a muscle between the outer skin surface and the target region.

3. The method of claim 1, wherein the electric current comprises bursts of pulses with a frequency from about 5 bursts per second (Hz) to about 100 bursts per second (Hz).

4. The method of claim 3, wherein each of the bursts contains from 1 to 20 pulses.

5. The method of claim 3 wherein the pulses are full sinusoidal waves.

6. The method of claim 3 wherein each of the pulses is from about 50 microseconds to about 1000 microseconds in duration.

7. The method of claim 1 wherein the transmitting has a duration of less than 5 minutes.

8. The method of claim 1 wherein the transmitting has a duration of less than 2 minutes.

9. The method of claim 1, wherein the positioning is carried out by contacting the electrically permeable contact surface to a right side of the neck of the patient.

10. The method of claim 1, wherein the electric current is directly directed to the vagus nerve.

11. A device for treating a patient with epilepsy, the device comprising:
    a housing including an outer wall and an interior surrounded by the outer wall, wherein the outer wall includes an electrically permeable contact surface configured to contact an outer skin surface of a neck of the patient;
an energy source positioned within the interior of the housing, wherein the energy source is configured to generate an electric current and to transmit, as the electrically permeable contact surface is in contact with the outer skin surface, from the energy source, the electric current transcutaneously and non-invasively via the electrically permeable contact surface to a vagus nerve within the patient; and
    wherein the electric current is configured to modulate the vagus nerve such that the vagus nerve transmits an action potential to at least one of avert or at least partially ameliorate a seizure in the patient.

12. The device of claim 11, wherein the energy source comprises a signal generator and an electrode coupled to the signal generator within the housing.

13. The device of claim 12, further comprising:
    a conducting medium positioned within the housing between the electrode and the electrically permeable contact surface.

14. The device of claim 12, wherein the signal generator is configured to generate an electric field comprising bursts of pulses with a frequency from about 5 bursts per second to about 100 bursts per second.

15. The device of claim 14, wherein the electric field comprises bursts from 1 pulse to 20 pulses with each of the pulses from about 50 microseconds to about 1000 microseconds in duration.

16. The device of claim 11 wherein the energy source comprises a battery.

17. The device of claim 11 wherein the housing is a handheld device configured for contacting the outer skin surface of the neck of the patient.

18. The device of claim 11, wherein the electrically permeable contact surface comprises a pair of stainless steel discs situated on a side of the housing.

19. The device of claim 11, wherein the electric current comprises bursts of about 2 to about 20 pulses with a frequency from about 5 bursts per second to about 100 bursts per second with each of the pulses being from about 50 microseconds to about 1000 microseconds in duration.

* * * * *